(12) United States Patent
Sharpe et al.

(10) Patent No.: US 6,218,510 B1
(45) Date of Patent: Apr. 17, 2001

(54) B7-1 AND B7-2 POLYPEPTIDES

(75) Inventors: Arlene H. Sharpe; Francescopaolo Borriello; Gordon J. Freeman, all of Brookline; Lee M. Nadler, Newton, all of MA (US)

(73) Assignees: Brigham & Woman's Hospital; Dana-Farber Cancer Institute, both of Boston, MA (US)

( * ) Notice: Subject to any disclaimer, the term of this patent is extended or adjusted under 35 U.S.C. 154(b) by 0 days.

(21) Appl. No.: 08/205,697

(22) Filed: Mar. 2, 1994

(51) Int. Cl.$^7$ .................. C07K 14/47; C07K 14/705; C07K 7/00
(52) U.S. Cl. .................. 530/350; 530/325; 530/324; 530/323; 536/23.1; 536/23.4; 536/23.5
(58) Field of Search .................. 935/69.7; 530/350, 530/324, 325, 326, 327, 328, 329, 330, 323, 23.1; 536/23.4, 23.5

(56) References Cited

FOREIGN PATENT DOCUMENTS

WO 92/00092  1/1992  (WO).

OTHER PUBLICATIONS

Augustin, M. et al. (1993) "Phorbol–12–Myristate–13–Acetate–Treated Human Keratinocytes Express B7–Like Molecules That Serve a Costimulatory Role in T–Cell Activation" *J. Invest. Dermatol.* 100(3):275–281.
Freeman et al., (1993), "Murine B7–2, an Alternative CTLA4 Counter–receptor that Costimulates T Cell Proliferation and Interleukin 2 Production", *The Journal of Experimental Medicine,* vol. 178, pp. 2185–2192.
Freeman et al., (1993), "Uncovering of Functional Alternative CTLA–4 Counter–Receptor in B7–Deficient Mice", *Science,* vol. 262, pp. 907–909.
Freeman et al., (1993), "Cloning of B7–2: A CTLA–4 Counter–Receptor That Costimulates Human T Cell Proliferation", *Science,* vol. 262, pp. 909–911.
Hathcock et al., (1993), "Identification of an Alternative CTLA–4 Ligand Costimulatory for T Cell Activation", *Science,* vol. 262, pp. 905–907.
Azuma et al., (1993), "B70 antigen is a second ligand for CTLA–4 and CD28", *Nature,* vol. 366, pp. 76–79.
Tan et al., (1993), "Induction of Alloantigen–specific Hyporesponsiveness in Human T Lymphocytes by Blocking Interactions of CD28 with Its Natural Ligand B7/BB1", *Journal of Experimental Medicine,* vol. 177, pp. 165–173.

Selvakumar et al., (1993), "Genomic organization of the mouse B–lymphocyte activation antigen B7", *Immunogenetics,* vol. 38, pp. 292–295.
Selvakumar et al., (1992), "Genomic organization and chromosomal location of the human gene encoding the B–lymphocyte activation antigen B7", *Immunogenetics,* vol. 36, pp. 175–181.
Harding et al., (1992), "CD28–mediated signalling co–stimulates murine T cells and prevents induction of anergy in T–cell clones", *Nature,* vol. 356, pp. 607–609.
Freeman et al., (1992), "The Gene for B7, a Costimulatory Signal for T–Cell Activation, Maps to Chromosomal Region 3q13.3–3–3q21", *Blood,* vol. 79, No. 2, pp. 489–494.
Linsley et al., (1991), "Binding of the B Cell Activation Antigen B& to CD28 Costimulates T Cell Proliferation and interleukin 2 mRNA Accumulation", *Journal of Experimental Medicine, vol.*173, pp. 721–730.
Gimmi et al., (1991), "B–cell surface antigen B7 provides a costimulatory signal that induces T cells to proliferate and secrete interleukin 2", *Proceedings of the National Academy of Sciences,* vol. 88, pp. 6575–6579.
Freeman et al., (1991), "Structure, Expression, and T Cell Costimulatory Activity of the Murine Homologue of the Human B Lymphocyte Activation Antigen B7", *Journal of Experimental Medicine,* vol. 147, pp. 625–631.
Freedman et al., (1989), "B7, A New Member of the Ig Superfamily With Unique Expression on Activated and Neoplastic B Cells", *Journal of Immunology,* vol. 143, pp. 2714–2722.
Freeman et al., (1987), "B7, A B Cell–restricted Antigen That Identifies Preactivated B Cells", *The Journal of Immunology,* vol. 139, No. 10, pp. 3260–3267.

*Primary Examiner*—Phillip Gambel
(74) *Attorney, Agent, or Firm*—Lahive & Cockfield LLP

(57) ABSTRACT

Structural forms of T cell costimulatory B7-1 and B7-2 molecules are described. These structural forms comprise a structural domain or have a structural domain deleted or added. The structural forms correspond to naturally-occurring alternatively spliced forms of T cell costimulatory molecules or variants thereof which can be produced by standard recombinant DNA techniques. In one embodiment, the T cell costimulatory molecule of the invention contains a cytoplasmic domain. In another embodiment, the T cell costimulatory molecule of the invention contains a signal peptide domain or has an immunoglobulin variable region-like domain deleted. The structural forms of T cell costimulatory molecules can be used to identify agents which stimulate the expression of alternative forms of costimulatory molecules and to identify components of the signal transduction pathway which results in costimulation of T cells.

12 Claims, 2 Drawing Sheets

SEQUENCE LISTING (1) GENERAL INFORMATION:

(iii) NUMBER OF SEQUENCES: 61

(2) INFORMATION FOR SEQ ID NO:1:

(i) SEQUENCE CHARACTERISTICS:
      (A) LENGTH: 1888 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 249..1208

(xi) SEQUENCE DESCRIPTION: SEQ ID NO:1:

```
GAGTTTTATA CCTCAATAGA CTCTTACTAG TTTCTCTTTT TCAGGTTGTG AAACTCAACC    60

TTCAAAGACA CTCTGTTCCA TTTCTGTGGA CTAATAGGAT CATCTTTAGC ATCTGCCGGG   120

TGGATGCCAT CCAGGCTTCT TTTTCTACAT CTCTGTTTCT CGATTTTTGT GAGCCTAGGA   180

GGTGCCTAAG CTCCATTGGC TCTAGATTCC TGGCTTTCCC CATCATGTTC TCCAAAGCAT   240

CTGAAGCT ATG GCT TGC AAT TGT CAG TTG ATG CAG GAT ACA CCA CTC CTC    290
         Met Ala Cys Asn Cys Gln Leu Met Gln Asp Thr Pro Leu Leu
           1               5                  10

AAG TTT CCA TGT CCA AGG CTC AAT CTT CTC TTT GTG CTG CTG ATT CGT    338
Lys Phe Pro Cys Pro Arg Leu Asn Leu Leu Phe Val Leu Leu Ile Arg
 15              20                  25                  30

CTT TCA CAA GTG TCT TCA GAT GTT GAT GAA CAA CTG TCC AAG TCA GTG    386
Leu Ser Gln Val Ser Ser Asp Val Asp Glu Gln Leu Ser Lys Ser Val
                 35                  40                  45

AAA GAT AAG GTA TTG CTG CCT TGC CGT TAC AAC TCT CCT CAT GAA GAT    434
Lys Asp Lys Val Leu Leu Pro Cys Arg Tyr Asn Ser Pro His Glu Asp
             50                  55                  60

GAG TCT GAA GAC CGA ATC TAC TGG CAA AAA CAT GAC AAA GTG GTG CTG    482
Glu Ser Glu Asp Arg Ile Tyr Trp Gln Lys His Asp Lys Val Val Leu
         65                  70                  75

TCT GTC ATT GCT GGG AAA CTA AAA GTG TGG CCC GAG TAT AAG AAC CGG    530
Ser Val Ile Ala Gly Lys Leu Lys Val Trp Pro Glu Tyr Lys Asn Arg
     80                  85                  90

ACT TTA TAT GAC AAC ACT ACC TAC TCT CTT ATC ATC CTG GGC CTG GTC    578
Thr Leu Tyr Asp Asn Thr Thr Tyr Ser Leu Ile Ile Leu Gly Leu Val
 95                 100                 105                 110

CTT TCA GAC CGG GGC ACA TAC AGC TGT GTC GTT CAA AAG AAG GAA AGA    626
Leu Ser Asp Arg Gly Thr Tyr Ser Cys Val Val Gln Lys Lys Glu Arg
                115                 120                 125

GGA ACG TAT GAA GTT AAA CAC TTG GCT TTA GTA AAG TTG TCC ATC AAA    674
Gly Thr Tyr Glu Val Lys His Leu Ala Leu Val Lys Leu Ser Ile Lys
            130                 135                 140

GCT GAC TTC TCT ACC CCC AAC ATA ACT GAG TCT GGA AAC CCA TCT GCA    722
Ala Asp Phe Ser Thr Pro Asn Ile Thr Glu Ser Gly Asn Pro Ser Ala
        145                 150                 155

GAC ACT AAA AGG ATT ACC TGC TTT GCT TCC GGG GGT TTC CCA AAG CCT    770
Asp Thr Lys Arg Ile Thr Cys Phe Ala Ser Gly Gly Phe Pro Lys Pro
    160                 165                 170

CGC TTC TCT TGG TTG GAA AAT GGA AGA GAA TTA CCT GGC ATC AAT ACG    818
Arg Phe Ser Trp Leu Glu Asn Gly Arg Glu Leu Pro Gly Ile Asn Thr
175                 180                 185                 190
```

```
ACA ATT TCC CAG GAT CCT GAA TCT GAA TTG TAC ACC ATT AGT AGC CAA      866
Thr Ile Ser Gln Asp Pro Glu Ser Glu Leu Tyr Thr Ile Ser Ser Gln
            195                 200                 205

CTA GAT TTC AAT ACG ACT CGC AAC CAC ACC ATT AAG TGT CTC ATT AAA      914
Leu Asp Phe Asn Thr Thr Arg Asn His Thr Ile Lys Cys Leu Ile Lys
            210                 215                 220

TAT GGA GAT GCT CAC GTG TCA GAG GAC TTC ACC TGG GAA AAA CCC CCA      962
Tyr Gly Asp Ala His Val Ser Glu Asp Phe Thr Trp Glu Lys Pro Pro
            225                 230                 235

GAA GAC CCT CCT GAT AGC AAG AAC ACA CTT GTG CTC TTT GGG GCA GGA     1010
Glu Asp Pro Pro Asp Ser Lys Asn Thr Leu Val Leu Phe Gly Ala Gly
        240                 245                 250

TTC GGC GCA GTA ATA ACA GTC GTC GTC ATC GTT GTC ATC ATC AAA TGC     1058
Phe Gly Ala Val Ile Thr Val Val Val Ile Val Val Ile Ile Lys Cys
255                 260                 265                 270

TTC TGT AAG CAC GGT CTC ATC TAC CAT TTG CAA CTG ACC TCT TCT GCA     1106
Phe Cys Lys His Gly Leu Ile Tyr His Leu Gln Leu Thr Ser Ser Ala
                275                 280                 285

AAG GAC TTC AGA AAC CTA GCA CTA CCC TGG CTC TGC AAA CAC GGT TCT     1154
Lys Asp Phe Arg Asn Leu Ala Leu Pro Trp Leu Cys Lys His Gly Ser
            290                 295                 300

CTA GGT GAA GCC TCT GCA GTG ATT TGC AGA AGT ACT CAG ACG AAT GAA     1202
Leu Gly Glu Ala Ser Ala Val Ile Cys Arg Ser Thr Gln Thr Asn Glu
        305                 310                 315

CCA CAG TAGTTCTGCT GTTTCTGAGG ACGTAGTTTA GAGACTGAAT TCTTTGGAAA      1258
Pro Gln
    320

GGACATAGGG ACAGTTTGCA CATTTGCTTG CACATCACAC ACACACACAC ACACACACAC   1318

ACACACACAC ACACACACAC ACACACACAC ACACACACAC TCTCTCTCTC TCTCTCTCTC   1378

GATACCTTAG GATAGGGTTC TACCCTGTTG CTCAGTGACA AAGAATCACT CTGTGGCGGA   1438

GGCAGGCTTC AAGCTTGCAG CAATCCTCCT GCACCAGTTT CCTGAGTGCC AGACTTCCAG   1498

GTGTAAGCTA TGGCACTTAG CAGAAACACTA GCTGAATCAA TGAAGACACT GAGGTTCCAA  1558

GAGGGAACCT GAATTATGAA GGTGAGTCAG AATCCAGATT TCCTGGCTCT ACCACTCTTA   1618

ACCTGTATCT GTTAGACCCC AAGCTCTGAG CTCATAGACA AGCTAATTTA AAATGCTTTT   1678

TAATAAGCAG AAGGCTCAGT TAGTACGGGG TTCAGGATAC TGCTTACTGG CAATATTTGA   1738

CTAGCCTCTA TTTTGTTTGT TTTTTAAAGG CCTACTGACT GTAGTGTAAT TTGTAGGAAA   1798

CATGTTGCTA TGTATACCCA TTTGAGGGTA ATAAAAATGT TGGTAATTTT CAGCCAGCAC   1858

TTTCCAGGTA TTTCCCTTTT TATCCTTCAT                                    1888

(2) INFORMATION FOR SEQ ID NO:2:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Cys Asn Cys Gln Leu Met Gln Asp Thr Pro Leu Leu Lys Phe
 1               5                  10                  15

Pro Cys Pro Arg Leu Asn Leu Leu Phe Val Leu Leu Ile Arg Leu Ser
                20                  25                  30

Gln Val Ser Ser Asp Val Asp Glu Gln Leu Ser Lys Ser Val Lys Asp
            35                  40                  45
```

```
Lys Val Leu Leu Pro Cys Arg Tyr Asn Ser Pro His Glu Asp Glu Ser
         50                  55                  60

Glu Asp Arg Ile Tyr Trp Gln Lys His Asp Lys Val Val Leu Ser Val
 65                  70                  75                  80

Ile Ala Gly Lys Leu Lys Val Trp Pro Glu Tyr Lys Asn Arg Thr Leu
                 85                  90                  95

Tyr Asp Asn Thr Thr Tyr Ser Leu Ile Ile Leu Gly Leu Val Leu Ser
                100                 105                 110

Asp Arg Gly Thr Tyr Ser Cys Val Val Gln Lys Lys Glu Arg Gly Thr
                115                 120                 125

Tyr Glu Val Lys His Leu Ala Leu Val Lys Leu Ser Ile Lys Ala Asp
130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
                180                 185                 190

Ser Gln Asp Pro Glu Ser Glu Leu Tyr Thr Ile Ser Ser Gln Leu Asp
                195                 200                 205

Phe Asn Thr Thr Arg Asn His Thr Ile Lys Cys Leu Ile Lys Tyr Gly
210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
                260                 265                 270

Lys His Gly Leu Ile Tyr His Leu Gln Leu Thr Ser Ser Ala Lys Asp
                275                 280                 285

Phe Arg Asn Leu Ala Leu Pro Trp Leu Cys Lys His Gly Ser Leu Gly
                290                 295                 300

Glu Ala Ser Ala Val Ile Cys Arg Ser Thr Gln Thr Asn Glu Pro Gln
305                 310                 315                 320

(2) INFORMATION FOR SEQ ID NO:3:

(i) SEQUENCE CHARACTERISTICS:
        (A) LENGTH: 2516 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 249..1166

(xi) SEQUENCE DESCRIPTION: SEQ ID NO:3:

GAGTTTTATA CCTCAATAGA CTCTTACTAG TTTCTCTTTT TCAGGTTGTG AAACTCAACC      60

TTCAAAGACA CTCTGTTCCA TTTCTGTGGA CTAATAGGAT CATCTTTAGC ATCTGCCGGG    120

TGGATGCCAT CCAGGCTTCT TTTTCTACAT CTCTGTTTCT CGATTTTTGT GAGCCTAGGA    180

GGTGCCTAAG CTCCATTGGC TCTAGATTCC TGGCTTTCCC CATCATGTTC TCCAAAGCAT    240

CTGAAGCT ATG GCT TGC AAT TGT CAG TTG ATG CAG GAT ACA CCA CTC CTC    290
         Met Ala Cys Asn Cys Gln Leu Met Gln Asp Thr Pro Leu Leu
```

```
                1               5                       10
AAG TTT CCA TGT CCA AGG CTC AAT CTT CTC TTT GTG CTG CTG AAT CGT    338
Lys Phe Pro Cys Pro Arg Leu Asn Leu Leu Phe Val Leu Leu Asn Arg
 15              20                  25                  30

CTT TCA CAA GTG TCT TCA GAT GTT GAT GAA CAA CTG TCC AAG TCA GTG    386
Leu Ser Gln Val Ser Ser Asp Val Asp Glu Gln Leu Ser Lys Ser Val
                 35                  40                  45

AAA GAT AAG GTA TTG CTG CCT TGC CGT TAC AAC TCT CCT CAT GAA GAT    434
Lys Asp Lys Val Leu Leu Pro Cys Arg Tyr Asn Ser Pro His Glu Asp
             50                  55                  60

GAG TCT GAA GAC CGA ATC TAC TGG CAA AAA CAT GAC AAA GTG GTG CTG    482
Glu Ser Glu Asp Arg Ile Tyr Trp Gln Lys His Asp Lys Val Val Leu
         65                  70                  75

TCT GTC ATT GCT GGG AAA CTA AAA GTG TGG CCC GAG TAT AAG AAC CGG    530
Ser Val Ile Ala Gly Lys Leu Lys Val Trp Pro Glu Tyr Lys Asn Arg
     80                  85                  90

ACT TTA TAT GAC AAC ACT ACC TAC TCT CTT ATC ATC CTG GGC CTG GTC    578
Thr Leu Tyr Asp Asn Thr Thr Tyr Ser Leu Ile Ile Leu Gly Leu Val
 95                 100                 105                 110

CTT TCA GAC CGG GGC ACA TAC AGC TGT GTC GTT CAA AAG AAG GAA AGA    626
Leu Ser Asp Arg Gly Thr Tyr Ser Cys Val Val Gln Lys Lys Glu Arg
                115                 120                 125

GGA ACG TAT GAA GTT AAA CAC TTG GCT TTA GTA AAG TTG TCC ATC AAA    674
Gly Thr Tyr Glu Val Lys His Leu Ala Leu Val Lys Leu Ser Ile Lys
            130                 135                 140

GCT GAC TTC TCT ACC CCC AAC ATA ACT GAG TCT GGA AAC CCA TCT GCA    722
Ala Asp Phe Ser Thr Pro Asn Ile Thr Glu Ser Gly Asn Pro Ser Ala
        145                 150                 155

GAC ACT AAA AGG ATT ACC TGC TTT GCT TCC GGG GGT TTC CCA AAG CCT    770
Asp Thr Lys Arg Ile Thr Cys Phe Ala Ser Gly Gly Phe Pro Lys Pro
    160                 165                 170

CGC TTC TCT TGG TTG GAA AAT GGA AGA GAA TTA CCT GGC ATC AAT ACG    818
Arg Phe Ser Trp Leu Glu Asn Gly Arg Glu Leu Pro Gly Ile Asn Thr
175                 180                 185                 190

ACA ATT TCC CAG GAT CCT GAA TCT GAA TTG TAC ACC ATT AGT AGC CAA    866
Thr Ile Ser Gln Asp Pro Glu Ser Glu Leu Tyr Thr Ile Ser Ser Gln
                195                 200                 205

CTA GAT TTC AAT ACG ACT CGC AAC CAC ACC ATT AAG TGT CTC ATT AAA    914
Leu Asp Phe Asn Thr Thr Arg Asn His Thr Ile Lys Cys Leu Ile Lys
            210                 215                 220

TAT GGA GAT GCT CAC GTG TCA GAG GAC TTC ACC TGG GAA AAA CCC CCA    962
Tyr Gly Asp Ala His Val Ser Glu Asp Phe Thr Trp Glu Lys Pro Pro
        225                 230                 235

GAA GAC CCT CCT GAT AGC AAG AAC ACA CTT GTG CTC TTT GGG GCA GGA    1010
Glu Asp Pro Pro Asp Ser Lys Asn Thr Leu Val Leu Phe Gly Ala Gly
    240                 245                 250

TTC GGC GCA GTA ATA ACA GTC GTC GTC ATC GTT GTC ATC ATC AAA TGC    1058
Phe Gly Ala Val Ile Thr Val Val Val Ile Val Val Ile Ile Lys Cys
255                 260                 265                 270

TTC TGT AAG CAC AGA AGC TGT TTC AGA AGA AAT GAG GCA AGC AGA GAA    1106
Phe Cys Lys His Arg Ser Cys Phe Arg Arg Asn Glu Ala Ser Arg Glu
                275                 280                 285

ACA AAC AAC AGC CTT ACC TTC GGG CCT GAA GAA GCA TTA GCT GAA CAG    1154
Thr Asn Asn Ser Leu Thr Phe Gly Pro Glu Glu Ala Leu Ala Glu Gln
            290                 295                 300

ACC GTC TTC CTT TAGTTCTTCT CTGTCCATGT GGGATACATG GTATTATGTG         1206
Thr Val Phe Leu
            305

GCTCATGAGG TACAATCTTT CTTTCAGCAC CGTGCTAGCT GATCTTTCGG ACAACTTGAC   1266
```

-continued

```
ACAAGATAGA GTTAACTGGG AAGAGAAAGC CTTGAATGAG GATTTCTTTC CATCAGGAAG    1326

CTACGGGCAA GTTTGCTGGG CCTTTGATTG CTTGATGACT GAAGTGGAAA GGCTGAGCCC    1386

ACTGTGGGTG GTGCTAGCCC TGGGCAGGGG CAGGTGACCC TGGGTGGTAT AAGAAAAAGA    1446

GCTGTCACTA AAAGGAGAGG TGCCTAGTCT TACTGCAACT TGATATGTCA TGTTTGGTTG    1506

GTGTCTGTGG GAGGCCTGCC CTTTTCTGAA GAGAAGTGGT GGGAGAGTGG ATGGGGTGGG    1566

GGCAGAGGAA AAGTGGGGGA GAGGGCCTGG GAGGAGAGGA GGGAGGGGGA CGGGGTGGGG    1626

GTGGGGAAAA CTATGGTTGG GATGTAAAAA CGGATAATAA TATAAATATT AAATAAAAAG    1686

AGAGTATTGA GCGGTCTCAT CTACCATTTG CAACTGACCT CTTCTGCAAA GGACTTCAGA    1746

AACCTAGCAC TACCCTGGCT CTGCAAACAC GGTTCTCTAG GTGAAGCCTC TGCAGTGATT    1806

TGCAGAAGTA CTCAGACGAA TGAACCACAG TAGTTCTGCT GTTTCTGAGG ACGTAGTTTA    1866

GAGACTGAAT TCTTTGGAAA GGACATAGGG ACAGTTTGCA CATTTGCTTG CACATCACAC    1926

ACACACACAC ACACACACAC ACACACACAC ACACACACAC ACACACACAC ACACACACAC    1986

TCTCTCTCTC TCTCTCTCTC GATACCTTAG GATAGGGTTC TACCCTGTTG CTCAGTGACA    2046

AAGAATCACT CTGTGGCGGA GGCAGGCTTC AAGCTTGCAG CAATCCTCCT GCACCAGTTT    2106

CCTGAGTGCC AGACTTCCAG GTGTAAGCTA TGGCACTTAG CAGAACACTA GCTGAATCAA    2166

TGAAGACACT GAGGTTCCAA GAGGGAACCT GAATTATGAA GGTGAGTCAG AATCCAGATT    2226

TCCTGGCTCT ACCACTCTTA ACCTGTATCT GTTAGACCCC AAGCTCTGAG CTCATAGACA    2286

AGCTAATTTA AAATGCTTTT TAATAAGCAG AAGGCTCAGT TAGTACGGGG TTCAGGATAC    2346

TGCTTACTGG CAATATTTGA CTAGCCTCTA TTTTGTTTGT TTTTTAAAGG CCTACTGACT    2406

GTAGTGTAAT TTGTAGGAAA CATGTTGCTA TGTATACCCA TTTGAGGGTA ATAAAAATGT    2466

TGGTAATTTT CAGCCAGCAC TTTCCAGGTA TTTCCCTTTT TATCCTTCAT               2516
```

(2) INFORMATION FOR SEQ ID NO:4:

(i) SEQUENCE CHARACTERISTICS:
        (A) LENGTH: 818 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..138

(xi) SEQUENCE DESCRIPTION: SEQ ID NO:4:

```
GGT CTC ATC TAC CAT TTG CAA CTG ACC TCT TCT GCA AAG GAC TTC AGA         48
Gly Leu Ile Tyr His Leu Gln Leu Thr Ser Ser Ala Lys Asp Phe Arg
 1               5                  10                  15

AAC CTA GCA CTA CCC TGG CTC TGC AAA CAC GGT TCT CTA GGT GAA GCC         96
Asn Leu Ala Leu Pro Trp Leu Cys Lys His Gly Ser Leu Gly Glu Ala
             20                  25                  30

TCT GCA GTG ATT TGC AGA AGT ACT CAG ACG AAT GAA CCA CAG                138
Ser Ala Val Ile Cys Arg Ser Thr Gln Thr Asn Glu Pro Gln
         35                  40                  45

TAGTTCTGCT GTTTCTGAGG ACGTAGTTTA GAGACTGAAT TCTTTGGAAA GGACATAGGG    198

ACAGTTTGCA CATTTGCTTG CACATCACAC ACACACACAC ACACACACAC ACACACACAC    258

ACACACACAC ACACACACAC ACACACACAC TCTCTCTCTC TCTCTCTCTC GATACCTTAG    318

GATAGGGTTC TACCCTGTTG CTCAGTGACA AAGAATCACT CTGTGGCGGA GGCAGGCTTC    378
```

-continued

```
AAGCTTGCAG CAATCCTCCT GCACCAGTTT CCTGAGTGCC AGACTTCCAG GTGTAAGCTA      438

TGGCACTTAG CAGAACACTA GCTGAATCAA TGAAGACACT GAGGTTCCAA GAGGGAACCT      498

GAATTATGAA GGTGAGTCAG AATCCAGATT TCCTGGCTCT ACCACTCTTA ACCTGTATCT      558

GTTAGACCCC AAGCTCTGAG CTCATAGACA AGCTAATTTA AAATGCTTTT TAATAAGCAG      618

AAGGCTCAGT TAGTACGGGG TTCAGGATAC TGCTTACTGG CAATATTTGA CTAGCCTCTA      678

TTTTGTTTGT TTTTTAAAGG CCTACTGACT GTAGTGTAAT TTGTAGGAAA CATGTTGCTA      738

TGTATACCCA TTTGAGGGTA ATAAAAATGT TGGTAATTTT CAGCCAGCAC TTTCCAGGTA      798

TTTCCCTTTT TATCCTTCAT                                                 818
```

(2) INFORMATION FOR SEQ ID NO:5:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO:5:

```
Gly Leu Ile Tyr His Leu Gln Leu Thr Ser Ser Ala Lys Asp Phe Arg
 1               5                  10                  15

Asn Leu Ala Leu Pro Trp Leu Cys Lys His Gly Ser Leu Gly Glu Ala
             20                  25                  30

Ser Ala Val Ile Cys Arg Ser Thr Gln Thr Asn Glu Pro Gln
         35                  40                  45
```

(2) INFORMATION FOR SEQ ID NO:6:

(i) SEQUENCE CHARACTERISTICS:
        (A) LENGTH: 1753 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

```
GTTTTAGTAA CCAGAGGCCG CAAGAAGAGA TCACTTGTAT ATACACGGGC CCCATCTTTT       60

GCTTTTTAAG ACAAAAGAAA AAGAATCTTC TTCAACAAGT AAGTAAATGC ATTTACTATT      120

TATCATGCTA TGGGACACCT TAGTAGAACA CGCTATCTCC AGCCTTATCA TATGCATATT      180

TTGTTGTTGT TGTTGTTGTT GTTGTTAAAG ACAGGGTCTC ATATATGCCA GGCTGGTCCC      240

AAACTTTCAG TGTAACCCAA GATAATCTGG AACTCCCGAC TCCTCTGCTC CCACCTCTCC      300

AGTGCAGGAC ACTGTTTATA CCGTGCTGGG GAATTGAACT CAGAGCACCC TGCATGTCAG      360

CTAAGCATTC TACCGACCAA GTCCCATGCC CAGTCCCTAA CTCCCCAACT TCACTGCTTT      420

TTAAACATAC ATACAATCAT AACTTGCCCT CAGAGCAGTC TCCTGGGGTC TCTTATTCTC      480

AAGGCTGCGG CATTCCAACA CTGTTAGAAA AACACCATCA GGATTCTTTT GTGTTTCCTA      540

GATGCAAACA TTTTTGTAGG GCGAAGTTGA GGTTTTTCTA ATCAAGAAAA TGCCGGTAAC      600

AAGTCTCTTC AAGCTAACTG GTTGGCTAAG GGGTATCTCT CCAAAAGAAG AGATCCACAT      660

GTCAGGCCAG TTGTAGGCAT GATGTCAGGT CTCCCTCCCT TTCTTTCTTT CTTTCTTTTT      720

TTCTTTCTTT CTTTTTTTCT TTCTTTCTTA CTTTCTTACT TTCTTTCTTT TCTGTTTTTT      780

GGTTTTTCGA GACAGGGTTT CTTTGTATAG CCCTGGCTGT CCTGGAACTC GCTCTGTAGA      840
```

-continued

```
CCAGGCTGGC CTCGAACTCA GAAATCTGCC TCTGCCTTTA CCTCCTGAGT GCTGGGAATT      900

AAAGGTGTGC ACCACCATGC CCGGCTGGGA TGTCATTCGT TTTCATTTCT CAATTTTGAT      960

ACTTTATGGA AGAAAAAAGA AAAGATAGAC AAGCCTCTTC ATGTAATACC CCATAGTCTC     1020

AATAAGTGGT GTTCGTAACG TGGCTTCTCT TTCCTTACCT TTTACTGGTA GATTTCTCGG     1080

TTGATTGATG TCCCTGTAGG ACTTACTGGG TTTAAGATTC TTGGTTTCCT GTTTTAAGAT     1140

ATAAAGAAAC CATTTCCTAA CTAAAACACT GCCTTGGACA AATATACTTT TGGCAGTCAC     1200

TCTGTGTCCA GAATGGAATT TAAGCTTTCA TGGCCTAGCT GCTAGTGAAG GTTCTTTGCT     1260

TTTTTTTGGC TGTTGTATGT GAAATGGGGT TGGGTGGGAA CCACCTCACT GTGTTCTAGT     1320

GTTAGTCACC CCACCCCCGC AAGCAGAATC CTTTTACCCA GCTTTTTCAC CCAGCTGTGC     1380

TCACCCGGTG CTCAGAACAG GCCTGGACAA GTCACCTCCC CTAGAGTTCT GGGGACCTTT     1440

GAGTTGCCCT CATGGCCACA CCCTGATTCA GAACTCTCAC TCTGTCGTAA GATAGAGCTA     1500

CTGGGGAGTT TTATACCTCA ATAGACTCTT ACTAGTTTCT CTTTTTCAGG TTGTGAAACT     1560

CAACCTTCAA AGACACTCTG TTCCATTTCT GTGGACTAAT AGGATCATCT TTAGCATCTG     1620

CCGGGTGGAT GCCATCCAGG CTTCTTTTTC TACATCTCTG TTTCTCGATT TTTGTGAGCC     1680

TAGGAGGTGC CTAAGCTCCA TTGGCTCTAG ATTCCTGGCT TTCCCCATCA TGTTCTCCAA     1740

AGCATCTGAA GCT                                                       1753
```

(2) INFORMATION FOR SEQ ID NO:7:

(i) SEQUENCE CHARACTERISTICS:
        (A) LENGTH: 158 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:7:

```
TGTCCAGGCA GAGCTAGTGG CTGCCCCTAG CGCTTCCTCT TCTTTGATAC CCCAAAGTCT       60

GAGTTTATTA CACATCCTTG GTGACCAAAT CACATGGGAG CTTCCTCCGA GGTCTTAGTA      120

AAGGGAAGTT GGAAAGGGGA AATTCCTGCC CCCCTGCC                              158
```

(2) INFORMATION FOR SEQ ID NO:8:

(i) SEQUENCE CHARACTERISTICS:
        (A) LENGTH: 1398 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 249..848

(xi) SEQUENCE DESCRIPTION: SEQ ID NO:8:

```
GAGTTTTATA CCTCAATAGA CTCTTACTAG TTTCTCTTTT TCAGGTTGTG AAACTCAACC       60

TTCAAAGACA CTCTGTTCCA TTTCTGTGGA CTAATAGGAT CATCTTTAGC ATCTGCCGGG      120

TGGATGCCAT CCAGGCTTCT TTTTCTACAT CTCTGTTTCT CGATTTTTGT GAGCCTAGGA      180

GGTGCCTAAG CTCCATTGGC TCTAGATTCC TGGCTTTCCC CATCATGTTC TCCAAAGCAT      240

CTGAAGCT ATG GCT TGC AAT TGT CAG TTG ATG CAG GAT ACA CCA CTC CTC      290
         Met Ala Cys Asn Cys Gln Leu Met Gln Asp Thr Pro Leu Leu
           1               5                  10
```

```
AAG TTT CCA TGT CCA AGG CTC AAT CTT CTC TTT GTG CTG CTG ATT CGT       338
Lys Phe Pro Cys Pro Arg Leu Asn Leu Leu Phe Val Leu Leu Ile Arg
 15              20                  25                  30

CTT TCA CAA GTG TCT TCA GCT GAC TTC TCT ACC CCC AAC ATA ACT GAG       386
Leu Ser Gln Val Ser Ser Ala Asp Phe Ser Thr Pro Asn Ile Thr Glu
                 35                  40                  45

TCT GGA AAC CCA TCT GCA GAC ACT AAA AGG ATT ACC TGC TTT GCT TCC       434
Ser Gly Asn Pro Ser Ala Asp Thr Lys Arg Ile Thr Cys Phe Ala Ser
             50                  55                  60

GGG GGT TTC CCA AAG CCT CGC TTC TCT TGG TGG GAA AAT GGA AGA GAA       482
Gly Gly Phe Pro Lys Pro Arg Phe Ser Trp Trp Glu Asn Gly Arg Glu
         65                  70                  75

TTA CCT GGC ATC AAT ACG ACA ATT TCC CAG GAT CCT GAA TCT GAA TTG       530
Leu Pro Gly Ile Asn Thr Thr Ile Ser Gln Asp Pro Glu Ser Glu Leu
     80                  85                  90

TAC ACC ATT AGT AGC CAA CTA GAT TTC AAT ACG ACT CGC AAC CAC ACC       578
Tyr Thr Ile Ser Ser Gln Leu Asp Phe Asn Thr Thr Arg Asn His Thr
 95                 100                 105                 110

ATT AAG TGT CTC ATT AAA TAT GGA GAT GCT CAC GTG TCA GAG GAC TTC       626
Ile Lys Cys Leu Ile Lys Tyr Gly Asp Ala His Val Ser Glu Asp Phe
                115                 120                 125

ACC TGG GAA AAA CCC CCA GAA GAC CCT CCT GAT AGC AAG AAC ACA CTT       674
Thr Trp Glu Lys Pro Pro Glu Asp Pro Pro Asp Ser Lys Asn Thr Leu
            130                 135                 140

GTG CTC TTT GGG GCA GGA TTC GGC GCA GTA ATA ACA GTC GTC GTC ATC       722
Val Leu Phe Gly Ala Gly Phe Gly Ala Val Ile Thr Val Val Val Ile
        145                 150                 155

GTT GTC ATC ATC AAA TGC TTC TGT AAG CAC AGA AGC TGT TTC AGA AGA       770
Val Val Ile Ile Lys Cys Phe Cys Lys His Arg Ser Cys Phe Arg Arg
    160                 165                 170

AAT GAG GCA AGC AGA GAA ACA AAC AAC AGC CTT ACC TTC GGG CCT GAA       818
Asn Glu Ala Ser Arg Glu Thr Asn Asn Ser Leu Thr Phe Gly Pro Glu
175                 180                 185                 190

GAA GCA TTA GCT GAA CAG ACC GTC TTC CTT TAGTTCTTCT CTGTCCATGT         868
Glu Ala Leu Ala Glu Gln Thr Val Phe Leu
                195                 200

GGGATACATG GTATTATGTG GCTCATGAGG TACAATCTTT CTTTCAGCAC CGTGCTAGCT     928

GATCTTTCGG ACAACTTGAC ACAAGATAGA GTTAACTGGG AAGAGAAAGC CTTGAATGAG     988

GATTTCTTTC CATCAGGAAG CTACGGGCAA GTTTGCTGGG CCTTTGATTG CTTGATGACT    1048

GAAGTGGAAA GGCTGAGCCC ACTGTGGGTG GTGCTAGCCC TGGGCAGGGG CAGGTGACCC    1108

TGGGTGGTAT AAGAAAAAGA GCTGTCACTA AAAGGAGAGG TGCCTAGTCT TACTGCAACT    1168

TGATATGTCA TGTTTGGTTG GTGTCTGTGG GAGGCCTGCC CTTTTCTGAA GAGAAGTGGT    1228

GGGAGAGTGG ATGGGGTGGG GGCAGAGGAA AAGTGGGGGA GAGGGCCTGG GAGGAGAGGA    1288

GGGAGGGGGA CGGGGTGGGG GTGGGGAAAA CTATGGTTGG GATGTAAAAA CGGATAATAA    1348

TATAAATATT AAATAAAAAG AGAGTATTGA GCAAAAAAAA AAAAAAAAA                1398
```

(2) INFORMATION FOR SEQ ID NO:9:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO:9:

```
Met Ala Cys Asn Cys Gln Leu Met Gln Asp Thr Pro Leu Leu Lys Phe
 1               5                  10                  15

Pro Cys Pro Arg Leu Ile Leu Leu Phe Val Leu Leu Ile Arg Leu Ser
                20                  25                  30

Gln Val Ser Ser Ala Asp Phe Ser Thr Pro Asn Ile Thr Glu Ser Gly
            35                  40                  45

Asn Pro Ser Ala Asp Thr Lys Arg Ile Thr Cys Phe Ala Ser Gly Gly
    50                  55                  60

Phe Pro Lys Pro Arg Phe Ser Trp Leu Glu Asn Gly Arg Glu Leu Pro
65                  70                  75                  80

Gly Ile Asn Thr Thr Ile Ser Gln Asp Pro Glu Ser Glu Leu Tyr Thr
                85                  90                  95

Ile Ser Ser Gln Leu Asp Phe Asn Thr Thr Arg Asn His Thr Ile Lys
                100                 105                 110

Cys Leu Ile Lys Tyr Gly Asp Ala His Val Ser Glu Asp Phe Thr Trp
                115                 120                 125

Glu Lys Pro Pro Glu Asp Pro Pro Asp Ser Lys Asn Thr Leu Val Leu
130                 135                 140

Phe Gly Ala Gly Phe Gly Ala Val Ile Thr Val Val Ile Val Val Val
145                 150                 155                 160

Ile Ile Lys Cys Phe Cys Lys His Arg Ser Cys Phe Arg Arg Asn Glu
                165                 170                 175

Ala Ser Arg Glu Thr Asn Asn Ser Leu Thr Phe Gly Pro Glu Glu Ala
                180                 185                 190

Leu Ala Glu Gln Thr Val Phe Leu
            195                 200

(2) INFORMATION FOR SEQ ID NO:10:

(i) SEQUENCE CHARACTERISTICS:
        (A) LENGTH: 1570 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 249..890

(xi) SEQUENCE DESCRIPTION: SEQ ID NO:10:

GAGTTTTATA CCTCAATAGA CTCTTACTAG TTTCTCTTTT TCAGGTTGTG AAACTCAACC     60

TTCAAAGACA CTCTGTTCCA TTTCTGTGGA CTAATAGGAT CATCTTTAGC ATCTGCCGGG    120

TGGATGCCAT CCAGGCTTCT TTTTCTACAT CTCTGTTTCT CGATTTTTGT GAGCCTAGGA    180

GGTGCCTAAG CTCCATTGGC TCTAGATTCC TGGCTTTCCC CATCATGTTC TCCAAAGCAT    240

CTGAAGCT ATG GCT TGC AAT TGT CAG TTG ATG CAG GAT ACA CCA CTC CTC    290
         Met Ala Cys Asn Cys Gln Leu Met Gln Asp Thr Pro Leu Leu
          1               5                  10

AAG TTT CCA TGT CCA AGG CTC AAT CTT CTC TTT GTG CTG CTG ATT CGT    338
Lys Phe Pro Cys Pro Arg Leu Asn Leu Leu Phe Val Leu Leu Ile Arg
 15              20                  25                  30

CTT TCA CAA GTG TCT TCA GCT GAC TTC TCT ACC CCC AAC ATA ACT GAG    386
Leu Ser Gln Val Ser Ser Ala Asp Phe Ser Thr Pro Asn Ile Thr Glu
                35                  40                  45

TCT GGA AAC CCA TCT GCA GAC ACT AAA AGG ATT ACC TGC TTT GCT TCC    434
Ser Gly Asn Pro Ser Ala Asp Thr Lys Arg Ile Thr Cys Phe Ala Ser
            50                  55                  60
```

```
GGG GGT TTC CCA AAG CCT CGC TTC TCT TGG TTG GAA AAT GGA AGA GAA    482
Gly Gly Phe Pro Lys Pro Arg Phe Ser Trp Leu Glu Asn Gly Arg Glu
            65                  70                  75

TTA CCT GGC ATC AAT ACG ACA ATT TCC CAG GAT CCT GAA TCT GAA TTG    530
Leu Pro Gly Ile Asn Thr Thr Ile Ser Gln Asp Pro Glu Ser Glu Leu
        80                  85                  90

TAC ACC ATT AGT AGC CAA CTA GAT TTC AAT ACG ACT CGC AAC CAC ACC    578
Tyr Thr Ile Ser Ser Gln Leu Asp Phe Asn Thr Thr Arg Asn His Thr
 95                 100                 105                 110

ATT AAG TGT CTC ATT AAA TAT GGA GAT GCT CAC GTG TCA GAG GAC TTC    626
Ile Lys Cys Leu Ile Lys Tyr Gly Asp Ala His Val Ser Glu Asp Phe
                115                 120                 125

ACC TGG GAA AAA CCC CCA GAA GAC CCT CCT GAT AGC AAG AAC ACA CTT    674
Thr Trp Glu Lys Pro Pro Glu Asp Pro Pro Asp Ser Lys Asn Thr Leu
            130                 135                 140

GTG CTC TTT GGG GCA GGA TTC GGC GCA GTA ATA ACA GTC GTC GTC ATC    722
Val Leu Phe Gly Ala Gly Phe Gly Ala Val Ile Thr Val Val Val Ile
            145                 150                 155

GTT GTC ATC ATC AAA TGC TTC TGT AAG CAC GGT CTC ATC TAC CAT TTG    770
Val Val Ile Ile Lys Cys Phe Cys Lys His Gly Leu Ile Tyr His Leu
160                 165                 170

CAA CTG ACC TCT TCT GCA AAG GAC TTC AGA AAC CTA GCA CTA CCC TGG    818
Gln Leu Thr Ser Ser Ala Lys Asp Phe Arg Asn Leu Ala Leu Pro Trp
175                 180                 185                 190

CTC TGC AAA CAC GGT TCT CTA GGT GAA GCC TCT GCA GTG ATT TGC AGA    866
Leu Cys Lys His Gly Ser Leu Gly Glu Ala Ser Ala Val Ile Cys Arg
                195                 200                 205

AGT ACT CAG ACG AAT GAA CCA CAG TAGTTCTGCT GTTTCTGAGG ACGTAGTTTA   920
Ser Thr Gln Thr Asn Glu Pro Gln
                210

GAGACTGAAT TCTTTGGAAA GGACATAGGG ACAGTTTGCA CATTTGCTTG CACATCACAC   980

ACACACACAC ACACACACAC ACACACACAC ACACACACAC ACACACACAC ACACACACAC  1040

TCTCTCTCTC TCTCTCTCTC GATACCTTAG GATAGGGTTC TACCCTGTTG CTCAGTGACA  1100

AAGAATCACT CTGTGGCGGA GGCAGGCTTC AAGCTTGCAG CAATCCTCCT GCACCAGTTT  1160

CCTGAGTGCC AGACTTCCAG GTGTAAGCTA TGGCACTTAG CAGAACACTA GCTGAATCAA  1220

TGAAGACACT GAGGTTCCAA GAGGGAACCT GAATTATGAA GGTGAGTCAG AATCCAGATT  1280

TCCTGGCTCT ACCACTCTTA ACCTGTATCT GTTAGACCCC AAGCTCTGAG CTCATAGACA  1340

AGCTAATTTA AAATGCTTTT TAATAAGCAG AAGGCTCAGT TAGTACGGGG TTCAGGATAC  1400

TGCTTACTGG CAATATTTGA CTAGCCTCTA TTTTGTTTGT TTTTTAAAGG CCTACTGACT  1460

GTAGTGTAAT TTGTAGGAAA CATGTTGCTA TGTATACCCA TTTGAGGGTA ATAAAAATGT  1520

TGGTAATTTT CAGCCAGCAC TTTCCAGGTA TTTCCCTTTT TATCCTTCAT              1570

(2) INFORMATION FOR SEQ ID NO:11:

(i) SEQUENCE CHARACTERISTICS:
            (A) LENGTH: 214 amino acids
            (B) TYPE: amino acid
            (D) TOPOLOGY: linear (ii) MOLECULE TYPE: protein (xi) SEQUENCE DESCRIPTION: SEQ ID NO:11:

Met Ala Cys Asn Cys Gln Leu Met Gln Asp Thr Pro Leu Leu Lys Phe
  1               5                  10                  15

Pro Cys Pro Arg Leu Ile Leu Leu Phe Val Leu Leu Ile Arg Leu Ser
```

```
                    20                    25                      30
Gln Val Ser Ser Ala Asp Phe Ser Thr Pro Asn Ile Thr Glu Ser Gly
            35                      40                  45

Asn Pro Ser Ala Asp Thr Lys Arg Ile Thr Cys Phe Ala Ser Gly Gly
 50                      55                      60

Phe Pro Lys Pro Arg Phe Ser Trp Leu Glu Asn Gly Arg Glu Leu Pro
 65                  70                  75                  80

Gly Ile Asn Thr Thr Ile Ser Gln Asp Pro Glu Ser Glu Leu Tyr Thr
                    85                  90                  95

Ile Ser Ser Gln Leu Asp Phe Asn Thr Thr Arg Asn His Thr Ile Lys
                100                 105                 110

Cys Leu Ile Lys Tyr Gly Asp Ala His Val Ser Glu Asp Phe Thr Trp
            115                 120                 125

Glu Lys Pro Pro Glu Asp Pro Asp Ser Lys Asn Thr Leu Val Leu
        130                 135                 140

Phe Gly Ala Gly Phe Gly Ala Val Ile Thr Val Val Ile Val Val
145                 150                 155                 160

Ile Ile Lys Cys Phe Cys Lys His Gly Leu Ile Tyr His Leu Gln Leu
                165                 170                 175

Thr Ser Ser Ala Lys Asp Phe Arg Asn Leu Ala Leu Pro Trp Leu Cys
            180                 185                 190

Lys His Gly Ser Leu Gly Glu Ala Ser Ala Val Ile Cys Arg Ser Thr
            195                 200                 205

Gln Thr Asn Glu Pro Gln
    210
```

(2) INFORMATION FOR SEQ ID NO:12:

(i) SEQUENCE CHARACTERISTICS:
        (A) LENGTH: 1261 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 194..1135

(xi) SEQUENCE DESCRIPTION: SEQ ID NO:12:

```
AGNCCCNAGA TTATTTCTCC CTGTATAAGG GACGCCCAGG AGGCCTGGGG AGCGGACAAG      60

GCTCCTTTTA CTTTTCTTCT TCTTCTATTT TTTTTACCTT CTATTTTTTT CTTCATGTTC     120

CTGTGATCTT CGGGAATGCT GCTGTGCTTG TGTGTGTGGT CCCTGAGCGC CGAGGTGGAG     180

AGGCACTGGT GAC ATG TAT GTC ATC AAG ACA TGT GCA ACC TGC ACC ATG        229
            Met Tyr Val Ile Lys Thr Cys Ala Thr Cys Thr Met
              1               5                   10

GGC TTG GCA ATC CTT ATC TTT GTG ACA GTC TTG CTG ATC TCA GAT GCT       277
Gly Leu Ala Ile Leu Ile Phe Val Thr Val Leu Leu Ile Ser Asp Ala
            15                      20                  25

GTT TCC GTG GAG ACG CAA GCT TAT TTC AAT GGG ACT GCA TAT CTG CCG       325
Val Ser Val Glu Thr Gln Ala Tyr Phe Asn Gly Thr Ala Tyr Leu Pro
        30                      35                  40

TGC CCA TTT ACA AAG GCT CAA AAC ATA AGC CTG AGT GAG CTG GTA GTA       373
Cys Pro Phe Thr Lys Ala Gln Asn Ile Ser Leu Ser Glu Leu Val Val
 45                      50                  55                  60

TTT TGG CAG GAC CAG CAA AAG TTG GTT CTG TAC GAG CAC TAT TTG GGC       421
Phe Trp Gln Asp Gln Gln Lys Leu Val Leu Tyr Glu His Tyr Leu Gly
```

|  |  |  |  |  |  |  |  |  |  |  |  |  |  |  |  |
|---|---|---|---|---|---|---|---|---|---|---|---|---|---|---|---|
|  |  |  |  | 65 |  |  |  |  | 70 |  |  |  |  | 75 |  |

```
ACA GAG AAA CTT GAT AGT GTG AAT GCC AAG TAC CTG GGC CGC ACG AGC       469
Thr Glu Lys Leu Asp Ser Val Asn Ala Lys Tyr Leu Gly Arg Thr Ser
                80                  85                  90

TTT GAC AGG AAC AAC TGG ACT CTA CGA CTT CAC AAT GTT CAG ATC AAG       517
Phe Asp Arg Asn Asn Trp Thr Leu Arg Leu His Asn Val Gln Ile Lys
            95                 100                 105

GAC ATG GGC TCG TAT GAT TGT TTT ATA CAA AAA AAG CCA CCC ACA GGA       565
Asp Met Gly Ser Tyr Asp Cys Phe Ile Gln Lys Lys Pro Pro Thr Gly
        110                 115                 120

TCA ATT ATC CTC CAA CAG ACA TTA ACA GAA CTG TCA GTG ATC GCC AAC       613
Ser Ile Ile Leu Gln Gln Thr Leu Thr Glu Leu Ser Val Ile Ala Asn
125                 130                 135                 140

TTC AGT GAA CCT GAA ATA AAA CTG GCT CAG AAT GTA ACA GGA AAT TCT       661
Phe Ser Glu Pro Glu Ile Lys Leu Ala Gln Asn Val Thr Gly Asn Ser
                145                 150                 155

GGC ATA AAT TTG ACC TGC ACG TCT AAG CAA GGT CAC CCG AAA CCT AAG       709
Gly Ile Asn Leu Thr Cys Thr Ser Lys Gln Gly His Pro Lys Pro Lys
            160                 165                 170

AAG ATG TAT TTT CTG ATA ACT AAT TCA ACT AAT GAG TAT GGT GAT AAC       757
Lys Met Tyr Phe Leu Ile Thr Asn Ser Thr Asn Glu Tyr Gly Asp Asn
        175                 180                 185

ATG CAG ATA TCA CAA GAT AAT GTC ACA GAA CTG TTC AGT ATC TCC AAC       805
Met Gln Ile Ser Gln Asp Asn Val Thr Glu Leu Phe Ser Ile Ser Asn
190                 195                 200

AGC CTC TCT CTT TCA TTC CCG GAT GGT GTG TGG CAT ATG ACC GTT GTG       853
Ser Leu Ser Leu Ser Phe Pro Asp Gly Val Trp His Met Thr Val Val
205                 210                 215                 220

TGT GTT CTG GAA ACG GAG TCA ATG AAG ATT TCC TCC AAA CCT CTC AAT       901
Cys Val Leu Glu Thr Glu Ser Met Lys Ile Ser Ser Lys Pro Leu Asn
                225                 230                 235

TTC ACT CAA GAG TTT CCA TCT CCT CAA ACG TAT TGG AAG GAG ATT ACA       949
Phe Thr Gln Glu Phe Pro Ser Pro Gln Thr Tyr Trp Lys Glu Ile Thr
            240                 245                 250

GCT TCA GTT ACT GTG GCC CTC CTC CTT GTG ATG CTG CTC ATC ATT GTA       997
Ala Ser Val Thr Val Ala Leu Leu Leu Val Met Leu Leu Ile Ile Val
        255                 260                 265

TGT CAC AAG AAG CCG AAT CAG CCT AGC AGG CCC AGC AAC ACA GCC TCT      1045
Cys His Lys Lys Pro Asn Gln Pro Ser Arg Pro Ser Asn Thr Ala Ser
270                 275                 280

AAG TTA GAG CGG GAT AGT AAC GCT GAC AGA GAG ACT ATC AAC CTG AAG      1093
Lys Leu Glu Arg Asp Ser Asn Ala Asp Arg Glu Thr Ile Asn Leu Lys
285                 290                 295                 300

GAA CTT GAA CCC CAA ATT GCT TCA GCA AAA CCA AAT GCA GAG              1135
Glu Leu Glu Pro Gln Ile Ala Ser Ala Lys Pro Asn Ala Glu
                305                 310

TGAAGGCAGT GAGAGCCTGA GGAAAGAGTT AAAAATTGCT TGCCTGAAA TAAGAAGTGC     1195

AGAGTTTCTC AGAATTCAAA AATGTTCTCA GCTGATTGGA ATTCTACAGT TGAATAATTA    1255

AAGAAC                                                              1261
```

(2) INFORMATION FOR SEQ ID NO:13:

(i) SEQUENCE CHARACTERISTICS:
        (A) LENGTH: 314 amino acids
        (B) TYPE: amino acid
        (D) TOPOLOGY: linear (ii) MOLECULE TYPE: protein (xi) SEQUENCE DESCRIPTION: SEQ ID NO:13:

```
Met Tyr Val Ile Lys Thr Cys Ala Thr Cys Thr Met Gly Leu Ala Ile
 1               5                  10                  15

Leu Ile Phe Val Thr Val Leu Leu Ile Ser Asp Ala Val Ser Val Glu
                20                  25                  30

Thr Gln Ala Tyr Phe Asn Gly Thr Ala Tyr Leu Pro Cys Pro Phe Thr
            35                  40                  45

Lys Ala Gln Asn Ile Ser Leu Ser Glu Leu Val Val Phe Trp Gln Asp
        50                  55                  60

Gln Gln Lys Leu Val Leu Tyr Glu His Tyr Leu Gly Thr Glu Lys Leu
 65                  70                  75                  80

Asp Ser Val Asn Ala Lys Tyr Leu Gly Arg Thr Ser Phe Asp Arg Asn
                85                  90                  95

Asn Trp Thr Leu Arg Leu His Asn Val Gln Ile Lys Asp Met Gly Ser
                100                 105                 110

Tyr Asp Cys Phe Ile Gln Lys Lys Pro Pro Thr Gly Ser Ile Ile Leu
            115                 120                 125

Gln Gln Thr Leu Thr Glu Leu Ser Val Ile Ala Asn Phe Ser Glu Pro
130                 135                 140

Glu Ile Lys Leu Ala Gln Asn Val Thr Gly Asn Ser Gly Ile Asn Leu
145                 150                 155                 160

Thr Cys Thr Ser Lys Gln Gly His Pro Lys Pro Lys Lys Met Tyr Phe
                165                 170                 175

Leu Ile Thr Asn Ser Thr Asn Glu Tyr Gly Asp Asn Met Gln Ile Ser
            180                 185                 190

Gln Asp Asn Val Thr Glu Leu Phe Ser Ile Ser Asn Ser Leu Ser Leu
        195                 200                 205

Ser Phe Pro Asp Gly Val Trp His Met Thr Val Val Cys Val Leu Glu
    210                 215                 220

Thr Glu Ser Met Lys Ile Ser Ser Lys Pro Leu Asn Phe Thr Gln Glu
225                 230                 235                 240

Phe Pro Ser Pro Gln Thr Tyr Trp Lys Glu Ile Thr Ala Ser Val Thr
                245                 250                 255

Val Ala Leu Leu Leu Val Met Leu Leu Ile Ile Val Cys His Lys Lys
            260                 265                 270

Pro Asn Gln Pro Ser Arg Pro Ser Asn Thr Ala Ser Lys Leu Glu Arg
        275                 280                 285

Asp Ser Asn Ala Asp Arg Glu Thr Ile Asn Leu Lys Glu Leu Glu Pro
    290                 295                 300

Gln Ile Ala Ser Ala Lys Pro Asn Ala Glu
305                 310
```

(2) INFORMATION FOR SEQ ID NO:14:

(i) SEQUENCE CHARACTERISTICS:
        (A) LENGTH: 223 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 194..223

(xi) SEQUENCE DESCRIPTION: SEQ ID NO:14:

AGNCCCNAGA TTATTTCTCC CTGTATAAGG GACGCCCAGG AGGCCTGGGG AGCGGACAAG    60

```
GCTCCTTTTA CTTTTCTTCT TCTTCTATTT TTTTTACCTT CTATTTTTTT CTTCATGTTC        120

CTGTGATCTT CGGGAATGCT GCTGTGCTTG TGTGTGTGGT CCCTGAGCGC CGAGGTGGAG        180

AGGCACTGGT GAC ATG TAT GTC ATC AAG ACA TGT GCA ACC TGC                   223
            Met Tyr Val Ile Lys Thr Cys Ala Thr Cys
              1               5                  10
```

(2) INFORMATION FOR SEQ ID NO:15:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:15:

```
Met Tyr Val Ile Lys Thr Cys Ala Thr Cys
  1               5                  10
```

(2) INFORMATION FOR SEQ ID NO:16:

(i) SEQUENCE CHARACTERISTICS:
        (A) LENGTH: 1716 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 249..1166

(xi) SEQUENCE DESCRIPTION: SEQ ID NO:16:

```
GAGTTTTATA CCTCAATAGA CTCTTACTAG TTTCTCTTTT TCAGGTTGTG AAACTCAACC         60

TTCAAAGACA CTCTGTTCCA TTTCTGTGGA CTAATAGGAT CATCTTTAGC ATCTGCCGGG        120

TGGATGCCAT CCAGGCTTCT TTTTCTACAT CTCTGTTTCT CGATTTTTGT GAGCCTAGGA        180

GGTGCCTAAG CTCCATTGGC TCTAGATTCC TGGCTTTCCC CATCATGTTC TCCAAAGCAT        240

CTGAAGCT ATG GCT TGC AAT TGT CAG TTG ATG CAG GAT ACA CCA CTC CTC         290
         Met Ala Cys Asn Cys Gln Leu Met Gln Asp Thr Pro Leu Leu
           1               5                  10

AAG TTT CCA TGT CCA AGG CTC AAT CTT CTC TTT GTG CTG CTG ATT CGT         338
Lys Phe Pro Cys Pro Arg Leu Asn Leu Leu Phe Val Leu Leu Ile Arg
 15                  20                  25                  30

CTT TCA CAA GTG TCT TCA GAT GTT GAT GAA CAA CTG TCC AAG TCA GTG         386
Leu Ser Gln Val Ser Ser Asp Val Asp Glu Gln Leu Ser Lys Ser Val
                 35                  40                  45

AAA GAT AAG GTA TTG CTG CCT TGC CGT TAC AAC TCT CCT CAT GAA GAT         434
Lys Asp Lys Val Leu Leu Pro Cys Arg Tyr Asn Ser Pro His Glu Asp
             50                  55                  60

GAG TCT GAA GAC CGA ATC TAC TGG CAA AAA CAT GAC AAA GTG GTG CTG         482
Glu Ser Glu Asp Arg Ile Tyr Trp Gln Lys His Asp Lys Val Val Leu
         65                  70                  75

TCT GTC ATT GCT GGG AAA CTA AAA GTG TGG CCC GAG TAT AAG AAC CGG         530
Ser Val Ile Ala Gly Lys Leu Lys Val Trp Pro Glu Tyr Lys Asn Arg
     80                  85                  90

ACT TTA TAT GAC AAC ACT ACC TAC TCT CTT ATC ATC CTG GGC CTG GTC         578
Thr Leu Tyr Asp Asn Thr Thr Tyr Ser Leu Ile Ile Leu Gly Leu Val
 95                 100                 105                 110

CTT TCA GAC CGG GGC ACA TAC AGC TGT GTC GTT CAA AAG AAG GAA AGA         626
Leu Ser Asp Arg Gly Thr Tyr Ser Cys Val Val Gln Lys Lys Glu Arg
```

|  |  |  |  |  |  |  |  |  |  | 115 |  |  |  |  | 120 |  |  |  |  | 125 |  |  |  |  |
|---|---|---|---|---|---|---|---|---|---|---|---|---|---|---|---|---|---|---|---|---|---|---|---|---|---|

```
GGA ACG TAT GAA GTT AAA CAC TTG GCT TTA GTA AAG TTG TCC ATC AAA      674
Gly Thr Tyr Glu Val Lys His Leu Ala Leu Val Lys Leu Ser Ile Lys
            130                 135                 140

GCT GAC TTC TCT ACC CCC AAC ATA ACT GAG TCT GGA AAC CCA TCT GCA      722
Ala Asp Phe Ser Thr Pro Asn Ile Thr Glu Ser Gly Asn Pro Ser Ala
            145                 150                 155

GAC ACT AAA AGG ATT ACC TGC TTT GCT TCC GGG GGT TTC CCA AAG CCT      770
Asp Thr Lys Arg Ile Thr Cys Phe Ala Ser Gly Gly Phe Pro Lys Pro
        160                 165                 170

CGC TTC TCT TGG TTG GAA AAT GGA AGA GAA TTA CCT GGC ATC AAT ACG      818
Arg Phe Ser Trp Leu Glu Asn Gly Arg Glu Leu Pro Gly Ile Asn Thr
175                 180                 185                 190

ACA ATT TCC CAG GAT CCT GAA TCT GAA TTG TAC ACC ATT AGT AGC CAA      866
Thr Ile Ser Gln Asp Pro Glu Ser Glu Leu Tyr Thr Ile Ser Ser Gln
                195                 200                 205

CTA GAT TTC AAT ACG ACT CGC AAC CAC ACC ATT AAG TGT CTC ATT AAA      914
Leu Asp Phe Asn Thr Thr Arg Asn His Thr Ile Lys Cys Leu Ile Lys
            210                 215                 220

TAT GGA GAT GCT CAC GTG TCA GAG GAC TTC ACC TGG GAA AAA CCC CCA      962
Tyr Gly Asp Ala His Val Ser Glu Asp Phe Thr Trp Glu Lys Pro Pro
            225                 230                 235

GAA GAC CCT CCT GAT AGC AAG AAC ACA CTT GTG CTC TTT GGG GCA GGA     1010
Glu Asp Pro Pro Asp Ser Lys Asn Thr Leu Val Leu Phe Gly Ala Gly
        240                 245                 250

TTC GGC GCA GTA ATA ACA GTC GTC GTC ATC GTT GTC ATC ATC AAA TGC     1058
Phe Gly Ala Val Ile Thr Val Val Val Ile Val Val Ile Ile Lys Cys
255                 260                 265                 270

TTC TGT AAG CAC AGA AGC TGT TTC AGA AGA AAT GAG GCA AGC AGA GAA     1106
Phe Cys Lys His Arg Ser Cys Phe Arg Arg Asn Glu Ala Ser Arg Glu
                275                 280                 285

ACA AAC AAC AGC CTT ACC TTC GGG CCT GAA GAA GCA TTA GCT GAA CAG     1154
Thr Asn Asn Ser Leu Thr Phe Gly Pro Glu Glu Ala Leu Ala Glu Gln
            290                 295                 300

ACC GTC TTC CTT TAGTTCTTCT CTGTCCATGT GGGATACATG GTATTATGTG         1206
Thr Val Phe Leu
            305

GCTCATGAGG TACAATCTTT CTTTCAGCAC CGTGCTAGCT GATCTTTCGG ACAACTTGAC   1266

ACAAGATAGA GTTAACTGGG AAGAGAAAGC CTTGAATGAG GATTTCTTTC CATCAGGAAG   1326

CTACGGGCAA GTTTGCTGGG CCTTTGATTG CTTGATGACT GAAGTGGAAA GGCTGAGCCC   1386

ACTGTGGGTG GTGCTAGCCC TGGGCAGGGG CAGGTGACCC TGGGTGGTAT AAGAAAAAGA   1446

GCTGTCACTA AAAGGAGAGG TGCCTAGTCT TACTGCAACT TGATATGTCA TGTTTGGTTG   1506

GTGTCTGTGG GAGGCCTGCC CTTTTCTGAA GAGAAGTGGT GGGAGAGTGG ATGGGGTGGG   1566

GGCAGAGGAA AAGTGGGGGA GAGGGCCTGG GAGGAGAGGA GGGAGGGGGA CGGGGTGGGG   1626

GTGGGGAAAA CTATGGTTGG GATGTAAAAA CGGATAATAA TATAAATATT AAATAAAAAG   1686

AGAGTATTGA GCAAAAAAAA AAAAAAAAA                                    1716
```

(2) INFORMATION FOR SEQ ID NO:17:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:17:

```
Met Ala Cys Asn Cys Gln Leu Met Gln Asp Thr Pro Leu Leu Lys Phe
 1               5                  10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
 65                 70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
    275                 280                 285

Asn Ser Leu Thr Phe Gly Pro Glu Glu Ala Leu Ala Glu Gln Thr Val
    290                 295                 300

Phe Leu
305

(2) INFORMATION FOR SEQ ID NO:18:

(i) SEQUENCE CHARACTERISTICS:
        (A) LENGTH: 1491 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 318..1181

(xi) SEQUENCE DESCRIPTION: SEQ ID NO:18:

CCAAAGAAAA AGTGATTTGT CATTGCTTTA TAGACTGTAA GAAGAGAACA TCTCAGAAGT      60
```

```
GGAGTCTTAC CCTGAAATCA AAGGATTTAA AGAAAAAGTG GAATTTTTCT TCAGCAAGCT        120

GTGAAACTAA ATCCACAACC TTTGGAGACC CAGGAACACC CTCCAATCTC TGTGTGTTTT        180

GTAAACATCA CTGGAGGGTC TTCTACGTGA GCAATTGGAT TGTCATCAGC CCTGCCTGTT        240

TTGCACCTGG GAAGTGCCCT GGTCTTACTT GGGTCCAAAT TGTTGGCTTT CACTTTTGAC        300

CCTAAGCATC TGAAGCC ATG GGC CAC ACA CGG AGG CAG GGA ACA TCA CCA           350
                   Met Gly His Thr Arg Arg Gln Gly Thr Ser Pro
                    1               5                       10

TCC AAG TGT CCA TAC CTG AAT TTC TTT CAG CTC TTG GTG CTG GCT GGT          398
Ser Lys Cys Pro Tyr Leu Asn Phe Phe Gln Leu Leu Val Leu Ala Gly
         15                  20                  25

CTT TCT CAC TTC TGT TCA GGT GTT ATC CAC GTG ACC AAG GAA GTG AAA          446
Leu Ser His Phe Cys Ser Gly Val Ile His Val Thr Lys Glu Val Lys
         30                  35                  40

GAA GTG GCA ACG CTG TCC TGT GGT CAC AAT GTT TCT GTT GAA GAG CTG          494
Glu Val Ala Thr Leu Ser Cys Gly His Asn Val Ser Val Glu Glu Leu
     45                  50                  55

GCA CAA ACT CGC ATC TAC TGG CAA AAG GAG AAG AAA ATG GTG CTG ACT          542
Ala Gln Thr Arg Ile Tyr Trp Gln Lys Glu Lys Lys Met Val Leu Thr
 60                  65                  70                  75

ATG ATG TCT GGG GAC ATG AAT ATA TGG CCC GAG TAC AAG AAC CGG ACC          590
Met Met Ser Gly Asp Met Asn Ile Trp Pro Glu Tyr Lys Asn Arg Thr
                 80                  85                  90

ATC TTT GAT ATC ACT AAT AAC CTC TCC ATT GTG ATC CTG GCT CTG CGC          638
Ile Phe Asp Ile Thr Asn Asn Leu Ser Ile Val Ile Leu Ala Leu Arg
                 95                 100                 105

CCA TCT GAC GAG GGC ACA TAC GAG TGT GTT GTT CTG AAG TAT GAA AAA          686
Pro Ser Asp Glu Gly Thr Tyr Glu Cys Val Val Leu Lys Tyr Glu Lys
             110                 115                 120

GAC GCT TTC AAG CGG GAA CAC CTG GCT GAA GTG ACG TTA TCA GTC AAA          734
Asp Ala Phe Lys Arg Glu His Leu Ala Glu Val Thr Leu Ser Val Lys
         125                 130                 135

GCT GAC TTC CCT ACA CCT AGT ATA TCT GAC TTT GAA ATT CCA ACT TCT          782
Ala Asp Phe Pro Thr Pro Ser Ile Ser Asp Phe Glu Ile Pro Thr Ser
140                 145                 150                 155

AAT ATT AGA AGG ATA ATT TGC TCA ACC TCT GGA GGT TTT CCA GAG CCT          830
Asn Ile Arg Arg Ile Ile Cys Ser Thr Ser Gly Gly Phe Pro Glu Pro
                 160                 165                 170

CAC CTC TCC TGG TTG GAA AAT GGA GAA GAA TTA AAT GCC ATC AAC ACA          878
His Leu Ser Trp Leu Glu Asn Gly Glu Glu Leu Asn Ala Ile Asn Thr
                 175                 180                 185

ACA GTT TCC CAA GAT CCT GAA ACT GAG CTC TAT GCT GTT AGC AGC AAA          926
Thr Val Ser Gln Asp Pro Glu Thr Glu Leu Tyr Ala Val Ser Ser Lys
             190                 195                 200

CTG GAT TTC AAT ATG ACA ACC AAC CAC AGC TTC ATG TGT CTC ATC AAG          974
Leu Asp Phe Asn Met Thr Thr Asn His Ser Phe Met Cys Leu Ile Lys
         205                 210                 215

TAT GGA CAT TTA AGA GTG AAT CAG ACC TTC AAC TGG AAT ACA ACC AAG         1022
Tyr Gly His Leu Arg Val Asn Gln Thr Phe Asn Trp Asn Thr Thr Lys
220                 225                 230                 235

CAA GAG CAT TTT CCT GAT AAC CTG CTC CCA TCC TGG GCC ATT ACC TTA         1070
Gln Glu His Phe Pro Asp Asn Leu Leu Pro Ser Trp Ala Ile Thr Leu
                 240                 245                 250

ATC TCA GTA AAT GGA ATT TTT GTG ATA TGC TGC CTG ACC TAC TGC TTT         1118
Ile Ser Val Asn Gly Ile Phe Val Ile Cys Cys Leu Thr Tyr Cys Phe
                 255                 260                 265

GCC CCA AGA TGC AGA GAG AGA AGG AGG AAT GAG AGA TTG AGA AGG GAA         1166
Ala Pro Arg Cys Arg Glu Arg Arg Arg Asn Glu Arg Leu Arg Arg Glu
```

```
                    270                 275                 280
AGT GTA CGC CCT GTA TAACAGTGTC CGCAGAAGCA AGGGGCTGAA AAGATCTGAA     1221
Ser Val Arg Pro Val
        285

GGTAGCCTCC GTCATCTCTT CTGGGATACA TGGATCGTGG GGATCATGAG GCATTCTTCC   1281

CTTAACAAAT TTAAGCTGTT TTACCCACTA CCTCACCTTC TTAAAAACCT CTTTCAGATT   1341

AAGCTGAACA GTTACAAGAT GGCTGGCATC CCTCTCCTTT CTCCCCATAT GCAATTTGCT   1401

TAATGTAACC TCTTCTTTTG CCATGTTTCC ATTCTGCCAT CTTGAATTGT CTTGTCAGCC   1461

AATTCATTAT CTATTAAACA CTAATTTGAG                                    1491

(2) INFORMATION FOR SEQ ID NO:19:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO:19:

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
        50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
        210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270
```

```
Glu Arg Arg Arg Asn Glu Arg Leu Arg Glu Ser Val Arg Pro Val
        275                 280                 285
```

(2) INFORMATION FOR SEQ ID NO:20:

(i) SEQUENCE CHARACTERISTICS:
        (A) LENGTH: 1151 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 99..1025

(xi) SEQUENCE DESCRIPTION: SEQ ID NO:20:

```
GGAGCAAGCA GACGCGTAAG AGTGGCTCCT GTAGGCAGCA CGGACTTGAA CAACCAGACT     60

CCTGTAGACG TGTTCCAGAA CTTACGGAAG CACCCACG ATG GAC CCC AGA TGC        113
                                         Met Asp Pro Arg Cys
                                          1               5

ACC ATG GGC TTG GCA ATC CTT ATC TTT GTG ACA GTC TTG CTG ATC TCA     161
Thr Met Gly Leu Ala Ile Leu Ile Phe Val Thr Val Leu Leu Ile Ser
             10                  15                  20

GAT GCT GTT TCC GTG GAG ACG CAA GCT TAT TTC AAT GGG ACT GCA TAT     209
Asp Ala Val Ser Val Glu Thr Gln Ala Tyr Phe Asn Gly Thr Ala Tyr
         25                  30                  35

CTG CCG TGC CCA TTT ACA AAG GCT CAA AAC ATA AGC CTG AGT GAG CTG     257
Leu Pro Cys Pro Phe Thr Lys Ala Gln Asn Ile Ser Leu Ser Glu Leu
     40                  45                  50

GTA GTA TTT TGG CAG GAC CAG CAA AAG TTG GTT CTG TAC GAG CAC TAT     305
Val Val Phe Trp Gln Asp Gln Gln Lys Leu Val Leu Tyr Glu His Tyr
 55                  60                  65

TTG GGC ACA GAG AAA CTT GAT AGT GTG AAT GCC AAG TAC CTG GGC CGC     353
Leu Gly Thr Glu Lys Leu Asp Ser Val Asn Ala Lys Tyr Leu Gly Arg
 70                  75                  80                  85

ACG AGC TTT GAC AGG AAC AAC TGG ACT CTA CGA CTT CAC AAT GTT CAG     401
Thr Ser Phe Asp Arg Asn Asn Trp Thr Leu Arg Leu His Asn Val Gln
                 90                  95                 100

ATC AAG GAC ATG GGC TCG TAT GAT TGT TTT ATA CAA AAA AAG CCA CCC     449
Ile Lys Asp Met Gly Ser Tyr Asp Cys Phe Ile Gln Lys Lys Pro Pro
            105                 110                 115

ACA GGA TCA ATT ATC CTC CAA CAG ACA TTA ACA GAA CTG TCA GTG ATC     497
Thr Gly Ser Ile Ile Leu Gln Gln Thr Leu Thr Glu Leu Ser Val Ile
        120                 125                 130

GCC AAC TTC AGT GAA CCT GAA ATA AAA CTG GCT CAG AAT GTA ACA GGA     545
Ala Asn Phe Ser Glu Pro Glu Ile Lys Leu Ala Gln Asn Val Thr Gly
    135                 140                 145

AAT TCT GGC ATA AAT TTG ACC TGC ACG TCT AAG CAA GGT CAC CCG AAA     593
Asn Ser Gly Ile Asn Leu Thr Cys Thr Ser Lys Gln Gly His Pro Lys
150                 155                 160                 165

CCT AAG AAG ATG TAT TTT CTG ATA ACT AAT TCA ACT AAT GAG TAT GGT     641
Pro Lys Lys Met Tyr Phe Leu Ile Thr Asn Ser Thr Asn Glu Tyr Gly
                170                 175                 180

GAT AAC ATG CAG ATA TCA CAA GAT AAT GTC ACA GAA CTG TTC AGT ATC     689
Asp Asn Met Gln Ile Ser Gln Asp Asn Val Thr Glu Leu Phe Ser Ile
            185                 190                 195

TCC AAC AGC CTC TCT CTT TCA TTC CCG GAT GGT GTG TGG CAT ATG ACC     737
Ser Asn Ser Leu Ser Leu Ser Phe Pro Asp Gly Val Trp His Met Thr
        200                 205                 210

GTT GTG TGT GTT CTG GAA ACG GAG TCA ATG AAG ATT TCC TCC AAA CCT     785
```

```
Val Val Cys Val Leu Glu Thr Glu Ser Met Lys Ile Ser Ser Lys Pro
    215                 220                 225

CTC AAT TTC ACT CAA GAG TTT CCA TCT CCT CAA ACG TAT TGG AAG GAG        833
Leu Asn Phe Thr Gln Glu Phe Pro Ser Pro Gln Thr Tyr Trp Lys Glu
230                 235                 240                 245

ATT ACA GCT TCA GTT ACT GTG GCC CTC CTC CTT GTG ATG CTG CTC ATC        881
Ile Thr Ala Ser Val Thr Val Ala Leu Leu Leu Val Met Leu Leu Ile
                250                 255                 260

ATT GTA TGT CAC AAG AAG CCG AAT CAG CCT AGC AGG CCC AGC AAC ACA        929
Ile Val Cys His Lys Lys Pro Asn Gln Pro Ser Arg Pro Ser Asn Thr
            265                 270                 275

GCC TCT AAG TTA GAG CGG GAT AGT AAC GCT GAC AGA GAG ACT ATC AAC        977
Ala Ser Lys Leu Glu Arg Asp Ser Asn Ala Asp Arg Glu Thr Ile Asn
        280                 285                 290

CTG AAG GAA CTT GAA CCC CAA ATT GCT TCA GCA AAA CCA AAT GCA GAG       1025
Leu Lys Glu Leu Glu Pro Gln Ile Ala Ser Ala Lys Pro Asn Ala Glu
    295                 300                 305

TGAAGGCAGT GAGAGCCTGA GGAAAGAGTT AAAAATTGCT TTGCCTGAAA TAAGAAGTGC     1085

AGAGTTTCTC AGAATTCAAA AATGTTCTCA GCTGATTGGA ATTCTACAGT TGAATAATTA     1145

AAGAAC                                                                1151

(2) INFORMATION FOR SEQ ID NO:21:

(i) SEQUENCE CHARACTERISTICS:
        (A) LENGTH: 309 amino acids
        (B) TYPE: amino acid
        (D) TOPOLOGY: linear (ii) MOLECULE TYPE: protein (xi) SEQUENCE DESCRIPTION: SEQ ID NO:21:

Met Asp Pro Arg Cys Thr Met Gly Leu Ala Ile Leu Ile Phe Val Thr
1               5                   10                  15

Val Leu Leu Ile Ser Asp Ala Val Ser Val Glu Thr Gln Ala Tyr Phe
                20                  25                  30

Asn Gly Thr Ala Tyr Leu Pro Cys Pro Phe Thr Lys Ala Gln Asn Ile
            35                  40                  45

Ser Leu Ser Glu Leu Val Val Phe Trp Gln Asp Gln Gln Lys Leu Val
        50                  55                  60

Leu Tyr Glu His Tyr Leu Gly Thr Glu Lys Leu Asp Ser Val Asn Ala
65                  70                  75                  80

Lys Tyr Leu Gly Arg Thr Ser Phe Asp Arg Asn Asn Trp Thr Leu Arg
                85                  90                  95

Leu His Asn Val Gln Ile Lys Asp Met Gly Ser Tyr Asp Cys Phe Ile
            100                 105                 110

Gln Lys Lys Pro Pro Thr Gly Ser Ile Ile Leu Gln Gln Thr Leu Thr
        115                 120                 125

Glu Leu Ser Val Ile Ala Asn Phe Ser Glu Pro Glu Ile Lys Leu Ala
130                 135                 140

Gln Asn Val Thr Gly Asn Ser Gly Ile Asn Leu Thr Cys Thr Ser Lys
145                 150                 155                 160

Gln Gly His Pro Lys Pro Lys Lys Met Tyr Phe Leu Ile Thr Asn Ser
                165                 170                 175

Thr Asn Glu Tyr Gly Asp Asn Met Gln Ile Ser Gln Asp Asn Val Thr
            180                 185                 190

Glu Leu Phe Ser Ile Ser Asn Ser Leu Ser Leu Ser Phe Pro Asp Gly
        195                 200                 205
```

```
Val Trp His Met Thr Val Val Cys Val Leu Glu Thr Glu Ser Met Lys
    210                 215                 220

Ile Ser Ser Lys Pro Leu Asn Phe Thr Gln Glu Phe Pro Ser Pro Gln
225                 230                 235                 240

Thr Tyr Trp Lys Glu Ile Thr Ala Ser Val Thr Val Ala Leu Leu Leu
                245                 250                 255

Val Met Leu Leu Ile Ile Val Cys His Lys Lys Pro Asn Gln Pro Ser
            260                 265                 270

Arg Pro Ser Asn Thr Ala Ser Lys Leu Glu Arg Asp Ser Asn Ala Asp
        275                 280                 285

Arg Glu Thr Ile Asn Leu Lys Glu Leu Glu Pro Gln Ile Ala Ser Ala
    290                 295                 300

Lys Pro Asn Ala Glu
305

(2) INFORMATION FOR SEQ ID NO:22:

(i) SEQUENCE CHARACTERISTICS:
        (A) LENGTH: 1120 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 107..1093

(xi) SEQUENCE DESCRIPTION: SEQ ID NO:22:

CACAGGGTGA AAGCTTTGCT TCTCTGCTGC TGTAACAGGG ACTAGCACAG ACACACGGAT      60

GAGTGGGGTC ATTTCCAGAT ATTAGGTCAC AGCAGAAGCA GCCAAA ATG GAT CCC        115
                                              Met Asp Pro
                                                1

CAG TGC ACT ATG GGA CTG AGT AAC ATT CTC TTT GTG ATG GCC TTC CTG       163
Gln Cys Thr Met Gly Leu Ser Asn Ile Leu Phe Val Met Ala Phe Leu
     5                  10                  15

CTC TCT GGT GCT GCT CCT CTG AAG ATT CAA GCT TAT TTC AAT GAG ACT       211
Leu Ser Gly Ala Ala Pro Leu Lys Ile Gln Ala Tyr Phe Asn Glu Thr
 20                  25                  30                  35

GCA GAC CTG CCA TGC CAA TTT GCA AAC TCT CAA AAC CAA AGC CTG AGT       259
Ala Asp Leu Pro Cys Gln Phe Ala Asn Ser Gln Asn Gln Ser Leu Ser
                40                  45                  50

GAG CTA GTA GTA TTT TGG CAG GAC CAG GAA AAC TTG GTT CTG AAT GAG       307
Glu Leu Val Val Phe Trp Gln Asp Gln Glu Asn Leu Val Leu Asn Glu
             55                  60                  65

GTA TAC TTA GGC AAA GAG AAA TTT GAC AGT GTT CAT TCC AAG TAT ATG       355
Val Tyr Leu Gly Lys Glu Lys Phe Asp Ser Val His Ser Lys Tyr Met
         70                  75                  80

GGC CGC ACA AGT TTT GAT TCG GAC AGT TGG ACC CTG AGA CTT CAC AAT       403
Gly Arg Thr Ser Phe Asp Ser Asp Ser Trp Thr Leu Arg Leu His Asn
     85                  90                  95

CTT CAG ATC AAG GAC AAG GGC TTG TAT CAA TGT ATC ATC CAT CAC AAA       451
Leu Gln Ile Lys Asp Lys Gly Leu Tyr Gln Cys Ile Ile His His Lys
100                 105                 110                 115

AAG CCC ACA GGA ATG ATT CGC ATC CAC CAG ATG AAT TCT GAA CTG TCA       499
Lys Pro Thr Gly Met Ile Arg Ile His Gln Met Asn Ser Glu Leu Ser
                120                 125                 130

GTG CTT GCT AAC TTC AGT CAA CCT GAA ATA GTA CCA ATT TCT AAT ATA       547
Val Leu Ala Asn Phe Ser Gln Pro Glu Ile Val Pro Ile Ser Asn Ile
```

-continued

```
                    135                 140                 145
ACA GAA AAT GTG TAC ATA AAT TTG ACC TGC TCA TCT ATA CAC GGT TAC        595
Thr Glu Asn Val Tyr Ile Asn Leu Thr Cys Ser Ser Ile His Gly Tyr
            150                 155                 160

CCA GAA CCT AAG AAG ATG AGT GTT TTG CTA AGA ACC AAG AAT TCA ACT        643
Pro Glu Pro Lys Lys Met Ser Val Leu Leu Arg Thr Lys Asn Ser Thr
        165                 170                 175

ATC GAG TAT GAT GGT ATT ATG CAG AAA TCT CAA GAT AAT GTC ACA GAA        691
Ile Glu Tyr Asp Gly Ile Met Gln Lys Ser Gln Asp Asn Val Thr Glu
180                 185                 190                 195

CTG TAC GAC GTT TCC ATC AGC TTG TCT GTT TCA TTC CCT GAT GTT ACG        739
Leu Tyr Asp Val Ser Ile Ser Leu Ser Val Ser Phe Pro Asp Val Thr
                200                 205                 210

AGC AAT ATG ACC ATC TTC TGT ATT CTG GAA ACT GAC AAG ACG CGG CTT        787
Ser Asn Met Thr Ile Phe Cys Ile Leu Glu Thr Asp Lys Thr Arg Leu
            215                 220                 225

TTA TCT TCA CCT TTC TCT ATA GAG CTT GAG GAC CCT CAG CCT CCC CCA        835
Leu Ser Ser Pro Phe Ser Ile Glu Leu Glu Asp Pro Gln Pro Pro Pro
        230                 235                 240

GAC CAC ATT CCT TGG ATT ACA GCT GTA CTT CCA ACA GTT ATT ATA TGT        883
Asp His Ile Pro Trp Ile Thr Ala Val Leu Pro Thr Val Ile Ile Cys
    245                 250                 255

GTG ATG GTT TTC TGT CTA ATT CTA TGG AAA TGG AAG AAG AAG AAG CGG        931
Val Met Val Phe Cys Leu Ile Leu Trp Lys Trp Lys Lys Lys Lys Arg
260                 265                 270                 275

CCT CGC AAC TCT TAT AAA TGT GGA ACC AAC ACA ATG GAG AGG GAA GAG        979
Pro Arg Asn Ser Tyr Lys Cys Gly Thr Asn Thr Met Glu Arg Glu Glu
                280                 285                 290

AGT GAA CAG ACC AAG AAA AGA GAA AAA ATC CAT ATA CCT GAA AGA TCT       1027
Ser Glu Gln Thr Lys Lys Arg Glu Lys Ile His Ile Pro Glu Arg Ser
            295                 300                 305

GAT GAA GCC CAG CGT GTT TTT AAA AGT TCG AAG ACA TCT TCA TGC GAC       1075
Asp Glu Ala Gln Arg Val Phe Lys Ser Ser Lys Thr Ser Ser Cys Asp
        310                 315                 320

AAA AGT GAT ACA TGT TTT TAATTAAAGA GTAAAGCCCA AAAAAA                  1120
Lys Ser Asp Thr Cys Phe
    325
```

(2) INFORMATION FOR SEQ ID NO:23:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:23:

```
Met Asp Pro Gln Cys Thr Met Gly Leu Ser Asn Ile Leu Phe Val Met
1               5                  10                  15

Ala Phe Leu Leu Ser Gly Ala Ala Pro Leu Lys Ile Gln Ala Tyr Phe
                20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Gln Glu Asn Leu Val
        50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95
```

```
Leu His Asn Leu Gln Ile Lys Asp Lys Gly Leu Tyr Gln Cys Ile Ile
            100                 105                 110
His His Lys Lys Pro Thr Gly Met Ile Arg Ile His Gln Met Asn Ser
            115                 120                 125
Glu Leu Ser Val Leu Ala Asn Phe Ser Gln Pro Glu Ile Val Pro Ile
            130                 135                 140
Ser Asn Ile Thr Glu Asn Val Tyr Ile Asn Leu Thr Cys Ser Ser Ile
145                 150                 155                 160
His Gly Tyr Pro Glu Pro Lys Lys Met Ser Val Leu Leu Arg Thr Lys
                    165                 170                 175
Asn Ser Thr Ile Glu Tyr Asp Gly Ile Met Gln Lys Ser Gln Asp Asn
            180                 185                 190
Val Thr Glu Leu Tyr Asp Val Ser Ile Ser Leu Ser Val Ser Phe Pro
            195                 200                 205
Asp Val Thr Ser Asn Met Thr Ile Phe Cys Ile Leu Glu Thr Asp Lys
            210                 215                 220
Thr Arg Leu Leu Ser Ser Pro Phe Ser Ile Glu Leu Glu Asp Pro Gln
225                 230                 235                 240
Pro Pro Pro Asp His Ile Pro Trp Ile Thr Ala Val Leu Pro Thr Val
                    245                 250                 255
Ile Ile Cys Val Met Val Phe Cys Leu Ile Leu Trp Lys Trp Lys Lys
            260                 265                 270
Lys Lys Arg Pro Arg Asn Ser Tyr Lys Cys Gly Thr Asn Thr Met Glu
            275                 280                 285
Arg Glu Glu Ser Glu Gln Thr Lys Lys Arg Glu Lys Ile His Ile Pro
            290                 295                 300
Glu Arg Ser Asp Glu Ala Gln Arg Val Phe Lys Ser Ser Lys Thr Ser
305                 310                 315                 320
Ser Cys Asp Lys Ser Asp Thr Cys Phe
                    325

(2) INFORMATION FOR SEQ ID NO:24:

(i) SEQUENCE CHARACTERISTICS:
        (A) LENGTH: 1161 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 148..1134

(xi) SEQUENCE DESCRIPTION: SEQ ID NO:24:

AGGAGCCTTA GGAGGTACGG GGAGCTCGCA AATACTCCTT TTGGTTTATT CTTACCACCT      60

TGCTTCTGTG TTCCTTGGGA ATGCTGCTGT GCTTATGCAT CTGGTCTCTT TTTGGAGCTA     120

CAGTGGACAG GCATTTGTGA CAGCACT ATG GAT CCC CAG TGC ACT ATG GGA         171
                               Met Asp Pro Gln Cys Thr Met Gly
                                 1               5

CTG AGT AAC ATT CTC TTT GTG ATG GCC TTC CTG CTC TCT GGT GCT GCT       219
Leu Ser Asn Ile Leu Phe Val Met Ala Phe Leu Leu Ser Gly Ala Ala
     10                  15                  20

CCT CTG AAG ATT CAA GCT TAT TTC AAT GAG ACT GCA GAC CTG CCA TGC       267
Pro Leu Lys Ile Gln Ala Tyr Phe Asn Glu Thr Ala Asp Leu Pro Cys
 25                  30                  35                  40
```

```
CAA TTT GCA AAC TCT CAA AAC CAA AGC CTG AGT GAG CTA GTA GTA TTT        315
Gln Phe Ala Asn Ser Gln Asn Gln Ser Leu Ser Glu Leu Val Val Phe
                45                  50                  55

TGG CAG GAC CAG GAA AAC TTG GTT CTG AAT GAG GTA TAC TTA GGC AAA        363
Trp Gln Asp Gln Glu Asn Leu Val Leu Asn Glu Val Tyr Leu Gly Lys
            60                  65                  70

GAG AAA TTT GAC AGT GTT CAT TCC AAG TAT ATG GGC CGC ACA AGT TTT        411
Glu Lys Phe Asp Ser Val His Ser Lys Tyr Met Gly Arg Thr Ser Phe
        75                  80                  85

GAT TCG GAC AGT TGG ACC CTG AGA CTT CAC AAT CTT CAG ATC AAG GAC        459
Asp Ser Asp Ser Trp Thr Leu Arg Leu His Asn Leu Gln Ile Lys Asp
    90                  95                 100

AAG GGC TTG TAT CAA TGT ATC ATC CAT CAC AAA AAG CCC ACA GGA ATG        507
Lys Gly Leu Tyr Gln Cys Ile Ile His His Lys Lys Pro Thr Gly Met
105                 110                 115                 120

ATT CGC ATC CAC CAG ATG AAT TCT GAA CTG TCA GTG CTT GCT AAC TTC        555
Ile Arg Ile His Gln Met Asn Ser Glu Leu Ser Val Leu Ala Asn Phe
                125                 130                 135

AGT CAA CCT GAA ATA GTA CCA ATT TCT AAT ATA ACA GAA AAT GTG TAC        603
Ser Gln Pro Glu Ile Val Pro Ile Ser Asn Ile Thr Glu Asn Val Tyr
            140                 145                 150

ATA AAT TTG ACC TGC TCA TCT ATA CAC GGT TAC CCA GAA CCT AAG AAG        651
Ile Asn Leu Thr Cys Ser Ser Ile His Gly Tyr Pro Glu Pro Lys Lys
        155                 160                 165

ATG AGT GTT TTG CTA AGA ACC AAG AAT TCA ACT ATC GAG TAT GAT GGT        699
Met Ser Val Leu Leu Arg Thr Lys Asn Ser Thr Ile Glu Tyr Asp Gly
    170                 175                 180

ATT ATG CAG AAA TCT CAA GAT AAT GTC ACA GAA CTG TAC GAC GTT TCC        747
Ile Met Gln Lys Ser Gln Asp Asn Val Thr Glu Leu Tyr Asp Val Ser
185                 190                 195                 200

ATC AGC TTG TCT GTT TCA TTC CCT GAT GTT ACG AGC AAT ATG ACC ATC        795
Ile Ser Leu Ser Val Ser Phe Pro Asp Val Thr Ser Asn Met Thr Ile
                205                 210                 215

TTC TGT ATT CTG GAA ACT GAC AAG ACG CGG CTT TTA TCT TCA CCT TTC        843
Phe Cys Ile Leu Glu Thr Asp Lys Thr Arg Leu Leu Ser Ser Pro Phe
            220                 225                 230

TCT ATA GAG CTT GAG GAC CCT CAG CCT CCC CCA GAC CAC ATT CCT TGG        891
Ser Ile Glu Leu Glu Asp Pro Gln Pro Pro Pro Asp His Ile Pro Trp
        235                 240                 245

ATT ACA GCT GTA CTT CCA ACA GTT ATT ATA TGT GTG ATG GTT TTC TGT        939
Ile Thr Ala Val Leu Pro Thr Val Ile Ile Cys Val Met Val Phe Cys
    250                 255                 260

CTA ATT CTA TGG AAA TGG AAG AAG AAG CGG CCT CGC AAC TCT TAT            987
Leu Ile Leu Trp Lys Trp Lys Lys Lys Arg Pro Arg Asn Ser Tyr
265                 270                 275                 280

AAA TGT GGA ACC AAC ACA ATG GAG AGG GAA GAG AGT GAA CAG ACC AAG       1035
Lys Cys Gly Thr Asn Thr Met Glu Arg Glu Glu Ser Glu Gln Thr Lys
                285                 290                 295

AAA AGA GAA AAA ATC CAT ATA CCT GAA AGA TCT GAT GAA GCC CAG CGT       1083
Lys Arg Glu Lys Ile His Ile Pro Glu Arg Ser Asp Glu Ala Gln Arg
            300                 305                 310

GTT TTT AAA AGT TCG AAG ACA TCT TCA TGC GAC AAA AGT GAT ACA TGT       1131
Val Phe Lys Ser Ser Lys Thr Ser Ser Cys Asp Lys Ser Asp Thr Cys
        315                 320                 325

TTT TAATTAAAGA GTAAAGCCCA AAAAAA                                      1161
Phe
```

(2) INFORMATION FOR SEQ ID NO:25:

(i) SEQUENCE CHARACTERISTICS:

(A) LENGTH: 629 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..96

(xi) SEQUENCE DESCRIPTION: SEQ ID NO:25:

```
AGA AGC TGT TTC AGA AGA AAT GAG GCA AGC AGA GAA ACA AAC AAC AGC        48
Arg Ser Cys Phe Arg Arg Asn Glu Ala Ser Arg Glu Thr Asn Asn Ser
 1               5                  10                  15

CTT ACC TTC GGG CCT GAA GAA GCA TTA GCT GAA CAG ACC GTC TTC CTT        96
Leu Thr Phe Gly Pro Glu Glu Ala Leu Ala Glu Gln Thr Val Phe Leu
                20                  25                  30

TAGTTCTTCT CTGTCCATGT GGGATACATG GTATTATGTG GCTCATGAGG TACAATCTTT     156

CTTTCAGCAC CGTGCTAGCT GATCTTTCGG ACAACTTGAC ACAAGATAGA GTTAACTGGG     216

AAGAGAAAGC CTTGAATGAG GATTTCTTTC CATCAGGAAG CTACGGGCAA GTTTGCTGGG     276

CCTTTGATTG CTTGATGACT GAAGTGGAAA GGCTGAGCCC ACTGTGGGTG GTGCTAGAAA     336

TGGGCAGGGG CAGGTGACCC TGGGTGGTAT AAGAAAAAGA GCTGTCACTA AAAGGAGAGG     396

TGCCTAGTCT TACTGCAACT TGATATGTCA TGTTTGGTTG GTGTCTGTGG GAGGCCTGCC     456

CTTTTCTGAA GAGAAGTGGT GGGAGAGTGG ATGGGGTGGG GGCAGAGGAA AAGTGGGGGA     516

GAGGGCCTGG GAGGAGAGGA GGGAGGGGGA CGGGGTGGGG GTGGGAAAA CTATGGTTGG      576

GATGTAAAAA CGGATAATAA TATAAATATT AAATAAAAAG AGAGTATTGA GCA            629
```

(2) INFORMATION FOR SEQ ID NO:26:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:26:

```
Arg Ser Cys Phe Arg Arg Asn Glu Ala Ser Arg Glu Thr Asn Asn Ser
 1               5                  10                  15

Leu Thr Phe Gly Pro Glu Glu Ala Leu Ala Glu Gln Thr Val Phe Leu
                20                  25                  30
```

(2) INFORMATION FOR SEQ ID NO:27:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..69

(xi) SEQUENCE DESCRIPTION: SEQ ID NO:27:

```
TGC TTT GCC CCA AGA TGC AGA GAG AGA AGG AGG AAT GAG AGA TTG AGA        48
Cys Phe Ala Pro Arg Cys Arg Glu Arg Arg Arg Asn Glu Arg Leu Arg
 1               5                  10                  15

AGG GAA AGT GTA CGC CCT GTA TAACAGTGTC CGCAGAAGCA AGGGGCTGAA           99
```

```
Arg Glu Ser Val Arg Pro Val
            20

AAGATCTGAA GGTAGCCTCC GTCATCTCTT CTGGGATACA TGGATCGTGG GGATCATGAG    159

GCATTCTTCC CTTAACAAAT TTAAGCTGTT TTACCCACTA CCTCACCTTC TTAAAAACCT    219

CTTTCAGATT AAGCTGAACA GTTACAAGAT GGCTGGCATC CCTCTCCTTT CTCCCCATAT    279

GCAATTTGCT TAATGTAACC TCTTCTTTTG CCATGTTTCC ATTCTGCCAT CTTGAATTGT    339

CTTGTCAGCC AATTCATTAT CTATTAAACA CTAATTTGAG                         379

(2) INFORMATION FOR SEQ ID NO:28:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:28:

Cys Phe Ala Pro Arg Cys Arg Glu Arg Arg Asn Glu Arg Leu Arg
  1               5                  10                  15

Arg Glu Ser Val Arg Pro Val
            20

(2) INFORMATION FOR SEQ ID NO:29:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..135

(xi) SEQUENCE DESCRIPTION: SEQ ID NO:29:

CAC AAG AAG CCG AAT CAG CCT AGC AGG CCC AGC AAC ACA GCC TCT AAG      48
His Lys Lys Pro Asn Gln Pro Ser Arg Pro Ser Asn Thr Ala Ser Lys
  1               5                  10                  15

TTA GAG CGG GAT AGT AAC GCT GAC AGA GAG ACT ATC AAC CTG AAG GAA      96
Leu Glu Arg Asp Ser Asn Ala Asp Arg Glu Thr Ile Asn Leu Lys Glu
             20                  25                  30

CTT GAA CCC CAA ATT GCT TCA GCA AAA CCA AAT GCA GAG TGAAGGCAGT      145
Leu Glu Pro Gln Ile Ala Ser Ala Lys Pro Asn Ala Glu
         35                  40                  45

GAGAGCCTGA GGAAAGAGTT AAAAATTGCT TTGCCTGAAA TAAGAAGTGC AGAGTTTCTC    205

AGAATTCAAA AATGTTCTCA GCTGATTGGA ATTCTACAGT TGAATAATTA AAGAAC        261

(2) INFORMATION FOR SEQ ID NO:30:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:30:

His Lys Lys Pro Asn Gln Pro Ser Arg Pro Ser Asn Thr Ala Ser Lys
  1               5                  10                  15
```

```
Leu Glu Arg Asp Ser Asn Ala Asp Arg Glu Thr Ile Asn Leu Lys Glu
            20                  25                  30

Leu Glu Pro Gln Ile Ala Ser Ala Lys Pro Asn Ala Glu
        35                  40                  45
```

(2) INFORMATION FOR SEQ ID NO:31:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..183

(xi) SEQUENCE DESCRIPTION: SEQ ID NO:31:

```
AAA TGG AAG AAG AAG AAG CGG CCT CGC AAC TCT TAT AAA TGT GGA ACC      48
Lys Trp Lys Lys Lys Lys Arg Pro Arg Asn Ser Tyr Lys Cys Gly Thr
 1               5                  10                  15

AAC ACA ATG GAG AGG GAA GAG AGT GAA CAG ACC AAG AAA AGA GAA AAA      96
Asn Thr Met Glu Arg Glu Glu Ser Glu Gln Thr Lys Lys Arg Glu Lys
            20                  25                  30

ATC CAT ATA CCT GAA AGA TCT GAT GAA GCC CAG CGT GTT TTT AAA AGT     144
Ile His Ile Pro Glu Arg Ser Asp Glu Ala Gln Arg Val Phe Lys Ser
        35                  40                  45

TCG AAG ACA TCT TCA TGC GAC AAA AGT GAT ACA TGT TTT TAATTAAAGA      193
Ser Lys Thr Ser Ser Cys Asp Lys Ser Asp Thr Cys Phe
    50                  55                  60

GTAAAGCCCA AAAAAAA                                                  210
```

(2) INFORMATION FOR SEQ ID NO:32:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:32:

```
Lys Trp Lys Lys Lys Lys Arg Pro Arg Asn Ser Tyr Lys Cys Gly Thr
 1               5                  10                  15

Asn Thr Met Glu Arg Glu Glu Ser Glu Gln Thr Lys Lys Arg Glu Lys
            20                  25                  30

Ile His Ile Pro Glu Arg Ser Asp Glu Ala Gln Arg Val Phe Lys Ser
        35                  40                  45

Ser Lys Thr Ser Ser Cys Asp Lys Ser Asp Thr Cys Phe
    50                  55                  60
```

(2) INFORMATION FOR SEQ ID NO:33:

(i) SEQUENCE CHARACTERISTICS:
        (A) LENGTH: 359 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 249..359

(xi) SEQUENCE DESCRIPTION: SEQ ID NO:33:

```
GAGTTTTATA CCTCAATAGA CTCTTACTAG TTTCTCTTTT TCAGGTTGTG AAACTCAACC      60

TTCAAAGACA CTCTGTTCCA TTTCTGTGGA CTAATAGGAT CATCTTTAGC ATCTGCCGGG     120

TGGATGCCAT CCAGGCTTCT TTTTCTACAT CTCTGTTTCT CGATTTTGT GAGCCTAGGA      180

GGTGCCTAAG CTCCATTGGC TCTAGATTCC TGGCTTTCCC CATCATGTTC TCCAAAGCAT     240

CTGAAGCT ATG GCT TGC AAT TGT CAG TTG ATG CAG GAT ACA CCA CTC CTC      290
         Met Ala Cys Asn Cys Gln Leu Met Gln Asp Thr Pro Leu Leu
           1               5                  10

AAG TTT CCA TGT CCA AGG CTC AAT CTT CTC TTT GTG CTG CTG ATT CGT       338
Lys Phe Pro Cys Pro Arg Leu Asn Leu Leu Phe Val Leu Leu Ile Arg
 15              20                  25                  30

CTT TCA CAA GTG TCT TCA GAT                                           359
Leu Ser Gln Val Ser Ser Asp
                35
```

(2) INFORMATION FOR SEQ ID NO:34:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:34:

```
Met Ala Cys Asn Cys Gln Leu Met Gln Asp Thr Pro Leu Leu Lys Phe
 1               5                  10                  15

Pro Cys Pro Arg Leu Ile Leu Leu Phe Val Leu Leu Ile Arg Leu Ser
                20                  25                  30

Gln Val Ser Ser Asp
        35
```

(2) INFORMATION FOR SEQ ID NO:35:

(i) SEQUENCE CHARACTERISTICS:
        (A) LENGTH: 416 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 318..416

(xi) SEQUENCE DESCRIPTION: SEQ ID NO:35:

```
CCAAAGAAAA AGTGATTTGT CATTGCTTTA TAGACTGTAA GAAGAGAACA TCTCAGAAGT      60

GGAGTCTTAC CCTGAAATCA AAGGATTTAA AGAAAAAGTG GAATTTTTCT TCAGCAAGCT     120

GTGAAACTAA ATCCACAACC TTTGGAGACC CAGGAACACC CTCCAATCTC TGTGTGTTTT     180

GTAAACATCA CTGGAGGGTC TTCTACGTGA GCAATTGGAT TGTCATCAGC CCTGCCTGTT    240

TTGCACCTGG GAAGTGCCCT GGTCTTACTT GGGTCCAAAT TGTTGGCTTT CACTTTTGAC    300

CCTAAGCATC TGAAGCC ATG GGC CAC ACA CGG AGG CAG GGA ACA TCA CCA       350
                    Met Gly His Thr Arg Arg Gln Gly Thr Ser Pro
                     1               5                  10

TCC AAG TGT CCA TAC CTG AAT TTC TTT CAG CTC TTG GTG CTG GCT GGT       398
Ser Lys Cys Pro Tyr Leu Asn Phe Phe Gln Leu Leu Val Leu Ala Gly
         15                  20                  25
```

```
CTT TCT CAC TTC TGT TCA                                                    416
Leu Ser His Phe Cys Ser
         30
```

(2) INFORMATION FOR SEQ ID NO:36:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:36:

```
Met Gly His Thr Arg Arg Gln Gly Thr Ser Pro Ser Lys Cys Pro Tyr
 1               5                  10                  15

Leu Asn Phe Phe Gln Leu Leu Val Leu Ala Gly Leu Ser His Phe Cys
             20                  25                  30

Ser
```

(2) INFORMATION FOR SEQ ID NO:37:

(i) SEQUENCE CHARACTERISTICS:
        (A) LENGTH: 113 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 99..113

(xi) SEQUENCE DESCRIPTION: SEQ ID NO:37:

```
GGAGCAAGCA GACGCGTAAG AGTGGCTCCT GTAGGCAGCA CGGACTTGAA CAACCAGACT     60

CCTGTAGACG TGTTCCAGAA CTTACGGAAG CACCCACG ATG GAC CCC AGA TGC       113
                                         Met Asp Pro Arg Cys
                                          1               5
```

(2) INFORMATION FOR SEQ ID NO:38:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:38:

```
Met Asp Pro Arg Cys
 1               5
```

(2) INFORMATION FOR SEQ ID NO:39:

(i) SEQUENCE CHARACTERISTICS:
        (A) LENGTH: 124 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 107..124

(xi) SEQUENCE DESCRIPTION: SEQ ID NO:39:

```
CACAGGGTGA AAGCTTTGCT TCTCTGCTGC TGTAACAGGG ACTAGCACAG ACACACGGAT        60

GAGTGGGGTC ATTTCCAGAT ATTAGGTCAC AGCAGAAGCA GCCAAA ATG GAT CCC          115
                                                  Met Asp Pro
                                                    1

CAG TGC ACT                                                             124
Gln Cys Thr
    5
```

(2) INFORMATION FOR SEQ ID NO:40:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:40:

```
Met Asp Pro Gln Cys Thr
 1           5
```

(2) INFORMATION FOR SEQ ID NO:41:

(i) SEQUENCE CHARACTERISTICS:
        (A) LENGTH: 195 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 148..195

(xi) SEQUENCE DESCRIPTION: SEQ ID NO:41:

```
AGGAGCCTTA GGAGGTACGG GGAGCTCGCA AATACTCCTT TTGGTTTATT CTTACCACCT        60

TGCTTCTGTG TTCCTTGGGA ATGCTGCTGT GCTTATGCAT CTGGTCTCTT TTTGGAGCTA       120

CAGTGGACAG GCATTTGTGA CAGCACT ATG GGA CTG AGT AAC ATT CTC TTT           171
                            Met Gly Leu Ser Asn Ile Leu Phe
                              1               5

GTG ATG GCC TTC CTG CTC TCT GGT                                         195
Val Met Ala Phe Leu Leu Ser Gly
 10               15
```

(2) INFORMATION FOR SEQ ID NO:42:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:42:

```
Met Gly Leu Ser Asn Ile Leu Phe Val Met Ala Phe Leu Leu Ser Gly
 1               5                  10                  15
```

(2) INFORMATION FOR SEQ ID NO: 43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 43:

CCAACATAAC TGAGTCTGGA AA                                                22

(2) INFORMATION FOR SEQ ID NO: 44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 44:

CTGGATTCTG ACTCACCTTC A                                                 21

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 45:

AGGTTAAGAG TGGTAGAGCC A                                                 21

(2) INFORMATION FOR SEQ ID NO: 46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 46:

AATACCATGT ATCCCACATG G                                                 21

(2) INFORMATION FOR SEQ ID NO: 47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 47:

CTGAAGCTAT GGCTTGCAAT T                                                 21

(2) INFORMATION FOR SEQ ID NO: 48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 48:

TGGCTTCTCT TTCCTTACCT T                                                 21

(2) INFORMATION FOR SEQ ID NO: 49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 49:

GCAAATGGTA GATGAGACTG T                            21

(2) INFORMATION FOR SEQ ID NO: 50:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 50:

CAACCGAGAA ATCTACCAGT AA                          22

(2) INFORMATION FOR SEQ ID NO: 51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 51:

GCCGGTAACA AGTCTCTTCA                             20

(2) INFORMATION FOR SEQ ID NO: 52:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 52:

AAAAGCTCTA TAGCATTCTG TC                          22

(2) INFORMATION FOR SEQ ID NO: 53:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 53:

ACTGACTTGG ACAGTTGTTC A                            21

(2) INFORMATION FOR SEQ ID NO: 54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 54:

TTTGATGGAC AACTTTACTA                                               20

(2) INFORMATION FOR SEQ ID NO: 55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 55:

CAGCTCACTC AGGCTTATGT                                               20

(2) INFORMATION FOR SEQ ID NO: 56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 56:

AAACAGCATC TGAGATCAGC A                                             21

(2) INFORMATION FOR SEQ ID NO: 57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 57:

CTGAGATCAG CAAGACTGTC                                               20

(2) INFORMATION FOR SEQ ID NO: 58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 58:

CTGAAGCTAT GGCTTGCAAT T                                             21

(2) INFORMATION FOR SEQ ID NO: 59:

(i) SEQUENCE CHARACTERISTICS:
        (A) LENGTH: 22 base pairs
        (B) TYPE: nucleic acid
        (C) STRANDEDNESS: single -continued

```
        (D) TOPOLOGY: linear (ii) MOLECULE TYPE: oligonucleotide (xi) SEQUENCE DESCRIPTION: SEQ ID NO: 59:

ACAAGTGTCT TCAGATGTTG AT                                          22

(2) INFORMATION FOR SEQ ID NO: 60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 60:

CTGGATTCTG ACTCACCTTC A                                           21

(2) INFORMATION FOR SEQ ID NO: 61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 61:

CCAGGTGAAG TCCTCTGACA                                             20
```

B7-1 AND B7-2 POLYPEPTIDES

GOVERNMENT FUNDING

Work described herein was supported under CA-40216 and GM46883 awarded by the National Instiutes of Health. The U.S. government therefore may have certain rights in this invention.

BACKGROUND OF THE INVENTION

For CD4+ T lymphocyte activation to occur, two distinct signals must be delivered by antigen presenting cells to resting T lymphocytes (Schwartz, R. H. (1990) *Science* 248:1349–1356; Williams, I. R. and Unanue, E. R. (1991) *J. Immunol.* 147:3752–3760; Mueller, D. L. et al., (1989) *J. Immunol.* 142:2617–2628). The first, or primary, activation signal is mediated physiologically by the interaction of the T cell receptor/CD3 complex (TcR/CD3) with MHC class II-associated antigenic peptide and gives specificity to the immune response. The second signal, the costimulatory signal, regulates the T cell proliferative response and induction of effector functions. Costimulatory signals appear pivotal in determining the functional outcome of T cell activation since delivery of an antigen-specific signal to a T cell in the absence of a costimulatory signal results in functional inactivation of mature T cells, leading to a state of tolerance (Schwartz, R. H. (1990) *Science* 248:1349–1356).

Molecules present on the surface of antigen presenting cells which are involved in T cell costimulation have been identified. These T cell costimulatory molecules include murine B7-1 (mB7-1; Freeman, G. J. et al., (1991) *J. Exp. Med.* 174:625–631), and the more recently identified murine B7-2 (mB7-2; Freeman, G. J. et al., (1993) *J. Exp. Med.* 178:2185–2192). Human counterparts to the murine B7-1 and B7-2 molecules have also been described (human B7-1 (hB7-1) Freedman, A.S. et al., (1987) *J. Immunol.* 137:3260–3267; Freeman, G. J. et al., (1989) *J. Immunol.* 143:2714–2722; and human B7-2 (hB7-2); Freeman, G. J. et al., (1993) *Science* 262:909–911; Azuma, M. et al. (1993) *Nature* 366:76–79). The B7-1 and B7-2 genes are members of the immmunoglobulin gene superfamily.

B7-1 and B7-2 display a restricted pattern of cellular expression, which correlates with accessory cell potency in providing costimulation (Reiser, H. et al. (1992; *Proc. Natl. Acad. Sci. USA* 89:271–275; Razi-Wolf Z. et al., (1992) *Proc. Natl. Acad. Sci. USA* 89:4210–4214; Galvin, F. et al. (1992) *J. Immunol.* 142:3802–3808; Freeman, G. J. et al., (1993) *J. Exp. Med* 178:2185–2192). For example, B7-1 has been observed to be expressed on activated B cells, T cells and monocytes but not on resting B cells, T cells or monocytes, and its expression can be regulated by different extracellular stimuli (Linsley, P. S. et al., (1990) *Proc. Natl.Acad. Sci. USA* 87:5031–5035; Linsley, P. S. et al., (1991) *J. Exp. Med.* 174:561–569; Reiser, H. et al. (1992); *Proc. Natl. Acad. Sci. USA* 89:271–275; Gimmi, C. D. et al. (1991) *Proc. Natl. Acad. Sci. USA* 88:6575–6579; Koulova, L. et al. (1991) *J. Exp. Med.* 173:759–762; Azuma, M. et al. (1993) *J. Exp. Med.* 177:845–850; Sansom, D. M. et al. (1993) *Eur. J. Immunol.* 23:295–298)

Both B7-1 and B7-2 are counter-receptors for two ligands, CD28 and CTLA4, expressed on T lymphocytes (Linsley, P. S. et al., (1990) *Proc. Natl.Acad. Sci. USA* 87:5031–5035; Linsley, P. S. et al., (1991) *J. Exp. Med.* 174:561–569). CD28 is constitutively expressed on T cells and, after ligation by a costimulatory molecule, induces IL-2 secretion and T cell proliferation (June, C. H. et al. (1990) *Immunol. Today* 11:211–216). CTLA4 is homologous to CD28 and appears on T cells after activation (Freeman, G. J. et al. (1992) *J. Immunol.* 149:3795–3801). Although CTLA4 has a significantly higher affinity for B7-1 than does CD28, its role in T cell activation remains to be determined. It has been shown that antigen presentation to T cells in the absence of the B7-1/CD28 costimulatory signal results in T cell anergy (Gimmi, C. D. et al. (1993) *Proc. Natl. Acad. Sci. USA* 90:6586–6590; Boussiotis, V. A. et al. (1993) *J. Exp. Med.* 178:1753). The ability of T cell costimulatory molecules such as B7-1 and B7-2 to bind to CD28 and/or CTLA4 on T cells and trigger a costimulatory signal in the T cells provides a functional role for these molecules in T cell activation.

SUMMARY OF THE INVENTION

This invention pertains to novel forms of T cell costimulatory molecules. In particular, the invention pertains to isolated proteins encoded by T cell costimulatory molecule genes which contain amino acid sequences encoded by novel exons of these genes. The isolated proteins of the invention correspond to alternative forms of T cell costimulatory molecules. Preferably, these alternative forms correspond to naturally-occurring, alternatively spliced forms of T cell costimulatory molecules or are variants of alternatively spliced forms which are produced by recombinant DNA techniques. The novel forms of T cell costimulatory molecules of the invention contain an alternative structural domain (i.e., a structural domain having an amino acid sequence which differs from a known amino acid sequence) or have a structural domain deleted or added. The occurrence in nature of alternative structural forms of T cell costimulatory molecules supports additional functional roles for T cell costimulatory molecules.

The invention also provides isolated nucleic acid molecules encoding alternative forms of proteins which bind to CD28 and/or CTLA4 and isolated proteins encoded therein. Isolated nucleic acid molecules encoding polypeptides corresponding to novel structural domains of T cell costimulatory molecules, and isolated polypeptide encoded therein are also within the scope of the invention. The novel structural domains of the invention are encoded by exons of T cell costimulatory molecule genes. In one embodiment of the invention, the T cell costimulatory molecule gene encodes B7-1. In another embodiment, the T cell costimulatory molecule gene encodes B7-2.

Another aspect of the invention provides proteins which bind CD28 and/or CTLA4 and contain a novel cytoplasmic domain. T cell costimulatory molecule genes which contain exons encoding different cytoplasmic domains which are used in an alternate manner have been discovered. Alternative splicing of mRNA transcripts of a T cell costimulatory molecule gene has been found to generate native T cell costimulatory molecules with different cytoplasmic domains. The existence of alternative cytoplasmic domain forms of T cell costimulatory molecules supports a functional role for the cytoplasmic domain in transmitting an intracellular signal within a cell which expresses the costimulatory molecule on its surface. This indicates that costimulatory molecules not only trigger an intracellular signal in T cells, but may also deliver a signal to the cell which expresses the costimulatory molecule. This is the first evidence that the interaction between a costimulatory molecule on one cell and its receptor on a T cell may involve bidirectional signal transduction between the cells (rather than only unidirectional signal transduction to the T cell).

In yet another aspect of the invention, proteins that bind CD28 and/or CTLA4 and contain a novel signal peptide domain are provided. T cell costimulatory molecule genes which contain exons encoding different signal peptide domains which are used in an alternate manner have been discovered. Alternative splicing of mRNA transcripts of the gene can generate native T cell costimulatory molecules with different signal peptide domains. The existence of alternative signal peptide domain forms of T cell costimulatory molecules also suggests a functional role for the signal peptide of T cell costimulatory molecules.

An isolated nucleic acid molecule of the invention can be incorporated into a recombinant expression vector and transfected into a host cell to express a novel structural form of a T cell costimulatory molecule. The isolated nucleic acids of the invention can further be used to create transgenic and homologous recombinant non-human animals. The novel T cell costimulatory molecules provided by the invention can be used to trigger a costimulatory signal in a T lymphocyte. These molecules can further be used to raise antibodies against novel structural domains of costimulatory molecules. The novel T cell costimulatory molecules of the invention can also be used to identify agents which stimulate the expression of alternative forms of costimulatory molecules and to identify components of the signal transduction pathway induced in a cell expressing a costimulatory molecule in response to an interaction between the costimulatory molecule and its receptor on a T lymphocyte.

DETAILED DESCRIPTION OF THE INVENTION

Figure 1:
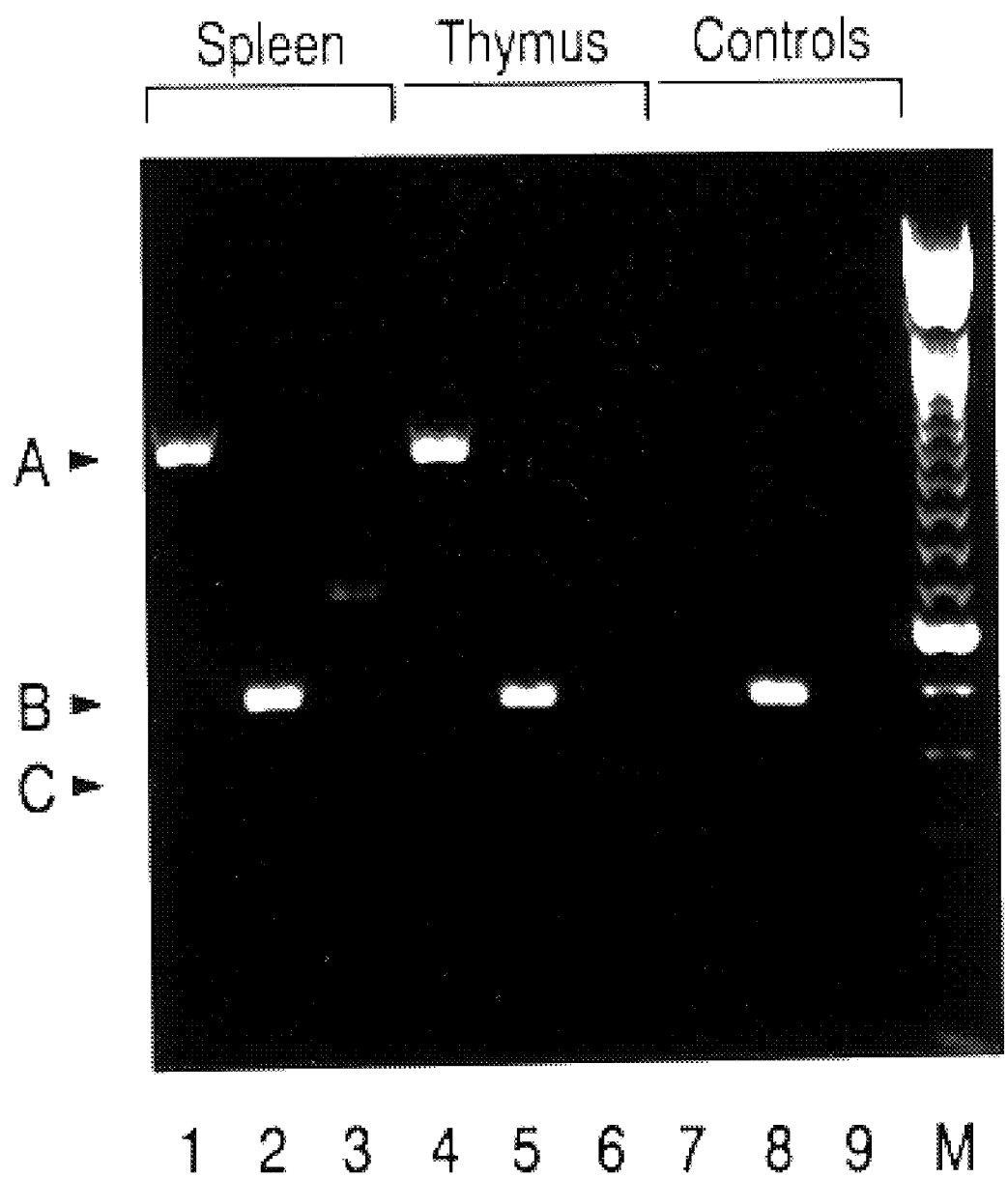
FIG. 1 is a photograph of an agarose gel depicting the presence of mB7-1 cytoplasmic domain II-encoding exon 6 in mB7-1 cDNA, determined by nested Reverse Transcriptase Polymerase Chain Reaction (RT-PCR).

This invention pertains to novel structural forms of T cell costimulatory molecule which contain a structural domain encoded by a novel exon of a T cell costimulatory molecule gene, or have a structural domain deleted or added. Preferably, the isolated T cell costimulatory molecule corresponds to a naturally-occurring alternatively spliced form of a T cell costimulatory molecule, such as B7-1 or B7-2. Alternatively, the isolated protein can be a variant of a naturally-occurring alternatively spliced form of a T cell costimulatory molecule which is produced by standard recombinant DNA techniques.

Typically, a domain structure of a T cell costimulatory molecule of the invention includes a signal peptide domain, an immunoglobulin variable region-like domain (IgV-ike), an immunoglobulin constant region-like domain (IgC-like), a transmembrane domain and a cytoplasmic domain. T cell costimulatory molecule genes are members of the immunoglobulin gene superfamily. The terms "immunogloublin variable region-like domain" and "immunoglobulin constant region-like domain" are art-recognized and refer to protein domains which are homologous in sequence to an immunoglobulin variable region or an immunoglobulin constant region, respectively. For a discussion of the immunoglobulin gene superfamily and a description of IgV-like and IgC-like domains see Hunkapiller, T. and Hood, L. (1989) *Advances in Immunology* 44:1–63. Each structural domain of a protein is usually encoded in genomic DNA by at least one exon. The invention is based, at least in part, on the discovery of novel exons in T cell costimulatory molecule genes which encode different forms of structural domains. Moreover, it has been discovered that exons encoding different forms of a structural domain of a T cell costimulatory molecule can be used in an alternative manner by alternative splicing of primary mRNA transcripts of a gene. Alternative splicing is an art-recognized term referring to the mechanism by which primary mRNA transcripts of a gene are processed to produce different mature mRNA transcripts encoding different proteins. In this mechanism different exonic sequences are excised from different primary transcripts. This results in mature MRNA transcripts from the same gene that contain different exonic sequences and thus encode proteins having different amino acid sequences. The terms "alternative forms" or "novel forms" of T cell costimulatory molecules refer to gene products of the same gene which differ in nucleotide or amino acid sequence from previously disclosed forms of T cell costimulatory molecules, e.g., forms which result from alternative splicing of a primary mRNA transcript of a gene encoding a T cell costimulatory molecule.

Accordingly, one aspect of the invention relates to isolated nucleic acids encoding T cell costimulatory molecules corresponding to naturally-occurring alternatively spliced forms or variants thereof, and uses therefor. Another aspect of the invention pertains to novel structural forms of T cell costimulatory molecules which are produced by translation of the nucleic acid molecules of the invention, and uses therefor. This invention further pertains to isolated nucleic acids encoding novel structural domains of T cell costimulatory molecules, isolated polypeptides encoded therein, and uses therefor.

The various aspects of this invention are described in detail in the following subsections.

I. Isolated Nucleic Acid Molecules Encoding T Cell Costimulatory Molecules

The invention provides an isolated nucleic acid molecule encoding a novel structural form of a T cell costimulatory molecule. As used herein, the term "T cell costimulatory molecule" is intended to include proteins which bind to CD28 and/or CTLA4. Preferred T cell costimulatory molecules are B7-1 and B7-2. The term "isolated" as used herein refers to nucleic acid substantially free of cellular material or culture medium when produced by recombinant DNA techniques, or chemical precursors or other chemicals when chemically synthesized. An "isolated" nucleic acid is also free of sequences which naturally flank the nucleic acid (i.e., sequences located at the 5' and 3' ends of the nucleic acid) in the organism from which the nucleic acid is derived. The term "nucleic acid" is intended to include DNA and RNA and can be either double stranded or single stranded. Preferably, the isolated nucleic acid molecule is a cDNA.

A. Nucleic Acids Encoding Novel Cytoplasmic Domains

One aspect of the invention pertains to isolated nucleic acids that encode T cell costimulatory molecules, each containing a novel cytoplasmic domain. It has been discovered that a gene encoding a costimulatory molecule can contain multiple exons encoding different cytoplasmic domains. In addition, naturally-occurring mRNA transcripts have been discovered which encode different cytoplasmic domain forms of T cell costimulatory molecules. Thus, one embodiment of the invention provides an isolated nucleic acid encoding a protein which binds CD28 or CTLA4 and comprises a contiguous nucleotide sequence derived from at least one T cell costimulatory molecule gene. In this embodiment, the nucleotide sequence can be represented by a formula A–B–C–D–E, wherein A comprises a nucleotide sequence of at least one first exon encoding a signal peptide domain, B comprises a nucleotide sequence of at least one second exon of a T cell costimulatory molecule gene, wherein the at least one second exon encodes an immunoglobulin variable region-like domain, C comprises a nucleotide sequence of at least one third exon of a T cell costimulatory molecule gene, wherein the at least one third exon encodes an immunoglobulin constant region-like domain, D comprises a nucleotide sequence of at least one fourth exon of a T cell costimulatory molecule gene, wherein the at least one fourth exon encodes a transmembrane domain, and E comprises a nucleotide sequence of at least one fifth exon of a T cell costimulatory molecule gene, wherein the at least one fifth exon encodes a cytoplasmic domain, with the proviso that E does not comprise a nucleotide sequence encoding a cytoplasmic domain selected from the group consisting of SEQ ID NO:28 (mB7-1), SEQ ID NO:30 (hB7-1), SEQ ID NO:32 (mB7-2) and SEQ ID NO:34 (hB7-2).

In the formula, A, B, C, D, and E are contiguous nucleotide sequences linked by phosphodiester bonds in a 5' to 3' orientation from A to E. According to the formula, A can be a nucleotide sequence of an exon which encodes a signal peptide domain of a heterologous protein which efficiently expresses transmembrane or secreted proteins, such as the oncostatin M signal peptide. Preferably, A comprises a nucleotide sequence of at least one exon which encodes a signal peptide domain of a T cell costimulatory molecule gene. It is also preferred that A, B, C, D and E comprise nucleotide sequences of exons of the B7-1 gene, such as the human or murine B7-1 gene. As described in detail in Examples 1 and 2, naturally-occurring murine B7-1 mRNA transcripts which contain a nucleotide sequence encoding one of at least two different cytoplasmic domains have been discovered. The alternative cytoplasmic domains are encoded in genomic DNA by different exons and the different mB7-1 mRNA transcripts are produced by alternative splicing of the mRNA transcripts. The genomic structure of mB7-1 has been reported to contain only a single exon encoding cytoplasmic domain (Selvakumar, A. et al. (1993) *Immunogenetics* 38:292–295). The nucleotide sequence for the mB7-1 cDNA expressed in B cells has been reported to correspond to usage of five exons, 1–2–3–4–5 (see Freeman, G. J. et al., (1991) *J. Exp. Med.* 174:625–631; the nucleotide sequence of which is shown in SEQ ID NO: 16), including a single exon encoding cytoplasmic domain. As described herein, the nucleotide sequence of a sixth exon for the mB7-1 gene which encodes a cytoplasmic domain having a different amino acid sequence than the cytoplasmic domain encoded by exon 5 has been discovered. The nucleotide sequence encoding the first cytoplasmic domain of mB7-1 (i.e., exon 5) is shown in SEQ ID NO:25 and the amino acid sequence of this cytoplasmic domain (referred to herein as Cyt I) is shown in SEQ ID NO: 26. A nucleotide sequence encoding a second, alternative cytoplasmic domain for mB7-1 (i.e., exon 6) is shown in SEQ ID NO: 4. This alternative cytoplasmic domain encoded by exon 6 (also referred to herein as Cyt II) has an amino acid sequence shown in SEQ ID NO: 5.

The Cyt II domain of mB7-1 has several characteristic properties. Of interest is the preferential expression of mRNA containing the exon encoding Cyt II (i.e., exon 6) in thymus. In contrast, mRNA containing exon 6 of mB7-1 is not detectable in spleen. Accordingly, this invention encompasses alternative cytoplasmic domain forms of T cell costimulatory molecules which are expressed preferentially in thymus. As defined herein, the term "expressed preferentially in the thymus" is intended to mean that the mRNA is detectable by standard methods in greater abundance in the thymus than in other tissues which express the T cell costimulatory molecule, particularly the spleen. The Cyt II domain of mB7-1 has also been found to contain several consensus phosphorylation sites and, thus, alternative cytoplasmic domain forms of T cell costimulatory molecules which contain at least one consensus phosphorylation site are also within the scope of this invention. As used herein, the term "consensus phosphorylation site" describes an amino acid sequence motif which is recognized by and phosphorylated by a protein kinase, for example protein kinase C, casein kinase II etc. It has also been discovered that exon 6 is encoded in genomic DNA approximately 7.5 kilobases downstream of exon 5. This invention therefore includes alternative cytoplasmic domain forms of T cell costimulatory molecules which are located in genomic DNA less than approximately 10 kb downstream (i.e., 3') of an exon encoding a first cytoplasmic domain of the T cell costimulatory molecule. Additionally, a second, alternative cytoplasmic domain of another T cell costimulatory molecule is likely to be homologous to the Cyt II domain of mB7-1. For example, the first cytoplasmic domains of mB7-1, hB7-1, mB7-2 and hB7-2 display between 4% and 26% amino acid identity (see Freeman, G. J. et al. (1993) *J. Exp. Med.* 178:2185–2192). Accordingly, in one embodiment, an alternative cytoplasmic domain of a T cell costimulatory molecule has an amino acid sequence that is at least about 5% to 25% identical in sequence with the amino acid sequence of mB7-1 Cyt II (shown in SEQ ID NO:5).

Another embodiment of the invention provides an isolated nucleic acid encoding a protein which binds CD28 or CTLA4 and is encoded by a T cell costimulatory molecule gene having at least one first exon encoding a first cytoplasmic domain and at least one second exon encoding a second cytoplasmic domain. The at least one first exon comprises a nucleotide sequence selected from the group consisting of a nucleotide sequence of SEQ ID NO:25 (mB7-1), SEQ ID NO:27 (hB7-1), SEQ ID NO:29 (mB7-2) and SEQ ID NO:31 (hB7-2). In this embodiment, the isolated nucleic acid includes a nucleotide sequence encoding at least one second cytoplasmic domain. Preferably, the isolated nucleic acid does not comprise a nucleotide sequence encoding a first cytoplasmic domain. Preferred T cell costimulatory molecule genes from which nucleotide sequences can be derived include B7-1 and B7-2.

In yet another embodiment, the isolated nucleic acid of the invention encodes a protein which binds CD28 or CTLA4 and comprises a nucleotide sequence shown in SEQ ID NO: 1. This nucleotide sequence corresponds to a naturally-occurring alternatively spliced form of mB7-1 which includes the nucleotide sequences of exons 1–2–3–4–6. Alternatively, the isolated nucleic acid comprises a nucleotide sequence shown in SEQ ID NO: 3, which corresponds to a naturally-occurring alternatively spliced form of mB7-1 comprising the nucleotide sequences of exons 1–2–3–4–5–6.

B. Nucleic Acids Encoding Novel Signal Peptide Domains

Other aspects of this invention pertain to isolated nucleic acids which encode T cell costimulatory molecules containing novel signal peptide domains. It has been discovered that a gene encoding a costimulatory molecule can contain multiple exons encoding different signal peptide domains and that mRNA transcripts occur in nature which encode different signal peptide domain forms of T cell costimulatory molecules. Thus, isolated nucleic acids which encode proteins which bind CD28 or CTLA4 and comprise contiguous nucleotide sequences derived from at least one T cell costimulatory molecule gene are within the scope of this invention. The nucleotide sequence can be represented by a formula A–B–C–D–E, wherein A comprises a nucleotide sequence of at least one first exon of a T cell costimulatory molecule gene, wherein the at least one first exon encodes a signal peptide domain, B comprises a nucleotide sequence of at least one second exon of a T cell costimulatory molecule gene, wherein the at least one second exon encodes an immunoglobulin variable region-like domain, C comprises a nucleotide sequence of at least one third exon of a T cell costimulatory molecule gene, wherein the at least one third exon encodes an immunoglobulin constant region-like domain, D, which may or may not be present, comprises a nucleotide sequence of at least one fourth exon of a T cell costimulatory molecule gene, wherein the at least one fourth exon encodes a transmembrane domain, and E, which may or may not be present, comprises a nucleotide sequence of at least one fifth exon of a T cell costimulatory molecule gene, wherein the at least one fifth exon encodes a cytoplasmic domain, with the proviso that A does not comprise a nucleotide sequence encoding a signal peptide domain selected from the group consisting of SEQ ID NO:33 (mB7-1), SEQ ID NO:35 (hB7-1), SEQ ID NO:37 (mB7-2), SEQ ID NO:39 (hB7-2) and SEQ ID NO:41 (hB7-2).

In the formula, A, B, C, D, and E are contiguous nucleotide sequences linked by phosphodiester bonds in a 5' to 3' orientation from A to E. To produce a soluble form of the T cell costimlatory molecule D, which comprises nucleotide sequence of a transmembrane domain and E, which comprises a nucleotide sequence of a cytoplasmic domain may not be present in the molecule. In a preferred embodiment, A, B, C, D and E comprise nucleotide sequences of exons of the B7-2 gene, such as the human or murine B7-2 gene. As described in detail in Example 6, naturally-occurring murine B7-2 mRNA transcripts which contain a nucleotide sequence encoding one of at least two different signal peptide domains have been discovered. An mRNA transcript containing a nucleotide sequence encoding a novel signal peptide domain represents an alternatively spliced form of murine B7-2. A naturally-occurring mB7-2 mRNA transcript encoding an alternative signal peptide domain preferably comprises the nucleotide sequence shown in SEQ ID NO: 12. The amino acid sequence of the novel signal peptide domain encoded by this transcript is shown in SEQ ID NO: 13. Accordingly, in this embodiment, the isolated nucleic acid encodes a protein which binds CD28 or CTLA4 and preferably comprises a nucleotide sequence shown in SEQ ID NO: 12.

In yet another embodiment of the invention, the isolated nucleic acid encodes a protein which binds CD28 or CTLA4 and is encoded by a T cell costimulatory molecule gene having at least one first exon encoding a first signal peptide domain and at least one second exon encoding a second signal peptide domain. The at least one first exon comprises a nucleotide sequence selected from the group consisting of a nucleotide sequence of SEQ ID NO:33 (mB7-1), SEQ ID NO:35 (hB7-1), SEQ ID NO:37 (mB7-2) and SEQ ID NO:39 (hB7-2) and SEQ ID NO:41 (hB7-2). In this embodiment, the isolated nucleic acid includes a nucleotide sequence encoding at least one second signal peptide domain. Preferably, the isolated nucleic acid does not comprise a nucleotide sequence encoding the first signal peptide domain. Preferred T cell costimulatory molecule gene from which nucleotide sequences can be derived include B7-1 and B7-2.

C. Nucleic Acids Encoding Proteins With Domains Deleted or Added

Another aspect of the invention pertains to isolated nucleic acids encoding T cell costimulatory molecules having structural domains which have been deleted or added. This aspect of the invention is based, at least in part, on the discovery that alternative splicing of mRNA transcripts encoding T cell costimulatory molecules generates transcripts in which an exon encoding a structural domain has been excised or in which at least two exons encoding two forms of a structural domain are linked in tandem. A preferred nucleic acid is one in which an exon encoding an IgV-like domain has been deleted. Accordingly, in one embodiment, the isolated nucleic acid encodes a protein comprising a contiguous nucleotide sequence derived from at least one T cell costimulatory molecule gene, the nucleotide sequence represented by a formula A–B–C–D, wherein A comprises a nucleotide sequence of at least one first exon of a T cell costimulatory molecule gene, wherein the at least one first exon encodes a signal peptide domain, B comprises a nucleotide sequence of at least one second exon of a T cell costimulatory molecule gene, wherein the at least one second exon encodes an immunoglobulin constant region-like domain, C comprises a nucleotide sequence of at least one third exon of a T cell costimulatory molecule gene, wherein the at least one third exon encodes a transmembrane domain, and D comprises a nucleotide sequence of at least one fourth exon of a T cell costimulatory molecule gene, wherein the at least one fourth exon encodes a cytoplasmic domain.

In the formula, A, B, C and D are contiguous nucleotide sequences linked by phosphodiester bonds in a 5' to 3' orientation from A to D.

Naturally-occurring mRNA transcripts encoding murine B7-1 have been detected in which the exon encoding the IgV-like domain (i.e, exon 2) has been excised and the exon encoding the signal peptide domain (i.e., exon 1) is spliced to the exon encoding the IgC-like domain (i.e., exon 3) (see Example 7). In one embodiment, an isolated nucleic acid encoding an alternatively spliced form of murine B7-1 in which an IgV-like domain exon has been deleted comprises a nucleotide sequence corresponding to usage of exons 1–3–4–5 (SEQ ID NO: 8). Alternatively, an alternatively spliced form of murine B7-1 comprises a nucleotide sequence corresponding to usage of exons 1–3–4–6 (SEQ ID NO: 10), which contains the second, alternative cytoplasmic domain of mB7-1.

Another aspect of this invention features an isolated nucleic acid encoding a T cell costimulatory molecule which contains exons in addition to a known or previously identified form of the T cell costimulatory molecule. For example, a naturally-occurring murine B7-1 mRNA transcript has been identified which contains two cytoplasmic domain-encoding exons in tandem, i.e., the transcript contains exons 1–2–3–4–5–6 (the nucleotide sequence of which is shown in SEQ ID NO: 3). Since there is an in-frame termination codon within exon 5, translation of this transcript produces a protein which contains only the Cyt I cytoplasmic domain. However, if desired, this termination codon can be mutated by standard site-directed mutagenesis techniques to create a nucleotide sequence which encodes an mB7-1 protein containing both a Cyt I and a Cyt II domain in tandem.

An isolated nucleic acid having a nucleotide sequence disclosed herein can be obtained by standard molecular biology techniques. For example, oligonucleotide primers suitable for use in the polymerase chain reaction (PCR) can be prepared based upon the nucleotide sequences disclosed herein and the nucleic acid molecule can be amplified from cDNA and isolated. At least one oligonucleotide primer should be complimentary to a nucleotide sequence encoding an alternative structural domain. It is even more preferable that at least one oligonucleotide primer span a novel exon junction created by alternative splicing. For example, an oligonucleotide primer which spans the junction of exon 4 and exon 6 can be used to preferentially amplify a murine B7-1 cDNA that contains the second, alternative cytoplasmic domain (e.g., a cDNA which contains exons 1–2–3–4–6; SEQ ID NO: 1). Alternatively, an oligonucleotide primer complimentary to a nucleotide sequence encoding a novel alternative structural domain can be used to screen a cDNA library to isolate a nucleic acid of the invention.

Isolated nucleic acid molecules having nucleotide sequences other than those specifically disclosed herein are also encompassed by the invention. For example, novel structural forms of B7-1 from species other than mouse are within the scope of the invention (e.g., alternatively spliced forms of human B7-1). Likewise, novel structural forms of B7-2 from species other than mouse are also within the scope of the invention (e.g., alternatively spliced forms of human B7-2). Furthermore, additional alternatively spliced forms for murine B7-1 and murine B7-2 can be identified using techniques described herein. These alternatively spliced forms of murine B7-1 and B7-2 are within the scope of the invention. Isolated nucleic acid molecules encoding novel structural forms of T cell costimulatory molecules can be obtained by conventional techniques, such as by methods described below and in the Examples.

An isolated nucleic acid encoding a novel structural form of a T cell costimulatory molecule can be obtained by isolating and analyzing cDNA clones encoding the T cell costimulatory molecule (e.g., mB7-1; hB7-1; mB7-2; hB7-2 etc.) by standard techniques (see for example Sambrook et al. *Molecular Cloning: A Laboratory Manual,* 2nd Edition, Cold Spring Harbor Laboratory press (1989) or other laboratory handbook). For example, cDNAs encoding the costimulatory molecule can be amplified by reverse transcriptase-polymerase chain reaction (RT-PCR) using oligonucleotide primers specific for the costimulatory molecule gene. The amplified cDNAs can then be subcloned into a plasmid vector and sequenced by standard methods. Oligonucleotide primers for RT-PCR can be designed based upon previously disclosed nucleotide sequences of costimulatory molecules (see Freeman, G. J. et al., (1991) *J. Exp. Med.* 124:625–631 for mB7-1; Freeman, G. J. et al., (1989) *J. Immunol.* 14:2714–2722 for hB7-1; Freeman, G. J. et al., (1993) *J. Exp. Med.* 178:2185–2192 for mB7-2; and Freeman, G. J. et al., (1993) *Science* 262:909–911 for hB7-2; nucleotide sequences are shown in SEQ ID NOS: 16, 18, 20, 22 and 24). For analyzing the 5' or 3' ends of mRNA transcripts, cDNA can be prepared using a 5' or 3' "RACE" procedure ("rapid amplification of cDNA ends) as described in the Examples. Alternative to amplifying specific cDNAs, a cDNA library can be prepared from a cell line which expresses the costimulatory molecule and screened with a probe containing all or a portion of the nucleotide sequence encoding the costimulatory molecule.

Individual isolated cDNA clones encoding a T cell costimulatory molecule can then be sequenced by standard techiques, such as dideoxy sequencing or Maxam-Gilbert sequencing, to identify a cDNA clone encoding a T cell costimulatory molecule having a novel structural domain. A novel structural domain can be identified by comparing the sequence of the cDNA clone to the previously disclosed nucleotide sequences encoding T cell costimulatory molecules (e.g., sequences shown in SEQ ID NO: 16, 18, 20, 22 and 24). Once a putative alternative structural domain has been identified, the nucleotide sequence encoding the domain can be mapped in genomic DNA to determine whether the domain is encoded by a novel exon. This type of approach provides the most extensive information about alternatively spliced forms of mRNAs encoding the costimulatory molecule.

Alternatively, a novel structural domain for T cell costimulatory molecules can be identified in genomic DNA by identifying a novel exon in the gene encoding the T cell costimulatory molecule. A novel exon can be identified as an open reading frame flanked by splice acceptor and splice donor sequences. Genomic clones encoding a T cell costimulatory molecule can be isolated by screening a genomic DNA library with a probe encompassing all or a portion of a nucleotide sequence encoding the costimulatory molecule (e.g., having all or a portion of a nucleotide sequence shown in SEQ ID NO: 16, 18, 20, 22 and 24). For costimulatory molecules whose genes have been mapped to a particular chromosome, a chromosome-specific library rather than a total genomic DNA library can be used. For example, hB7-1 has been mapped to human chromosome 3 (see Freeman, G. J. et al. (1992) *Blood* 79:489–494; and Selvakumar, A. et al. (1992) *Immunogenetics* 36:175–181. Genomic clones can be sequenced by conventional techniques and novel exons identified. A probe corresponding to a novel exon can then be used to detect the nucleotide sequence of this exon in mRNA transcripts encoding the costimulatory molecule (e.g., by screening a cDNA library or by PCR).

A more preferred approach for identifying and isolating nucleic acid encoding a novel structural domain of a T cell costimulatory molecule is by "exon trapping". Exon trapping is a technique that has been used successfully to identify and isolate novel exons (see e.g. Duyk, G. M. et al. (1990) *Proc. Natl. Acad. Sci. USA* 87:8995–8999; Auch, D. and Reth, M. (1990) *Nucleic Acids Res.* 18:6743–6744; Hamaguchi, M. et al. (1992) *Proc. Natl. Acad. Sci. USA* 89:9779–9783; and Krizman, D. B and Berget, S. M. (1993) *Nucleic Acids Res.* 21:5198–5202). The approach of exon trapping can be applied to the isolation of exons encoding novel structural domains of T cell costimulatory molecules, such as a novel alternative cytoplasmic domain of human B7-1, as described in Example 5.

In addition to the isolated nucleic acids encoding naturally-occurring alternatively spliced forms of T cell costimulatory molecules provided by the invention, it will be appreciated by those skilled in the art that nucleic acids encoding variant alternative forms, which may or may not occur naturally, can be obtained used standard recombinant DNA techniques. The term "variant alternative forms" is intended to include novel combinations of exon sequences which can be created using recombinant DNA techniques.

That is, novel exons encoding structural domains of T cell costimulatory molecules, either provided by the invention or identified according to the teachings of the invention, can be "spliced", using standard recombinant DNA techniques, to other exons encoding other structural domains of the costimulatory molecule, regardless of whether the particular combination of exons has been observed in nature. Thus, novel combinations of exons can be linked in vitro to create variant alternative forms of T cell costimulatory molecules. For example, the structural form of murine B7-1 which has the signal peptide domain directly joined to the IgC-like domain (ie., which has the IgV-like domain deleted) has been observed in nature in combination with the cytoplasmic domain encoded by exon 5. However, using conventional techniques, an alternative structural form can be created in which the IgV-like domain is deleted and the alternative cytoplasmic domain is encoded by exon 6. In another example, a murine B7-1 cDNA containing exons 1-2-3-4-5-6 can be mutated by site-directed mutagenesis to change a stop codon in exon 5 to an amino acid encoding-codon such that an mB7-1 protein can be produced which contains both a Cyt I domain and a Cyt II domain in tandem. Additionally, an exon encoding a structural domain of one costimulatory molecule can be transferred to another costimulatory molecule by standard techniques. For example, the cytoplasmic domain of mB7-2 can be replaced with the novel cytoplasmic domain of mB7-1 provided by the invention (i.e., exon 6 of mB7-1 can be "swapped" for the cytoplasmic domain exon of mB7-2).

It will also be appreciated by those skilled in the art that changes can be made in the nucleotide sequences provided by the invention without changing the encoded protein due to the degeneracy of the genetic code. Additionally, nucleic acids which have a nucleotide sequence different from those disclosed herein due to degeneracy of the genetic code may be isolated from biological sources. Such nucleic acids encode finctionally equivalent proteins (e.g., a protein having T cell costimulatory activity) to those described herein. For example, a number of amino acids are designated by more than one triplet codon. Codons that specify the same amino acid, or synonyms (for example, CAU and CAC are synonyms for histidine) may occur in isolated nucleic acids from different biological sources or can be introduced into an isolated nucleic acid by standard recombinant DNA techniques without changing the protein encoded by the nucleic acid. Isolated nucleic acids encoding alternatively spliced forms of T cell costimulatory molecules having a nucleotide sequence which differs from those provided herein due to degeneracy of the genetic code are considered to be within the scope of the invention.

II. Additional Isolated Nucleic Acid Molecules of the Invention

In addition to isolated nucleic acids encoding alternative forms of T cell costimulatory molecules, the invention also discloses previously undescribed nucleotide sequences of the murine B7-1 gene and mRNA transcripts. As described in detail in Example 3, it has now been discovered that murine B7-1 mRNA transcripts contain additional 5' untranslated (UT) sequences which were not previously reported. A 5' UT region of approximately 250 base pairs has been reported for mB7-1 mRNA transcripts, determined by primer extension analysis (see Selvakumar et al. (1993) *Immunogenetics* 38:292–295). As described herein, an additional ~1500 nucleotides of 5' UT sequences have been discovered in mB7-1. These 5' UT sequences are contiguous with known exon 1 sequences, thereby extending the size of exon 1 by approximately 1500 base pairs. Thus the novel 5' UT sequence of the invention corresponds to the 5' region of mB7-1 exon 1 (i.e., exon 1 extends an additional ~1500 nucleotides at its 5' end than previously reported) rather than corresponding to a new exon upstream of exon 1. Computer analysis of the potential secondary structure of the 5' UT region reveals that the most stable structure is comprised of multiply folded palindromic sequences. This high degree of secondary structure may explain the results of Selvakumar et al. ((1993) *Immunogenetics* 38:292–295) in that the secondary structure could account for premature termination of the primer extension reaction. The potential for excessive secondary structure in the 5' UT region suggests that post-transcriptional mechanisms are involved in controlling mB7-1 expression. Thus, inclusion of the long 5' UT sequence in recombinant expression vectors encoding mB7-1 may provide post-transcriptional regulation that is similar to that of the endogenous gene. Accordingly, the 5' UT region of mB7-1 provided by the invention can be incorporated by standard recombinant DNA techniques at the 5' end of a cDNA encoding a mB7-1 protein. The nucleotide sequence of the 5' UT region of mB7-1 (i.e, the full nucleotide sequence of exon 1) is shown in SEQ ID NO: 6.

The discovery of additional 5' UT sequences in mB7-1 cDNA demonstrates that transcription of the mB7-1 gene initiates further upstream (i.e., 5' ) in genomic DNA than previously reported in Selvakumar et al. (*Immunogenetics* (1993) 38:292–295). Transcription of a gene is typically regulated by sequences in genomic DNA located immediately upstream of sequences corresponding to the 5' UT region of the transcribed mRNA. Nucleotides located within approximately 200 base pairs of the start site of transcription are generally considered to encompass the promoter of the gene and often include canonical CCAAT or TATA elements indicative of a typical eukaryotic promoter. For a gene having a promoter which contains a TATA box, transcription usually starts approximately 30 base pairs downstream of the TATA box. In addition to CCAAT and TATA-containing promoters, it is now appreciated that many genes have promoters which do not contain these elements. Examples of such genes include many members of the immunoglobulin gene superfamily (see for example Breathnach, R. and Chambon, P. (1981) *Ann. Rev. Biochem.* 50:349–383; Fisher, R. C. and Thorley-Lawson, D. A. (1991) *Mol. Cell. Biol.* 11:1614–1623; Hogarth, P. M. et al. (1991) *J. Immunol.* 146:369–376; Schanberg, L. E. (1991) *Proc. Natl. Acad. Sci. USA* 88:603–607; Zhou, L. J. et al. (1991) *J. Immunol.* 147:1424–1432). In such TATA-less promoters, transcriptional regulation is thought to be provided by other DNA elements which bind transcription factors. Sequence analysis of ~180 base pairs of mB7-1 genomic DNA immediately upstream of the newly identified 5' UT region revealed the presence of numerous consensus sites for transcription factor binding, including AP-2, PU.1 and NFκB. The nucleotide sequence of this region is shown in SEQ ID NO: 7. The structure of this region (i.e, the DNA elements contained therein) is consistent with it functioning as a promoter for transcription of the mB7-1 gene. The ability of this region of DNA to function as a promoter can be determined by standard techniques routinely used in the art to identify transcriptional regulatory elements. For example, this DNA region can be cloned upstream of a reporter gene (e.g., encoding chloramphenicol acetyl transferase, β-galactosidase, luciferase etc.) in a recombinant vector, the recombinant vector transfected into an appropriate cell line and expression of the reporter gene detected as an indication that the DNA region can function as a transcriptional regulatory element. If it is determined that this DNA region can function as a B7-1 promoter, it may be advantageous to use this DNA region to regulate expression of a B7-1 cDNA in a recombinant expression vector to mimic the endogenous expression of B7-1.

III. Uses for the Isolated Nucleic Acid Molecules of the Invention

A. Probes

The isolated nucleic acids of the invention are useful for constructing nucleotide probes for use in detecting nucleotide sequences in biological materials, such as cell extracts, or directly in cells (e.g., by in situ hybridization). A nucleotide probe can be labeled with a radioactive element which provides for an adequate signal as a means for detection and has sufficient half-life to be useful for detection, such as $^{32}P$, $^{3}H$, $^{14}C$ or the like. Other materials which can be used to label the probe include antigens that are recognized by a specific labeled antibody, fluorescent compounds, enzymes and chemiluminescent compounds. An appropriate label can be selected with regard to the rate of hybridization and binding of the probe to the nucleotide sequence to be detected and the amount of nucleotide available for hybridization. The isolated nucleic acids of the invention, or oligonucleotide fragments thereof, can be used as suitable probes for a variety of hybridization procedures well known to those skilled in the art. The isolated nucleic acids of the invention enable one to determine whether a cell expresses an alternatively spliced form of a T cell costimulatory molecule. For example, mRNA can be prepared from a sample of cells to be examined and the mRNA can be hybridized to an isolated nucleic acid encompassing a nucleotide sequence encoding all or a portion of an alternative cytoplasmic domain of a T cell costimulatory molecule (e.g., SEQ ID NO: 1) to detect the expression of the alternative cytoplasmic domain form of the costimulatory molecule in the cells. Furthermore, the isolated nucleic acids of the invention can be used to design oligonucleotide primers, e.g. PCR primers, which allow one to detect the expression of an alternatively spliced form of a T cell costimulatory molecule. Preferably, this oligonucleotide primer spans a novel exon junction created by alternative splicing and thus can only amplify cDNAs encoding this alternatively spliced form. For example, an oligonucleotide primer which spans exon 4 and exon 6 of murine B7-1 can be used to distinguish between the expression of a first cytoplasmic domain form of mB7-1 (i.e, encoded by exons 1–2–3–4–5) and expression of an alternative second cytoplasmic domain form of a costimulatory molecule (i.e., encoded by exons 1–2–3–4–6) (e.g., see Example 2).

The probes of the invention can be used to detect an alteration in the expression of an alternatively splicedform of a T cell costimulatory molecule, such as in a disease state. For example, detection of a defect in the expression of an alternatively splicedform of a T cell costimulatory molecule that is associated with an immunodeficiency disorder can be used to diagnose the disorder (i.e., the probes of the invention can be used for diagnostic purposes). Many congenital immunodeficiency diseases result from lack of expression of a cell-surface antigen important for interactions between T cells and antigen presenting cells. For example, the bare lymphocyte syndrome results from lack of expression of MHC class II antigens (see e.g., Rijkers, G. T. et al. (1987) *J. Clin. Immunol.* 7:98–106; Hume, C. R. et al. (1989) *Hum. Immunol.* 25:1–11)) and X-linked hyperglobulinemia results from defective expression of the ligand for CD40 (gp39) (see e.g. Korthauer, U et al. (1993) *Nature* 361:541; Aruffo, A. et al. (1993) *Cell* 12:291–300). An immunodeficiency disorder which results from lack of expression of an alternatively spliced form of a T cell costimulatory molecule can be diagnosed using a probe of the invention. For example, a disorder resulting from the lack of expression of the Cyt II form of B7-1 can be diagnosed in a patient based upon the inability of a probe which detects this form of B7-1 (e.g., an oligonucleotide spanning the junction of exon 4 and exon 6) to hybridize to mRNA in cells from the patient (e.g., by RT-PCR or by Northern blotting).

B. Recombinant Expression Vectors

An isolated nucleic acid of the invention can be incorporated into an expression vector (i.e., a recombinant expression vector) to direct expression of a novel structural form of a T cell costimulatory molecule encoded by the nucleic acid. The recombinant expression vectors are suitable for transformation of a host cell, and include a nucleic acid (or fragment thereof) of the invention and a regulatory sequence, selected on the basis of the host cells to be used for expression, which is operatively linked to the nucleic acid. Operatively linked is intended to mean that the nucleic acid is linked to a regulatory sequence in a manner which allows expression of the nucleic acid. Regulatory sequences are art-recognized and are selected to direct expression of the desired protein in an appropriate host cell. Accordingly, the term regulatory sequence includes promoters, enhancers and other expression control elements. Such regulatory sequences are known to those skilled in the art or are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type of protein desired to be expressed. Such expression vectors can be used to transfect cells to thereby produce proteins or peptides encoded by nucleic acids as described herein.

The recombinant expression vectors of the invention can be designed for expression of encoded proteins in prokaryotic or eukaryotic cells. For example, proteins can be expressed in bacterial cells such as *E. coli*, insect cells (using baculovirus), yeast cells or mammalian cells. Other suitable host cells can be found in Goeddel, *Gene Expression Technology: Methods in Enzymology* 185, Academic Press, San Diego, Calif. (1990). Expression in prokaryotes is most often carried out in *E. coli* with vectors containing constitutive or inducible promoters directing the expression of either fusion or non-fusion proteins. Fusion vectors add a number of amino acids usually to the amino terminus of the expressed target gene. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase, maltose E binding protein, or protein A, respectively, to the target recombinant protein.

Inducible non-fusion prokaryotic expression vectors include pTrc (Amann et al, (1988) *Gene* 69:301–315) and pET11d (Studier et al., *Gene Expression Technology: Methods in Enzymology* 185, Academic Press, San Diego, Calif. (1990) 60–89). In pTrc, target gene expression relies on host RNA polymerase transcription from a hybrid trp-lac fusion promoter. In pET11d, expression of inserted target genes relies on transcription from the T7 gn10-lac 0 fusion promoter mediated by a coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant protein expression in *E. coli* is to express the protein in a host bacterial strain with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector (e.g., a nucleic acid of the invention) so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention can be carried out by standard DNA synthesis techniques and are encompassed by the invention.

Examples of vectors for expression in yeast *S. cerivisae* include pYepSec1 (Baldari. et al., (1987) *Embo J.* 6:229–234), pMFa (Kujan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) Mol. Cell Biol. 3:2156–2165) and the pVL series (Lucklow, V. A., and Summers, M. D., (1989) *Virology* 170:31–39).

Expression of alternatively spliced forms of T cell costimulatory molecules in mammalian cells is accomplished using a mammalian expression vector. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral material. For example, commonly used promoters are derived from polyoma, Adenovirus 2, cytomegalovirus and Simian Virus 40. The recombinant expression vector can be designed such that expression of the nucleic acid occurs preferentially in a particular cell type. In this situation, the expression vector's control functions are provided by regulatory sequences which allow for preferential expression of a nucleic acid contained in the vector in a particular cell type, thereby allowing for tissue or cell specific expression of an encoded protein.

The recombinant expression vectors of the invention can be a plasmid or virus, or viral portion which allows for expression of a nucleic acid introduced into the viral nucleic acid. For example, replication defective retroviruses, adenoviruses and adeno-associated viruses can be used. The recombinant expression vectors can be introduced into a host cell, e.g. in vitro or in vivo. A host cell line can be used to express a protein of the invention. Furthermore, introduction of a recombinant expression vector of the invention into a host cell can be used for therapeutic purposes when the host cell is defective in expressing the novel structural form of the T cell costimulatory molecule. For example, in a recombinant expression vector of the invention can be used for gene therapy purposes in a patient with an immunodeficiency disorder resulting from lack of expression of a novel structural form of a T cell costimulatory molecule.

C. Host Cells

The invention further provides a host cell transfected with a recombinant expression vector of the invention. The term "host cell" is intended to include prokaryotic and eukaryotic cells into which a recombinant expression vector of the invention can be introduced. The terms "transformed with", "transfected with", "transformation" and "transfection" are intended to encompass introduction of nucleic acid (e.g., a vector) into a cell by one of a number of possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate co-precipitation, DEAE-dextran-mediated transfection, lipofectin, electroporation or microinjection. Suitable methods for transforming and transfecting host cells can be found in Sambrook et al. (*Molecular Cloning: A Laboratory Manual*, 2nd Edition, Cold Spring Harbor Laboratory press (1989)), and other laboratory handbooks.

The number of host cells transfected with a recombinant expression vector of the invention by techniques such as those described above will depend upon the type of recombinant expression vector used and the type of transfection technique used. Typically, plasmid vectors introduced into mammalian cells are integrated into host cell DNA at only a low frequency. In order to identify these integrants, a gene that contains a selectable marker (i.e., resistance to antibiotics) can be introduced into the host cells along with the gene of interest. Preferred selectable markers include those which confer resistance to certain drugs, such as G418 and hygromycin. Selectable markers can be introduced on a separate vector (e.g., plasmid) from the nucleic acid of interest or, preferably, are introduced on the same vector (e.g., plasmid). Host cells transformed with one or more recombinant expression vectors containing a nucleic acid of the invention and a gene for a selectable marker can be identified by selecting for cells using the selectable marker. For example, if the selectable marker encoded a gene conferring neomycin resistance, transformant cells can be selected with G418. Cells that have incorporated the selectable marker gene will survive, while the other cells die.

Preferably, the novel cytoplasmic domain form of the T cell costimulatory molecule is expressed on the surface of a host cell (e.g., on the surface of a mammalian cell). This is accomplished by using a recombinant expression vector encoding extracellular domains (e.g., signal peptide, V-like and/or C-like domains), transmembrane and cytoplasmic domains of the T cell costimulatory molecule with appropriate regulatory sequences (e.g., a signal sequence) to allow for surface expression of the translated protein.

In one embodiment, a host cell is transfected with a recombinant expression vector encoding a second, novel cytoplasmic domain form of a T cell costimulatory molecule. In a preferred embodiment, the host cell does not express the first (i.e., previously disclosed) cytoplasmic domain form of the costimulatory molecule. For example, a host cell which does not express a form of murine B7-1 containing Cyt I can be transfected with a recombinant expression vector encoding a form of murine B7-1 containing Cyt II. Such a host cell will thus excusively express the form of B7-1 containing Cyt II. This type of host cell is useful for studying signaling events and/or immunological responses which are mediated by the Cyt II domain rather than the Cyt I domain of B7-1. For example, one type of cell which can be used to create a host cell which exclusively expresses the Cyt II-form of murine B7-1 is a non-murine cell, since the non-murine cell does not express murine B7-1. Preferably, the non-murine cell also does not express other costimulatory molecules (e.g., COS cells can be used). Alternatively, a mouse cell which does not express the Cyt-I form of murine B7-1 can be used. For example, a recombinant expression vector of the invention can be introduced into NIH 3T3 fibroblast cells (which are B7-1 negative) or into cells derived from a mutant mouse in which the endogenous B7-1 gene has been disrupted and thus which does not natively express any form of B7-1 molecule (i.e., into cells derived from a "B7-1 knock-out" mouse, such as that described in Freeman, G. J. et al. (1993) *Science* 262:907–909).

In another embodiment, the host cell transfected with a recombinant expression vector encoding a novel structural form of a T cell costimulatory molecule is a tumor cell. Expression of the Cyt-I form of murine B7-1 on the surface of B7-1 negative murine tumor cells has been shown to induce T cell mediated specific immunity against the tumor cells accompanied by tumor rejection and prolonged protection to tumor challenge in mice (see Chen, L., et al. (1992) *Cell* 71, 1093–1102; Townsend, S. E. and Allison, J. P. (1993) *Science* 259, 368–370; Baskar, S., et al. (1993) *Proc. Natl. Acad. Sci.* 90, 5687–5690). Similarly, expression of novel structural forms of costimulatory molecules on the surface of a tumor cell may be useful for increasing the immunogenicity of the tumor cell. For example, tumor cells obtained from a patient can be transfected ex vivo with a recombinant expression vector of the invention, e.g., encoding an alternative cytoplasmic domain form of a costimulatory molecule, and the transfected tumor cells can then be returned to the patient. Alternatively, gene therapy techniques can be used to target a tumor cell for transfection in vivo. Additionally, the tumor cell can also be transfected with recombinant expression vectors encoding other proteins to be expressed on the tumor cell surface to increase the immunogenicity of the tumor cell. For example, the Cyt-I form of B7-1, B7-2, MHC molecules (e.g., class I and/or class II) and/or adhesion molecules can be expressed on the tumor cells in conjunction with the Cyt-II form of B7-1.

D. Anti-Sense Nucleic Acid Molecules

The isolated nucleic acid molecules of the invention can also be used to design anti-sense nucleic acid molecules, or oligonucleotide fragments thereof, that can be used to modulate the expression of alternative forms of T cell costimulatory molecules. An anti-sense nucleic acid comprises a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The hydrogen bonding of an antisense nucleic acid molecule to an mRNA transcript can prevent translation of the mRNA transcript and thus inhibit the production of the protein encoded therein. Accordingly, an anti-sense nucleic acid molecule can be designed which is complementary to a nucleotide sequence encoding a novel structural domain of a T cell costimulatory molecule to inhibit production of that particular structural form of the T cell costimulatory molecule. For example, an anti-sense nucleic acid molecule can be designed which is complementary to a nucleotide sequence encoding the Cyt-II form of murine B7-1 and used to inhibit the expression of this form of the costimulatory molecule.

An anti-sense nucleic acids molecule, or oligonucleotide fragment thereof, can be constructed by chemical synthesis and enzymatic ligation reactions using procedures known in the art. The anti-sense nucleic acid or oligonucleotide can be chemically synthesized using naturally-occurring nucleotides or variously modified nucleotides designed to increase the biological stability of the molecules or to increase the physical stability of the duplex formed between the ant-isense and sense nucleic acids e.g. phosphorothioate derivatives and acridine substituted nucleotides can be used. Alternatively, the anti-sense nucleic acids and oligonucleotides can be produced biologically using an expression vector into which a nucleic acid has been subcloned in an anti-sense orientation (i.e. nucleic acid transcribed from the inserted nucleic acid will be of an anti-sense orientation to a target nucleic acid of interest). The anti-sense expression vector is introduced into cells in the form of a recombinant plasmid, phagemid or attenuated virus in which anti-sense nucleic acids are produced under the control of a high efficiency regulatory region, the activity of which can be determined by the cell type into which the vector is introduced. For a discussion of the regulation of gene expression using anti-sense genes see Weintraub, H. et al., "Antisense RNA as a molecular tool for genetic analysis", Reviews—Trends in Genetics, Vol. 1(1) 1986.

E. Non-Human Transgenic and Homologous Recombinant Animals

The isolated nucleic acids of the invention can further be used to create a non-human transgenic animal. A transgenic animal is an animal having cells that contain a transgene, wherein the transgene was introduced into the animal or an ancestor of the animal at a prenatal, e.g., an embryonic, stage. A transgene is a DNA molecule which is integrated into the genome of a cell from which a transgenic animal develops and which remains in the genome of the mature animal, thereby directing the expression of an encoded gene product in one or more cell types or tissues of the transgenic animal. Accordingly, the invention provides a non-human transgenic animal which contains cells transfected to express an alternative form of a T cell costimulatory molecule. Preferably, the non-human animal is a mouse. A transgenic animal can be created, for example, by introducing a nucleic acid encoding the protein (typically linked to appropriate regulatory elements, such as a tissue-specific enhancer) into the male pronuclei of a fertilized oocyte, e.g., by microinjection, and allowing the oocyte to develop in a pseudopregnant female foster animal. For example, a transgenic animal (e.g., a mouse) which expresses an mB7-1 protein containing a novel cytoplasmic domain (e.g. Cyt-II) can be made using the isolated nucleic acid shown in SEQ ID NO: 1 or SEQ ID NO: 3. Alternatively, a transgenic animal (e.g., a mouse) which expresses an mB7-2 protein containing an alternative signal peptide domain can be made using the isolated nucleic acid shown in SEQ ID NO: 12. Intronic sequences and polyadenylation signals can also be included in the transgene to increase the efficiency of expression of the transgene. These isolated nucleic acids can be linked to regulatory sequences which direct the expression of the encoded protein one or more particular cell types. Methods for generating transgenic animals, particularly animals such as mice, have become conventional in the art and are described, for example, in U.S. Pat. Nos. 4,736,866 and 4,870,009 and Hogan, B. et al., (1986) A Laboratory Manual, Cold Spring Harbor, N.Y., Cold Spring Harbor Laboratory. A transgenic founder animal can be used to breed additional animals carrying the transgene.

The isolated nucleic acids of the invention can further be used to create a non-human homologous recombinant animal. The term "homologous recombinant animal" as used herein is intended to describe an animal containing a gene which has been modified by homologous recombination.

The homologous recombination event may completely disrupt the gene such that a functional gene product can no longer be produced (often referred to as a "knock-out" animal) or the homologous recombination event may modify the gene such that an altered, although still functional, gene product is produced. Preferably, the non-human animal is a mouse. For example, an isolated nucleic acid of the invention can be used to create a homologous recombinant mouse in which a recombination event has occurred in the B7-1 gene at an exon encoding a cytoplasmic domain such that this exon is altered (e.g., exon 5 or exon 6 is altered). Homologous recombinant mice can thus be created which express only the Cyt I or Cyt II domain form of B7-1. Accordingly, the invention provides a non-human knock-out animal which contains a gene encoding a B7-1 protein wherein an exon encoding a novel cytoplasmic domain is disrupted or altered.

To create an animal with homologously recombined nucleic acid, a vector is prepared which contains the DNA sequences which are to replace the endogenous DNA sequences, flanked by DNA sequences homologous to flanking endogenous DNA sequences (see for example Thomas, K. R. and Capecchi, M. R. (1987) *Cell* 51:503). The vector is introduced into an embryonic stem cell line (e.g., by electroporation) and cells in which the introduced DNA has homologously recombined with the endogenous DNA are selected (see for example Li, E. et al. (1992) *Cell* 69:915). The selected cells are then injected into a blastocyst of an animal (e.g., a mouse) to form aggregation chimeras (see for example Bradley, A. in *Teratocarcinomas and Embryonic Stem Cells: A Practical Approach,* E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA.

IV. Isolated Novel Forms of Costimulatory Molecules

The invention further provides isolated T cell costimulatory molecules encoded by the nucleic acids of the invention. These molecules have a novel structural form, either containing a novel structural domain or having a structural domain deleted or added. The term "isolated" refers to a T cell costimulatory molecule, e.g., a protein, substantially free of cellular material or culture medium when produced by recombinant DNA techniques, or chemical precursors or other chemicals when chemically synthesized. In one embodiment, the novel T cell costimulatory molecule is a B7-1 protein. In another embodiment, the novel T cell costimulatory molecule is a B7-2 protein.

A. Proteins with a Novel Cytoplasmic Domain

One aspect of the invention pertains to a T cell costimulatory molecule which includes at least one novel cytoplasmic domain. In one embodiment, the invention provides a protein which binds to CD28 and/or CTLA4 and has an amino acid sequence derived from amino acid sequences encoded by at least one T cell costimulatory molecule gene. In this embodiment, the protein comprises a contiguous amino acid sequence represented by a formula A–B–C–D–E, wherein A, which may or may not be present, comprises an amino acid sequence of a signal peptide domain, B comprises an amino acid sequence of an immunoglobulin variable region-like domain encoded by at least one exon of a T cell costimulatory molecule gene, C comprises an amino acid sequence of an immunoglobulin constant region-like domain encoded by at least one exon of aT cell costimulatory molecule gene, D comprises an amino acid sequence of a transmembrane domain encoded by at least one exon of a T cell costimulatory molecule gene, and E comprises an amino acid sequence of a cytoplasmic domain encoded by at least one exon of a T cell costimulatory molecule gene, with the proviso that E does not comprise an amino acid sequence of a cytoplasmic domain selected from the group consisting of SEQ ID NO: 26 (mB7-1), SEQ ID NO: 28 (hB7-1), SEQ ID NO: 30 (mB7-2), and SEQ ID NO: 32 (hB7-2).

In the formula, A, B, C, D, and E are contiguous amino acid residues linked by amide bonds from an N-terminus to a C-terminus. According to the formula, A can be an amino acid sequence of a signal peptide domain of a heterologous protein which efficiently expresses transmembrane or secreted proteins, such as the oncostatin M signal peptide. Preferably, A, if present, comprises an amino acid sequence of a signal peptide domain encoded by at least one exon of a T cell costimulatory molecule gene. In one preferred embodiment, the isolated protein is a B7-1 or a B7-2 protein. E preferably comprises an amino acid sequence of a murine B7-1 cytoplasmic domain having an amino acid sequence shown in SEQ ID NO: 5 (i.e., the amino acid sequence of the cytoplasmic domain encoded by the novel exon 6 of the invention).

Another embodiment of the invention provides an isolated protein which binds CD28 or CTLA4 and is encoded by a T cell costimulatory molecule gene having at least one first exon encoding a first cytoplasmic domain and at least one second exon encoding a second cytoplasmic domain. The at least one first cytoplamic domain comprises an amino acid sequence selected from the group consisting of amino acid sequence of SEQ ID NO:26 (mB7-1), SEQ ID NO:28 (hB7-1), SEQ ID NO:30 (mB7-2) and SEQ ID NO:32 (hB7-2). In this embodiment, the protein includes an amino acid sequence comprising at least one second cytoplasmic domain. Preferably, the protein does not include an amino acid sequence comprising a first cytoplasmic domain. Preferred proteins which bind CD28 and/or CTLA4 are derived from B7-1 and B7-2. In a particularly preferred embodiment, the invention provides an isolated protein which binds CD28 or CTLA4 and has a novel cytoplasmic domain comprising an amino acid sequence shown in SEQ ID NO: 2.

A. Proteins with a Novel Signal Peptide Domain

In yet another aspect of the invention, T cell costimulatory molecules which include at least one novel signal peptide domain are provided. In one embodiment, the isolated protein binds to CD28 or CTLA4 and has an amino acid sequence derived from amino acid sequences encoded by at least one T cell costimulatory molecule gene. In this embodiment, the protein comprises a contiguous amino acid sequence represented by a formula A–B–C–D–E, wherein A comprises an amino acid sequence of a signal peptide domain encoded by at least one exon of a T cell costimulatory molecule gene, B comprises an amino acid sequence of an immunoglobulin variable region-like domain encoded by at least one exon of a T cell costimulatory molecule gene, C comprises an amino acid sequence of an immunoglobulin constant region-like domain encoded by at least one exon of aT cell costimulatory molecule gene, D, which may or may not be present, comprises an amino acid sequence of a transmembrane domain encoded by at least one exon of a T cell costimulatory molecule gene, and E, which may or may not be present, comprises an amino acid sequence of a cytoplasmic domain encoded by at least one exon of a T cell costimulatory molecule gene, with the proviso that A not comprise an amino acid sequence of a signal peptide domain selected from the group consisting of SEQ ID NO: 34 (mB7-1), SEQ ID NO: 36 (hB7-1), SEQ ID NO: 38 (mB7-2), SEQ ID NO: 40 (hB7-2), SEQ ID NO: 42 (hB7-2).

In the formula, A, B, C, D, and E are contiguous amino acid residues linked by amide bonds from an N-terminus to a C-terminus. To produce a soluble form of the T cell costimlatory molecule D, which comprises an amino acid sequence of a transmembrane domain and E, which comprises an amino acid sequence of a cytoplasmic domain may not be present in the molecule. Preferably, A comprises an amino acid sequence of a novel signal peptide domain shown in SEQ ID NO: 15.

In another embodiment of the invention, the isolated protein which binds CD28 or CTLA4 is encoded by a T cell costimulatory molecule gene having at least one first exon encoding a first signal peptide domain and at least one second exon encoding a second signal peptide domain. The at least one first signal peptide domain comprises an amino acid sequence selected from the group consisting of an amino acid sequence of SEQ ID NO:34 (mB7-1), SEQ ID NO:36 (hB7-1), SEQ ID NO:38 (mB7-2) and SEQ ID NO:40 (hB7-2) and SEQ ID NO:42 (hB7-2). In this embodiment, the protein includes an amino acid sequence comprising at least one second signal peptide domain. Preferably, the protein does not include an amino acid sequence comprising a first signal peptide domain. Preferred proteins which bind CD28 and/or CTLA4 are derived from B7-1 and B7-2. In a particularly preferred embodiment, the invention features a murine B7-2 protein having a comprising an amino acid sequence shown in SEQ ID NO: 13.

C. Isolated Proteins with Structural Domains Deleted or Added

This invention also features costimulatory molecules which have at least one structural domain deleted. A preferred structural form has at least one IgV-like domain deleted. In one embodiment, the isolated protein has an amino acid sequence derived from amino acid sequences encoded by at least one T cell costimulatory molecule gene and comprises a contiguous amino acid sequence represented by a formula A–B–C–D, wherein A, which may or may not be present, comprises an amino acid sequence of a signal peptide domain encoded by at least one exon of a T cell costimulatory molecule gene, B comprises an amino acid sequence of an immunoglobulin constant region-like domain encoded by at least one exon of a T cell costimulatory molecule gene, and C comprises an amino acid sequence of a transmembrane domain encoded by at least one exon of a T cell costimulatory molecule gene, and D comprises an amino acid sequence of a cytoplasmic domain encoded by at least one exon of a T cell costimulatory molecule gene.

In the formula, A, B, C and D are contiguous amino acid residues linked by amide bonds from an N-terminus to a C-terminus. In a preferred embodiment, an isolated murine B7-1 protein having an IgV-like domain deleted comprises an amino acid sequence shown in SEQ ID NO: 9. Alternatively, an isolated murine B7-1 protein having an IgV-like domain deleted comprises an amino acid sequence shown in SEQ ID NO: 11.

The proteins of the invention can be isolated by expression of the molecules (e.g., proteins or peptide fragments thereof) in a suitable host cell using techniques known in the art. Suitable host cells include prokaryotic or eukaryotic organisms or cell lines, for example, yeast, *E. coli* and insect cells. The recombinant expression vectors of the invention, described above, can be used to express a costimulatory molecule in a host cell in order to isolate the protein. The invention provides a method of preparing an isolated protein of the invention comprising introducing into a host cell a recombinant expression vector encoding the protein, allowing the protein to be expressed in the host cell and isolating the protein. Proteins can be isolated from a host cell expressing the protein according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology,* 22,233–577 (1971)).

Alternatively, the costimulatory molecules of the invention can be prepared by chemical synthesis using techniques well known in the chemistry of proteins such as solid phase synthesis (Merrifield, 1964, J. Am. Chem. Assoc. 85:2149–2154) or synthesis in homogeneous solution (Houbenweyl, 1987, Methods of Organic Chemistry, ed. E. Wansch, Vol. 15 I and II, Thieme, Stuttgart).

V. Uses For the Novel T Cell Costimulatory Molecules of the Invention

A. Costimulation

The novel T cell costimulatory molecules of the invention can be used to trigger a costimulatory signal in T cells. When membrane-bound or in a multivalent form, a T cell costimulatory molecule can trigger a costimulatory signal in a T cell by allowing the costimulatory molecule to interact with its receptor (e.g., CD28) on T cells in the presence of a primary activation signal. A novel T cell costimulatory molecule of the invention can be obtained in membrane-bound form by expressing the molecule in a host cell (e.g., by transfecting the host cell with a recombinant expression vector encoding the molecule). To be expressed on the surface of a host cell, the T cell costimulatory molecule should include extracellular domains (i.e., signal peptide, which may or may not be present in the mature protein, IgV-like and IgC-like domains), a transmembrane domain and a cytoplasmic domain. To trigger a costimulatory signal, T cells are contacted with the cell expressing the costimulatory molecule, preferably together with a primary activation signal (e.g., MHC-associated antigenic peptide, anti-CD3 antibody, phorbol ester etc.). Activation of the T cell can be assayed by standard procedures, for example by measuring T cell proliferation or cytokine production.

The novel T cell costimulatory molecules of the invention can also be used to inhibit or block a costimulatory signal in T cells. A soluble form of a T cell costimulatory molecule can be used to competitively inhibit the interaction of membrane-bound costimulatory molecules with their receptor (e.g., CD28 and/or CTLA4) on T cells. A soluble form of a T cell costimulatory molecule can be expressed in host cell line such that it is secreted by the host cell line and can then be purified. The soluble costimulatory molecule contains extracellular domains (i.e., signal peptide, which may or may not be present in the mature protein, IgV-like and IgC-like domains) but does not contain a transmembrane or cytoplasmic domain. The soluble form of the T cell costimulatory molecule can also be in the form of a fusion protein, e.g. an immunoglobulin fusion protein wherein the extracellular portion of the costimulatory molecule is fused to an immunoglobulin constant region. A soluble form of a T cell costimulatory molecule can be used to inhibit a costimulatory signal in T cells by contacting the T cells with the soluble molecule.

B. Antibodies

A novel structural form of a T cell costimulatory molecule of the invention can be used to produce antibodies directed against the costimulatory molecule. Conventional methods can be used to prepare the antibodies. For example, to produce polyclonal antibodies, a mammal, (e.g., a mouse, hamster, or rabbit) can be immunized with a costimulatory molecule, or an immunogenic portion thereof, which elicits an antibody response in the mammal. Techniques for conferring immunogenicity on a protein include conjugation to carriers or other techniques well known in the art. For example, the protein can be administered in the presence of adjuvant. The progress of immunization can be monitored by detection of antibody titers in plasma or serum. Standard ELISA or other immunoassay can be used with the immunogen as antigen to assess the levels of antibodies. Following immunization, antisera can be obtained and, if desired, polyclonal antibodies isolated from the sera.

In addition to polyclonal antisera, the novel costimulatory molecules of the invention can be used to raise monoclonal antibodies. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* 256, 495–497 (1975)) as well as other techniques such as the human B-cell hybridoma technique (Kozbor et al., *Immunol. Today* 4, 72 (1983)), the EBV-hybridoma technique to produce human monoclonal antibodies (Cole et al. *Monoclonal Antibodies in Cancer Therapy* (1985) Allen R. Bliss, Inc., pages 77–96), and screening of combinatorial antibody libraries (Huse et al., *Science* 246, 1275 (1989)). Hybridoma cells can be screened immunochemically for production of antibodies specifically reactive with the protein or portion thereof and monoclonal antibodies isolated.

The term antibody as used herein is intended to include fragments thereof which are also specifically reactive with an alternative cytoplasmic domain of a costimulatory molecule. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. Additonally, a chimeric antibody can be further "humanized" antibodies such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad. Sci. U.S.A.*, 80, 7308–7312 (1983); Kozbor et al., *Immunology Today*, 4, 7279 (1983); Olsson et al., *Meth. Enzymol.*, 92, 3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

Another method of generating specific antibodies, or antibody fragments, reactive against an alternative cytoplasmic domain of the invention is to screen phage expression libraries encoding immunoglobulin genes, or portions thereof, with proteins produced from the nucleic acid molecules of the present invention (e.g., with all or a portion of the amino acid sequence of SEQ ID NO: 7). For example, complete Fab fragments, VH regions and FV regions can be expressed in bacteria using phage expression libraries. See for example Ward et al., *Nature* 341, 544–546: (1989); Huse et al., *Science* 246, 1275–1281 (1989); and McCafferty et al. *Nature* 348, 552–554 (1990).

In a preferred embodiment, the invention provides an antibody which binds to a novel structural domain of a T cell costimulatory molecule provided by the invention. Such antibodies, and uses therefor, are described in greater detail below in subsection VI, part B.

C. Screening Assays

A T cell costimulatory molecule of the invention containing a novel cytoplasmic domain can be used in a screening assay to identify components of the intracellular signal tranduction pathway induced in antigen presenting cells upon binding of the T cell costimulatory molecule to its receptor on a T cell. In addition to triggering a costimulatory signal in T cells, engagement of the costimulatory molecule with a receptor on T cells is likely to deliver distinct signals to the antigen presenting cell (i.e., the cell expressing the T cell costimulatory molecule), e.g. through the cytoplasmic domain. Signals delivered through a novel cytoplasmic domain of the invention may be of particular importance in the thymus, e.g., during positive selection of T cells during development, since structural forms of costimulatory molecules comprising a novel cytoplasmic domain are preferentially expressed in the thymus. A host cell which exclusively expresses a Cyt-II form of a costimulatory molecule (e.g., mB7-1) is especially useful for elucidating such intracellular signal transduction pathways. For example, a host cell which expresses only a Cyt-II form of the costimulatory molecule can be stimulated through the costimulatory molecule, e.g., by crosslinking the costimulatory molecules on the cell surface with an antibody, and intracellular signals and/or other cellular changes (e.g., changes in surface expression of proteins etc.) induced thereupon can be identified.

Additionally, an isolated T cell costimulatory molecule of the invention comprising a novel cytoplasmic domain can be used in methods of identifying other molecules (e.g., proteins) which interact with (i.e., bind to) the costimulatory molecule using standard in vitro assays (e.g., incubating the isolated costimulatory molecule with a cellular extract and determining by immunoprecipitation if any molecules within the cellular extract bind to the costimulatory molecule). It is of particular interest to identify molecules which can interact with the novel cytoplasmic domain since such molecules may also be involved in intracellular signaling. For example, it is known that the cytoplasmic domains of many cell-surface receptors can interact intracellularly with other members of the signal transduction machinery, e.g., tyrosine kinases.

The invention further provides a method for screening agents to identify an agent which upregulates or downregulates expression of a novel structural domain form of a T cell costimulatory molecule. The method involves contacting a cell which expresses or can be induced to express a T cell costimulatory molecule with an agent to be tested and determining expression of a novel structural domain form of the T cell costimulatory molecule by the cell. The term "upregulates" encompasses inducing the expression of a novel form of a T cell costimulatory molecule by a cell which does not constitutively express such a molecule or increasing the level of expression of a novel form of a T cell costimulatory molecule by a cell which already expresses such a molecule. The term "downregulates" encompasses decreasing or eliminating expression of an a novel form of a T cell costimulatory molecule by a cell which already expresses such a molecule. The term "agent" is intended to include molecules which trigger an upregulatory or downregulatory response in a cell. For example, an agent can be a small organic molecule, a biological response modifier (e.g., a cytokine) or a molecule which can crosslink surface structures on the cell (e.g., an antibody). For example, expression of the a novel cytoplasmic domain form of the T cell costimulatory molecule by the cell can be determined by detecting an mRNA transcript encoding the novel cytoplasmic domain form of the T cell costimulatory molecule in the cell. For example, mRNA from the cell can be reverse transcribed and used as a template in PCR reactions utilizing PCR primers which can distinguish between a Cyt I cytoplasmic domain form and a novel Cyt II cytoplasmic domain form of the T cell costimulatory molecule (see e.g., Example 2). Alternatively, a novel cytoplasmic domain-containing T cell costimulatory molecule can be detected in the cell using an antibody directed against the novel cytoplasmic domain (e.g., by immunoprecipation or immunohistochemistry). A preferred T cell costimulatory molecule for use in the method is B7-1. Cell types which are known to express the Cyt-I form of B7-1, or which can be induced to express the Cyt-I form of B7-1, include B lymphocytes, T lymphocytes and monocytes. Such cell types can be screened with agents according to the method of the invention to identify an agent which upregulates or downregulates expression of the Cyt-II form of B7-1.

VI. Isolated Novel Structural Domains of T Cell Costimulatory Molecules and Uses Therefor Another aspect of the invention pertains to isolated nucleic acids encoding novel structural domains of T cell costimulatory molecules provided by the invention. In one embodiment, the structural domain encoded by the nucleic acid is a cytoplasmic domain. A preferred nucleic acid encoding a novel cytoplasmic domain comprises a nucleotide sequence shown in SEQ ID NO: 4. In another embodiment, the structural domain encoded by the nucleic acid is a signal peptide domain. A preferred nucleic acid encoding a novel signal peptide domain comprises a nucleotide sequence shown in SEQ ID NO: 14.

The invention also provides isolated polypeptides corresponding to novel structural domains of T cell costimulatory molecules, encoded by nucleic acids of the invention. In one embodiment, the structural domain is a cytoplasmic domain. A preferred novel cytoplasmic domain comprises an amino acid sequence shown in SEQ ID NO: 5. In another embodiment, the structural domain is a signal peptide domain. A preferred novel signal peptide domain comprises an amino acid sequence shown in SEQ ID NO: 15.

The uses of the novel structural domains of the invention include the creation of chimeric proteins. The domains can further be used to raise antibodies specifically directed against the domains.

A. Chimeric Proteins

The invention provides a fusion protein comprised of two peptides, a first peptide and a second peptide, wherein the second peptide is a novel structural domain of a T cell costimulatory molecule provided by the invention. In one embodiment, the novel structural domain is a cytoplasmic domain, preferably comprising an amino acid sequence shown in SEQ ID NO: 5. In another embodiment, the novel structural domain is a signal peptide domain, preferably comprising an amino acid sequence shown in SEQ ID NO: 15. For example, a fusion protein can be made which contains extracellular and transmembrane portions from a protein other than murine B7-1 and which contains a novel cytoplasmic domain (e.g., Cyt-II) of murine B7-1. This type of fusion protein can be made using standard recombinant DNA techniques in which a nucleic acid molecule encoding the cytoplasmic domain (e.g., SEQ ID NO:4) is linked in-frame to the 3' end of a nucleic acid molecule encoding the extracellular and transmembrane domains of the protein. The recombinant nucleic acid molecule can be incorporated into an expression vector and the encoded fusion protein can be expressed by standard techniques, e.g., by transfecting the recombinant expression vector into an appropriate host cell and allowing expression of the fusion protein.

A fusion protein of the invention, comprising a first peptide fused to a second peptide comprising a novel cytoplasmic domain of the invention, can be used to transfer the signal transduction function of the novel cytoplasmic domain to another protein. For example, a novel cytoplasmic domain of B7-1 (e.g., Cyt-II) can be fused to the extracellular and transmembrane domains of another protein (e.g., an immunoglobulin protein, a T cell receptor protein, a growth factor receptor protein etc.) and the fusion protein can be expressed in a host cell by standard techniques. The extracellular domain of the fusion protein can be crosslinked (e.g., by binding of a ligand or antibody to the extracellular domain) to generate an intracellular signal(s) mediated by the novel cytoplasmic domain.

Additionally, a fusion protein of the invention can be used in methods of identifying and isolating other molecules (e.g., proteins) which can interact intracellularly (i.e., within the cell cytoplasm) with a novel cytoplasmic domain of the invention. One approach to identifying molecules which interact intracellularly with the cytoplasmic domain of a cell-surface receptor is to metabolically label cells which express the receptor, immunoprecipitate the receptor, usually with an antibody against the extracellular domain of the receptor, and identify molecules which are co-immunoprecipitated along with the receptor. In the case of mB7-1, however, the cells which have been found to express the naturally-occurring Cyt-II form of B7-1 have also been found to express the naturally-occurring Cyt-I form of B7-1 (e.g., thymocytes, see Example 2). Thus, immunoprecipitation with an antibody against the extracellular domain of mB7-1 would immunoprecipitate both forms of the protein since the extracellular domain is common to both the Cyt-I and Cyt-II containing forms. Thus, molecules which interact with either Cyt-I or Cyt-II would be co-immunoprecipitate. A fusion protein comprising a non-B7-1 extracellular domain (to which an antibody can bind), a transmembrane domain (derived either from the non-B7-1 molecule or from B7-1) and a B7-1 alternative cytoplasmic domain (e.g., Cyt-II) can be constructed and expressed in a host cell which naturally expresses the Cyt-II form of B7-1. The antibody directed against the "heterologous" extracellular domain of the fusion protein can then be used to immunoprecipitate the fusion protein and to co-immunoprecipitate any other proteins which interact intracellularly with the novel cytoplasmic domain.

B. Antibodies

An antibody which binds to a novel structural domain of the invention can be prepared by using the domain, or a portion thereof, as an immunogen. Polyclonal antibodies or monoclonal antibodies can be prepared by standard techniques described above. In a preferred approach, peptides comprising amino acid sequences of the domain are used as immunogens, e.g. overlapping peptides encompassing the amino acid sequence of the domain. For example, polyclonal antisera against a novel cytoplasmic domain (e.g., Cyt II of mB7-1) can be made by preparing overlapping peptides encompassing the amino acid sequence of the domain and immunizing an animal (e.g., rabbit) with the peptides by standard techniques.

An antibody of the invention can be used to detect novel structural forms of T cell costimulatory molecules. Such an antibody is thus useful for distinguishing between expression by a cell of different forms of T cell costimulatory molecules. For example, a cell which is known to express a costimulatory molecule, such as B7-1, (for example, by the ability of an antibody directed against the extracellular portion of the costimulatory molecule to bind to the cell) can be examined to determine whether the costimulatory molecule includes a novel cytoplasmic domain of the invention. The cell can be reacted with an antibody of the invention by standard immunohistochemical techniques. For example, the antibody can be labeled with a detectable substance and the cells can be permeabilized to allow entry of the antibody into the cell cytoplasm. The antibody is then incubated with the cell and unbound antibody washed away. The presence of the detectable substance associated with the cell is detected as an indication of the binding of the antibody to a novel cytoplasmic domain expressed in the cell. Suitable detectable substances with which to label an antibody include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

C. Kinase Substrates

A novel cytoplasmic domain of the invention which contains a concensus phosphorylation site (i.e., Cyt-II of mB7-1) can be used as a substrate for a protein kinases which phosphorylates the phosphorylation site. Kinase reactions can be performed by standard techniques in vitro, e.g., by incubating a polypeptide comprising the cytoplasmic domain (or a T cell costimulatory molecule which includes the novel cytoplasmic domain) with the kinase. The kinase reactions can be performed in the presence of radiolabeled ATP (e.g., $^{32}P$-γ-ATP) to radiolabel the novel cytoplasmic domain.

This invention is further illustrated by the following examples which should not be construed as limiting. The contents of all references and published patents and patent applications cited throughout the application are hereby incorporated by reference.

The following methodology was used in the Examples.

MATERIALS AND METHODS

Genomic Cloning

A mouse 129 lambda genomic library was kindly provided by Drs. Hong Wu and Rudolf Jaenisch of the Whitehead Institute for Biomedical Research, Cambridge, Mass. Genomic DNA was prepared from the J1 embryonic stem cell line (derived from the 129/sv mouse strain), partially digested with MboI, sized (17–21 kb), and ligated into the BamHI site of lambda-DASH II arms (Stratagene, La Jolla Calif.). The library was probed with the coding region of mB7-1 cDNA to yield four clones (λ4, λ9, λ15, and λ16). These lambda clones were subcloned into Bluescript-pKS II (Stratagene, La Jolla Calif.) for subsequent restriction mapping.

Reverse Transcriptase-Polymerase Chain Reaction (RT-PCR)

Total cellular RNA was prepared from SWR/J mouse spleen and thymus using RNA-Stat-60 (Tel-Test "B", Inc, Friendswood, Tex.). Random hexamer primed reverse transcription (RT) was performed with Superscript-RT (Gibco BRL, Gaithersburg Md.) using 1–10 μg total RNA in a 20 μl reaction. All PCR reactions were performed in 25 μl volumes using a manual "hot start", wherein 10X deoxynucleotide triphosphates (dNTPs) were added to the samples at 80° C. Final reaction conditions were: 60 mM Tris-HCl, pH 8.5, 15 mM $(NH_4)_2SO_4$, 2.5 mM $MgCl_2$, 200 μM dNTPs, and 2 μg/ml each of the specific primers. Cycling conditions for all amplifications were 94° C., 4 minutes prior to 35 cycles of 94° C. for 45 seconds, 58° C. for 45 seconds, and 72° C. for 3 minutes, followed by a final extension at 72° C. for 7 minutes. The template for primary PCR was 2 μl of the RT reaction product and the template for secondary nested PCR was 1 μl of the primary PCR reaction product.

Oligonucleotides

All oligonucleotides were synthesized on an Applied Biosystems 381A DNA Synthesizer. The oligonucleotides used in this study are listed in Table I and their uses for primary or secondary PCR, as well as sense, also are indicated.

Rapid Amplification of cDNA Ends (RACE) Procedure

Polyadenylated RNA purifed by two cycles of oligo-dT selection was obtained from CH1 B lymphoma cells, which express high levels of mB7-1. Primers designed to the most 5' end of the cDNA were employed with the 5' RACE Kit (Gibco BRL, Gaithersburg, Md.) according to the manufacturer's instructions. In brief, RNA was reverse transcribed with a gene-specific oligonucleotide, the cDNA purified, and a poly-dCTP tail was added with terminal deoxynucleotide transferase. PCR was performed using a nested primer and an oligonucleotide complimentary to the poly-dCTP tail. PCR bands were cloned, sequenced, and correlated with the genomic sequences.

Oligonucleotide Hybridization

Oligonucleotide(s) were 5' end-labeled with polynucleotide kinase and $\gamma^{32}P$-ATP. Hybridizations were carried out in 5X SSC and 5% SDS at 55° C. overnight and subsequently washed 3 times for 15 minutes with 2X SSC at 55° C. Blots were exposed to Kodak XAR-5 film with an intensifying screen at −80° C.

The oligonucleotides used for the PCR studies in Examples 1–4 are shown in Table I:

TABLE I

Oligonucleotides used for PCR studies

| Designation | Sequence (5' to 3') | sense | PCR | |
|---|---|---|---|---|
| B7.27 | CCAACATAACTGAGTCTGGAAA | + | secondary | (SEQ ID NO: 43) |
| B7.36 | CTGGATTCTGACTCACCTTCA | – | secondary | (SEQ ID NO: 44) |
| B7.37 | AGGTTAAGAGTGGTAGAGCCA | – | primary | (SEQ ID NO: 45) |
| B7.38 | AATACCATGTATCCCACATGG | – | secondary | (SEQ ID NO: 46) |
| B7.42 | CTGAAGCTATGGCTTGCAATT | + | primary | (SEQ ID NO: 47) |
| B7.44 | TGGCTTCTCTTTCCTTACCTT | + | secondary | (SEQ ID NO: 48) |
| B7.48 | GCAAATGGTAGATGAGACTGT | – | secondary | (SEQ ID NO: 49) |
| B7.62 | CAACCGAGAAATCTACCAGTAA | – | probe | (SEQ ID NO: 50) |
| B7.68 | GCCGGTAACAAGTCTCTTCA | + | primary | (SEQ ID NO: 51) |
| B7.71 | AAAAGCTCTATAGCATTCTGTC | + | primary | (SEQ ID NO: 52) |
| B7.80 | ACTGACTTGGACAGTTGTTCA | + | secondary | (SEQ ID NO: 53) |
| B7.547 | TTTGATGGACAACTTTACTA | – | primary | (SEQ ID NO: 54) |

EXAMPLE 1

Characterization of the mB7-1 Genomic Locus

Lambda clones containing mB7-1 genomic DNA were isolated using a probe consisting of the coding region of mB7-1. Four representative lambda clones (designated clones λ4, λ9, λ15, and λ16) were selected for further analysis. These lambda clones were subcloned and subjected to restriction mapping with HindIII and BamHI. Regions containing exons were further characterized with XbaI and PstI. Fine mapping studies indicate that the mB7-1 locus is comprised of 6 exons arranged in the following 5' to 3' order: 5' UT plus signal peptide domain, Ig-V-like domain, Ig-C-like domain, transmembrane domain, cytoplasmic domain I, and the alternative cytoplasmic domain II, to be discussed below. The 4 lambda clones spanned over 40 kb of the mB7-1 locus, excluding a gap of undetermined size between exon 1 (signal exon) and exon 2 (Ig-V-like exon). The gap between clones λ15 (transmembrane domain exon) and λ16 (cytoplasmic domain exon) was determined to be less than 100 base pairs by PCR using a sense primer (B7.71) designed to the 3' end of clone λ15 and an antisense primer (B7.38) located at the 5' end of clone λ16. Clones λ9 and λ15 overlapped in a region spanning exon 2.

EXAMPLE 2

Identification of mB7-1 Exon 6: An Alternately Spliced Exon Encoding a Novel Second Cytoplasmic Domain Analysis of mB7-1 cDNAs isolated from an A20 B cell cDNA library showed that one cDNA contained additional sequence not previously described for the mB7-1 cDNA. This sequence was mapped to the mB7-1 locus approximately 7-kb downstream of exon 5. A canonical splice site was present immediately upstream of this sequence and a poly-adenylation site was present downstream. Taken together, these data suggested that this novel sequence represents an additional exon, encoding 46 amino acids, which may be alternatively spliced in place of exon 5. This alternative cytoplasmic domain is notable for two casein kinase II phosphorylation sites (amino acid positions 11–15 (SAKDF) and amino acid positions 28–32 (SLGEA) of SEQ ID NO: 5) (for a description of casein kinase II phosphorylation sites see Pinna (1990) *Biochimica et Biophysica Acta* 1054:267–284) and one protein kinase C phosphorylation site (amino acid positions 11–14 (SAKD) of SEQ ID NO: 5)(for a description of protein kinase C phosphorylation sites see Woodgett et al. (1986) *Biochemistry* 161:177–184; and Kishimoto et al. (1985) *J. Biol. Chem.* 260:12492–12499).

In order to assess whether exon 6 also could be used in an alternative fashion, an antisense primer (B7.48) was designed to the predicted exon 4/6 splice junction such that only the alternatively spliced product would give rise to an amplified product. This primer overhangs the putative exon 4/6 junction by 3 bp at its 3' end. The 3 bp overhang is insufficient to permit direct priming in exon 4 outside the context of an exon 4/6 splice (FIG. 1, lane 9, negative control is a cDNA clone containing only mB7-1 CytI). The expected amplified product for the alternately spliced transcript (FIG. 1, transcript C) would be 399 bp. Interestingly, this transcript was observed only in thymic, but not splenic RNA. [In FIG. 1, lanes 1, 2 and 3 represent nested PCR products from murine splenic RNA using PCR primers B7.27–B7.36, B7.27–B7.38, and B7.27–B7.48, respectively. Lanes 4, 5 and 6 represent nested PCR products from murine thyrnic RNA using PCR primers B7.27–B7.36, B7.27–B7.38 and B7.27–B7.48, respectively. Lane 7 represents a negative control (no input RNA). Lane 8 represents a positive control (mB7-1 cDNA clone). Lane 9 represents a negative control for B7.27–B7.48 amplification comprised of the mB7-1 cDNA containing cytoplasmic domain I, which does not have the correct exon 4–6 splice junction. Lane M is a 100 bp ladder with the lower bright band equal to 600 bp. Letters A, B and C refer to the transcripts detected and are further illustrated in FIG. 1. Note that exon 6 splicing as an alternative cytoplasmic domain is present only in the thymus, but not in the spleen].

To further investigate the use of exon 6 in mB7-1 mRNA transcripts, nested RT-PCR spanning exons 3 through 6 was performed using spleen RNA (FIG. 1, PCR product A). A PCR product longer than predicted from the use of exon 6 as an alternatively spliced exon also was observed. Subsequent sequence analysis indicated that in this transcript, exons 5 and 6 were spliced in tandem, rather than in an alternative fashion (FIG. 1, transcript A), making use of a previously unrecognized splice donor site downstream of the termination codon in exon 5. Thus, this alternative transcript would not change the encoded protein. Subsequent sequence analysis of a larger than expected product observed from spleen RNA (FIG. 1, lane 3) revealed an additional example of the tandem splicing of exon 6 to exon 5 using an alternative noncanonical splice site. Transcripts with tandem splicing of exon 6 to exon 5 were observed in the spleen and the thymus.

Figure 2:
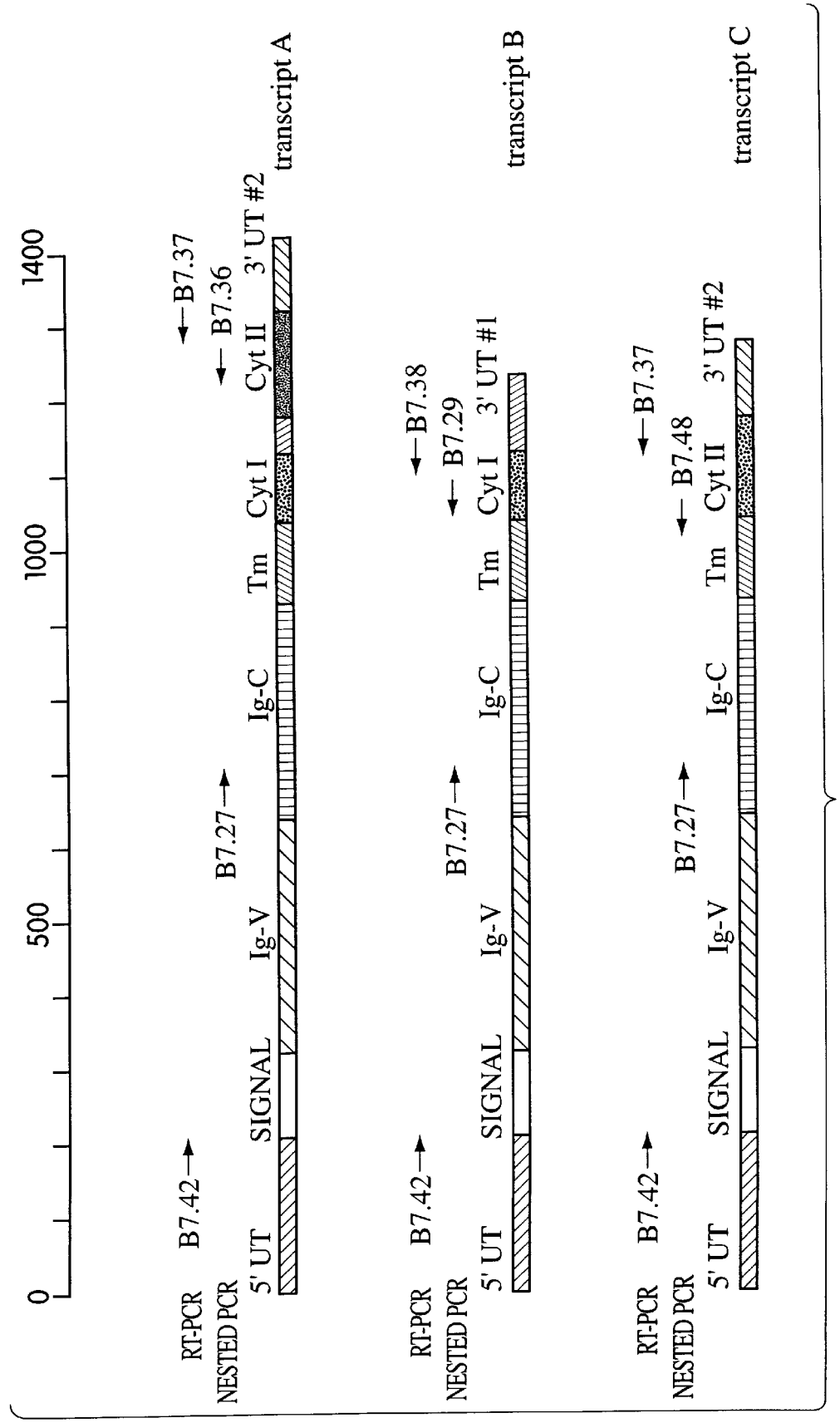
FIG. 2 is a schematic representation depicting three mB7-1 transcripts (A, B and C) detected by nested RT-PCR.

FIG. 2 is a schematic diagram of the three mB7-1 transcripts (A, B, and C) detected by nested RT-PCR. Exons are depicted in different shades of gray and untranslated sequences are white. Oligonucleotide primers used for the initial RT-PCR and subsequent nested PCR are indicated above their respective locations in the transcripts. Only B7.48 spans an exon-exon junction as indicated. The scale bar above indicates the length in base pairs.

EXAMPLE 3

Identification of Additional mB7-1 5' Untranslated Sequences

Rapid amplification of cDNA ends (RACE) is a PCR-based strategy to determine the 5' end of a transcript. Three distinct rounds of 5' RACE were performed on polyadenylated RNA from CH1 B lymphoma cells, which express high levels of mB7-1 RNA. The resulting sequences extended the 5' UT of the known mB7-1 cDNA by 1505 bp, beyond the transcriptional start site reported by Selvakumar et al. ((1993) *Immunogenetics* 38:292–295). In order to confirm that this long 5' UT sequence was indeed in the mB7-1 mRNA and not generated by PCR amplification of genomic DNA, a nested RT-PCR amplification (B7.68–B7.547 followed by B7.44–B7.80) was performed. This amplification spans exon 2 (primer B7.80) and the novel 5' UT sequences in exon 1 (B7–44), and should yield an 840 bp PCR product. It should be noted that exon 2 is separated from exon 1 by greater than 12 kb in genomic DNA, thus making a genomic DNA-derived PCR product of almost 13 kb. The predicted band of 840 bp, indeed, was observed when this nested PCR amplification was performed. To further confirm the nature of the PCR product, hybridization was performed with an oligonucleotide (B7.62) derived from sequences in exon 1 located 5' of the transcriptional start site reported by Selvakumar et al. ((1993) *Immunogenetics* 38:292–295). This probe hybridized to the PCR product. In addition, sequencing of the RACE product revealed that it contained sequences identical to the previously known genomic sequences immediately upstream of the known exon 1 and was contiguous with exon 1. Thus, it did not identify an additional exon.

EXAMPLE 4

Fine Mapping of mB7-1 Intron-Exon Boundaries

In order to characterize intron-exon boundaries, oligonucleotide primers were synthesized to mB7-1 cDNA sequences (described in Freeman et al. (1991) *J. Exp. Med.* 174:625–631), as well as to sequences determined from PCR products characterized during amplifications from tissue RNA. Sequences for exons 1 through 5, as well as exon-intron junctions have been reported previously (Selvakumar et al. (1993) *Immunogenetics* 38:292–295). The coding region of the exon 1 signal peptide domain is 115 bp and is flanked at the 3' end with a canonical splice site. Exons 2 (318 bp), 3 (282 bp), and 4 (114 bp), are separated by 6.0 and 3.8 kb, respectively, and all 3 exons are flanked on both their 5' and 3' ends with canonical splice sites. Exon 5 is located 4 kb downstream of exon 4, and contains a termination codon after the first 97 bp. An additional functional canonical splice site was observed 43 bp downstream of the termination codon in exon 5, since this site was used to generate the transcript outlined in FIG. 1 (transcript A). Exon 6 is located 7.2 kb downstream of exon 5 and encodes an open reading frame with a termination codon after 140 bp. Both exons 5 and 6 are followed by polyadenylation sequences, ATTAAA and AATAAA respectively.

EXAMPLE 5

Identification of Additional Novel Cytoplasmic Domains by Exon Trapping

In this example, an exon trapping approach is used to identify a novel exon encoding an alternative cytoplasmic domain for human B7-1. The basic strategy of exon trapping is to create an expression vector encoding a recombinant protein, wherein the encoded protein cannot be functionally expressed unless an appropriate exon, with flanking intron sequences that allow proper mRNA splicing, is cloned into the expression vector. A recombinant expression vector is created comprising transcriptional regulatory sequences (e.g., a strong promoter) linked to nucleic acid encoding the human B7-1 signal peptide exon, IgV-like and IgC-like exons followed by a transmembrane exon with flanking 3' intron donor splice sequences. These splice sequences are immediately followed by translational stop codons in all three frames. A polyadenylation recognition site is not included in the recombinant expression vector. Following the stop codons are restriction enzyme sites which allow genomic DNA fragments to be cloned into the expression vector to create a library of recombinant expression vectors.

As a negative control, the parental recombinant expression vector is transfected into a host cell line which is hB7-1⁻ (e.g, COS cells) and the absence of surface expression of hB7-1 is demonstrated, confirming that the parental expression vector alone is unable to direct stable surface expression of hB7-1 in the absence of a cytoplasmic domain encoding exon. As a positive control, the known hB7-1 cytoplasmic domain with a flanking 5' intron acceptor splice sequence is cloned into a restriction enzyme site downstream of the transmembrane exon such that the transmembrane domain exon can be spliced to the cytoplasmic domain exon. This positive control vector is transfected into a host cell (e.g., COS cells) and the surface expression of hB7-1 on the cells is demonstrated, confirming that the cloning into the vector of a cytoplasmic domain encoding exon with the proper splice sequences produces an hB7-1 molecule that can be stably expressed on the cell surface.

To identify an alternative hB7-1 cytoplasmic domain exon, genomic DNA fragments for the hB7-1 gene are cloned into the parental recombinant expression at the restiction enzyme sites downstream of the transmembrane domain exon. Cloning of genomic fragments into the vector will "trap" DNA fragments which encompass a functional exon preceded by an intron splice acceptor site and followed by a polyadenylation signal, since cloning of such fragments into the vector allows for expression of a functional recombinant protein on the surface of transfected host cells. The diversity of the genomic DNA fragments cloned into the vector directly impacts the variety of sequences "trapped". Were total genomic DNA to be used in such an approach, a variety of exons would be trapped, including cytoplasmic domains from proteins other than T cell costimulatory molecules. However, instead of using total genomic DNA for subcloning into the expression vector, only genomic DNA fragments located in the vicinity of the exon encoding a known cytoplasmic domain of the T cell costimulatory molecule of interest are subcloned into the vector. For example, for human B7-1, genomic DNA clones can be isolated by standard techniques which contain DNA located within several kilobases 5' or 3' of the hB7-1 exon which encodes the known cytoplasmic domain. These fragments are cloned into the parental recombinant expression vector to create a library of expression vectors. The library of expression vectors is then transfected into a host cell (e.g., COS cells) and the transfectants are screened for surface expression of hB7-1. Cell clones which express a functional B7-1 molecule on their surface are identified and affinity purified (e.g., by reacting the cells with a molecule which binds to B7-1, such as an anti-B7-1 monoclonal antibody (e.g., mAb 133 describe in Freedman, A. S. et al. (1987) *J. Immunol.* 137:3260; and Freeman, G. J. et al. (1989) *J. Immunol.* 143:2714) or a CTLA4Ig protein (described in Linsley, P. S. et al., (1991) *J. Exp. Med.* 174:561–569). Cell clones which express a B7-1 molecule on their surface will have incorporated into the expression vector DNA encoding a functional cytoplasmic domain (e.g., an alternative cytoplasmic domain encoded by a different exon than the known cytoplasmic domain). DNA from positive clones encoding the alternative cytoplasmic domain can then be amplified by PCR using a sense primer corresponding to the transmembrane domain and an antisense primer corresponding to vector sequences.

This same approach can be adapted by the skilled artisan to identify alternative cytoplasmic domains for other T cell costimulatory molecules (e.g., B7-2) or to "trap" exons encoding other alternative structural domains of T cell costimulatory molecules.

EXAMPLE 6

Identification of a Novel B7-2 Signal Peptide Domain cDNA fragments corresponding to the 5' ends of naturally-occurring murine B7-2 mRNA transcripts were prepared by 5' RACE: polyadenylated RNA isolated from murine spleen cells was reverse transcribed with a gene-specific oligonucleotide, the cDNA was isolated, and a poly-dCT tail was added to the 5' end with terminal deoxynucleotide transferase. PCR was perfomed using a nested primer and an oligonucleotide primer complementary to the poly-dCTP tail to amplify 5' cDNA fragments of mB7-2 transcripts. The gene-specific oligonucleotide primers used for PCR were as follows:

```
CAGCTCACTCAGGCTTATGT   reverse transcription, - sense   (SEQ ID NO: 55)
AAACAGCATCTGAGATCAGCA  primary PCR, - sense             (SEQ ID NO: 56)
CTGAGATCAGCAAGACTGTC   secondary PCR, - sense           (SEQ ID NO: 57)
```

The amplified fragments were subcloned into a plasmid vector and sequenced. Of approximately 100 individual clones examined, ~75% of the clones had a 5' nucleotide sequence corresponding to that reported for the 5' end of an mB7-2 CDNA (see Freeman, G. J. et al. (1993) *J. Exp. Med.* 11:2185–2192). Approximately 25% of the clones had a 5' nucleotide sequence shown in SEQ ID NO: 14, which encodes a novel signal peptide domain having an amino acid sequence shown in SEQ ID NO: 15.

EXAMPLE 7

Identification of an Alternatively Spliced Form of B7-1 Having a Structural Domain Deleted Reverse-transcriptase polymerase chain reaction was used to amplify mB7-1 cDNA fragments derived from murine spleen cell RNA. Oligonucleotide primers used for PCR were as follows:

```
CTGAAGCTATGGCTTGCAATT   primary PCR, + sense    (SEQ ID NO: 58)
ACAAGTGTCTTCAGATGTTGAT  secondary PCR, + sense  (SEQ ID NO: 59)
CTGGATTCTGACTCACCTTCA   primary PCR, - sense    (SEQ ID NO: 60)
CCAGGTGAAGTCCTCTGACA    secondary PCR, - sense  (SEQ ID NO: 61)
```

A cDNA fragment was detected which comprises a nucleotide sequence (SEQ ID NO:8) encoding a murine B7-1 molecule in which the signal peptide domain was spliced directly to the IgC-like domain (i.e., the IgV-like domain was deleted). The amino acid sequence of mB7-1 encoded by this cDNA is shown in SEQ ID NO:9.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated B7-1 or B7-2 polypeptide which binds CD28 or CTLA4, comprising an amino acid sequence of SEQ ID NO:2, wherein the polypeptide is encoded by a nucleic acid molecule which hybridizes to a complement of a nucleic acid molecule consisting of SEQ ID NO: 1 in 5X SSC and 0.5% SDS at 55° C., followed by one or more washes in 2X SSC at 55° C.

2. An isolated B7-1 or B7-2 polypeptide which binds CD28 or CTLA4, comprising an amino acid sequence of SEQ ID NO:5, wherein the polypeptide is encoded by a nucleic acid molecule which hybridizes to a complement of a nucleic acid molecule consisting of SEQ ID NO:4 in 5X SSC and 0.5% SDS at 55° C., followed by one or more washes in 2X SSC at 55° C.

3. An isolated B7-1 or B7-2 polypeptide which binds CD28 or CTLA4, comprising an amino acid sequence of SEQ ID NO:9, and not comprising an amino acid sequence corresponding to an immunoglobulin variable region-like domain, wherein the polypeptide is encoded by a nucleic acid molecule which hybridizes to a complement of a nucleic acid molecule consisting of SEQ ID NO:8 in 5X SSC and 0.5% SDS at 55° C., followed by one or more washes in 2X SSC at 55° C.

4. An isolated B7-1 or B7-2 polypeptide which binds CD28 or CTLA4, comprising an amino acid sequence of SEQ ID NO: 11, wherein the polypeptide is encoded by a nucleic acid molecule which hybridizes to a complement of a nucleic acid molecule consisting of SEQ ID NO: 10 in 5X SSC and 0.5% SDS at 55° C., followed by one or more washes in 2X SSC at 55° C.

5. An isolated B7-1 or B7-2 polypeptide which binds CD28 or CTLA4, comprising an amino acid sequence of SEQ ID NO: 13, wherein the polypeptide is encoded by a nucleic acid molecule which hybridizes to a complement of a nucleic acid molecule consisting of SEQ ID NO:12 in 5X SSC and 0.5% SDS at 55° C., followed by one or more washes in 2X SSC at 55° C.

6. An isolated B7-1 or B7-2 polypeptide which binds CD28 or CTLA4, comprising an amino acid sequence of SEQ ID NO: 15, wherein the polypeptide is encoded by a nucleic acid molecule which hybridizes to a complement of a nucleic acid molecule consisting of SEQ ID NO:14 in 5X SSC and 0.5% SDS at 55° C., followed by one or more washes in 2X SSC at 55° C.

7. An isolated polypeptide consisting of the amino acid sequence of SEQ ID NO:2.

8. An isolated polypeptide consisting of the amino acid sequence of SEQ ID NO:5.

9. An isolated polypeptide consisting of the amino acid sequence of SEQ ID NO:9.

10. An isolated polypeptide consisting of the amino acid sequence of SEQ ID NO: 11.

11. An isolated polypeptide consisting of the amino acid sequence of SEQ ID NO:13.

12. An isolated polypeptide consisting of the amino acid sequence of SEQ ID NO:15.

\* \* \* \* \*